US012173042B2

(12) United States Patent
Lengyel et al.

(10) Patent No.: US 12,173,042 B2
(45) Date of Patent: Dec. 24, 2024

(54) METHODS OF TREATING CANCERS WITH CT45 TARGETED THERAPIES

(71) Applicants: The University of Chicago, Chicago, IL (US); Max-Planck-Gesellschaft Zur Forderung Der Wissenschaften E.V., Munich (DE)

(72) Inventors: Ernst Lengyel, Chicago, IL (US); Matthias Mann, Munich (DE); Marion Curtis, Chicago, IL (US); Fabian Coscia, Munich (DE)

(73) Assignees: The University of Chicago; Max-Planck-Gesellschaft Zur Forderung Der Wissenschaften E. V., Munich (DE)

( * ) Notice: Subject to any disclaimer, the term of this patent is extended or adjusted under 35 U.S.C. 154(b) by 175 days.

(21) Appl. No.: 17/649,200

(22) Filed: Jan. 28, 2022

(65) Prior Publication Data

US 2022/0153797 A1    May 19, 2022

Related U.S. Application Data

(62) Division of application No. 16/300,267, filed as application No. PCT/IB2017/052781 on May 11, 2017, now Pat. No. 11,261,223.

(60) Provisional application No. 62/334,782, filed on May 11, 2016.

(51) Int. Cl.

| | | |
|---|---|---|
| C07K 14/47 | (2006.01) | |
| A61K 31/337 | (2006.01) | |
| A61K 31/555 | (2006.01) | |
| A61K 31/706 | (2006.01) | |
| A61K 33/243 | (2019.01) | |
| A61K 35/17 | (2015.01) | |
| A61K 38/17 | (2006.01) | |
| A61K 38/20 | (2006.01) | |
| A61K 39/00 | (2006.01) | |
| A61K 39/395 | (2006.01) | |
| A61K 45/06 | (2006.01) | |
| A61P 35/00 | (2006.01) | |
| C07K 14/725 | (2006.01) | |
| C07K 16/30 | (2006.01) | |
| C12N 5/0783 | (2010.01) | |
| C12Q 1/6886 | (2018.01) | |
| G01N 33/574 | (2006.01) | |

(52) U.S. Cl.
CPC ........ *C07K 14/4748* (2013.01); *A61K 31/337* (2013.01); *A61K 31/555* (2013.01); *A61K 31/706* (2013.01); *A61K 33/243* (2019.01); *A61K 35/17* (2013.01); *A61K 38/1774* (2013.01); *A61K 38/2013* (2013.01); *A61K 39/39558* (2013.01); *A61K 45/06* (2013.01); *A61P 35/00* (2018.01); *C07K 14/7051* (2013.01); *C07K 16/30* (2013.01); *C12N 5/0636* (2013.01); *C12Q 1/6886* (2013.01); *G01N 33/57449* (2013.01); *A61K 2039/5154* (2013.01); *A61K 2039/5158* (2013.01); *C07K 2317/31* (2013.01); *C07K 2317/622* (2013.01); *C07K 2319/03* (2013.01); *C12N 2501/02* (2013.01); *C12N 2501/22* (2013.01); *C12N 2501/2301* (2013.01); *C12N 2501/25* (2013.01); *G01N 2800/52* (2013.01)

(58) Field of Classification Search
None
See application file for complete search history.

(56) References Cited

U.S. PATENT DOCUMENTS

| | | |
|---|---|---|
| 2006/0275794 A1 | 12/2006 | Carrino et al. |
| 2011/0177079 A1 | 7/2011 | Chen et al. |
| 2012/0042399 A1 | 2/2012 | Pulford et al. |
| 2013/0078250 A1 | 3/2013 | Ast et al. |
| 2013/0287748 A1 | 10/2013 | June et al. |
| 2017/0002055 A1 | 1/2017 | Mahr et al. |
| 2017/0037094 A1 | 2/2017 | Mahr et al. |

OTHER PUBLICATIONS

Almagro and Fransson. "Humanization of antibodies" *Frontiers in Bioscience* 2008; 13:1619-33.
Arstila et al., "A Direct Estimate of the Human αβ T Cell Receptor Diversity" *Science* 1999, 286: 958-961.
Chen et al., "Cancer/testis antigen CT45: Analysis of mRNA and protein expression in human cancer" *Int. J. Cancer* 2009, 124, 2893-2898.
Gjerstorff, et al., "Oncogenic Cancer/Testis Antigens: Prime Candidates for Immunotherapy," *Oncotarget*, 6(18); 15772-15787, 2015.
International Search Report and Written Opinion Issued in Corresponding PCT Application No. PCT/IB2017/052781, mailed Sep. 6, 2017.
Jaffray DA and Gospodarowicz MK. *Radiation Therapy for Cancer*, edited by Hellen Gelband, Prabhat Jha, Rengaswamy Sankaranarayanan, and Susan Horton. *Cancer: Disease Control Priorities*, Third Edition (vol. 3). Washington (DC): Nov. 1, 2015. Chapter 14 (Excerpt).
Jena et al., "Redirecting T-cell specificity by introducing a tumor-specific chimeric antigen receptor" *Blood* 2010, 116(7), 1035-1044.
Koop, et al., "Down-Regulation of the Cancer/Testis Antigen 45 (CT45) is Associated with Altered Tumor Cell Morphology, Adhesion and Migration," *Cell Communication and Signaling*, 11(41); 1-12, 2013.
Roett and Evans "Ovarian Cancer: an Overview" Am. Fam. Physician 2009, 80(6), 609-616.

(Continued)

*Primary Examiner* — Peter J Reddig
(74) *Attorney, Agent, or Firm* — Norton Rose Fulbright US LLP; Laurie Stellman

(57) ABSTRACT

The current disclosure relates to methods for treating ovarian cancer based on specific antigen expression of the cancer. Furthermore, the expressed antigen may be used in immunotherapeutic methods for treatment of the ovarian cancer. Aspects of the disclosure relate to immunotherapies targeting CT45 polypeptides, methods for treating ovarian cancer based on CT45 expression, and kits for detecting CT45 polypeptides and nucleotides.

6 Claims, 43 Drawing Sheets

Specification includes a Sequence Listing.

(56) References Cited

OTHER PUBLICATIONS

Shang, et al., "CT45A1 Acts as a New Proto-Oncogene to Trigger Tumorigenesis and Cancer Metastasis," *Cell Death & Disease*, 5; e1285, 2014.

Simpson, et al., "Cancer/Testis Antigens, Gametogenesis and Cancer," *Nature Reviews*, Cancer 5; 615-625, 2005.

Winkler, et al., "Hodgkin's Lymphoma RNA-Transected Dendritic Cells Induce Cancer/Testis Antigen-Specific Immune Responses," *Cancer Immunology, Immnotherapy*, 61(10); 1769-1779, 2012.

Zhang, et al., "DNA Hypomethylation-Mediated Activation of Cancer/Testis Antigen 45 (CT45) Genes is Associated with Disease Progression and Reduced Survival in Epithelial Ovarian Cancer," *Epigenetics*, 10(8); 736-748, 2015.

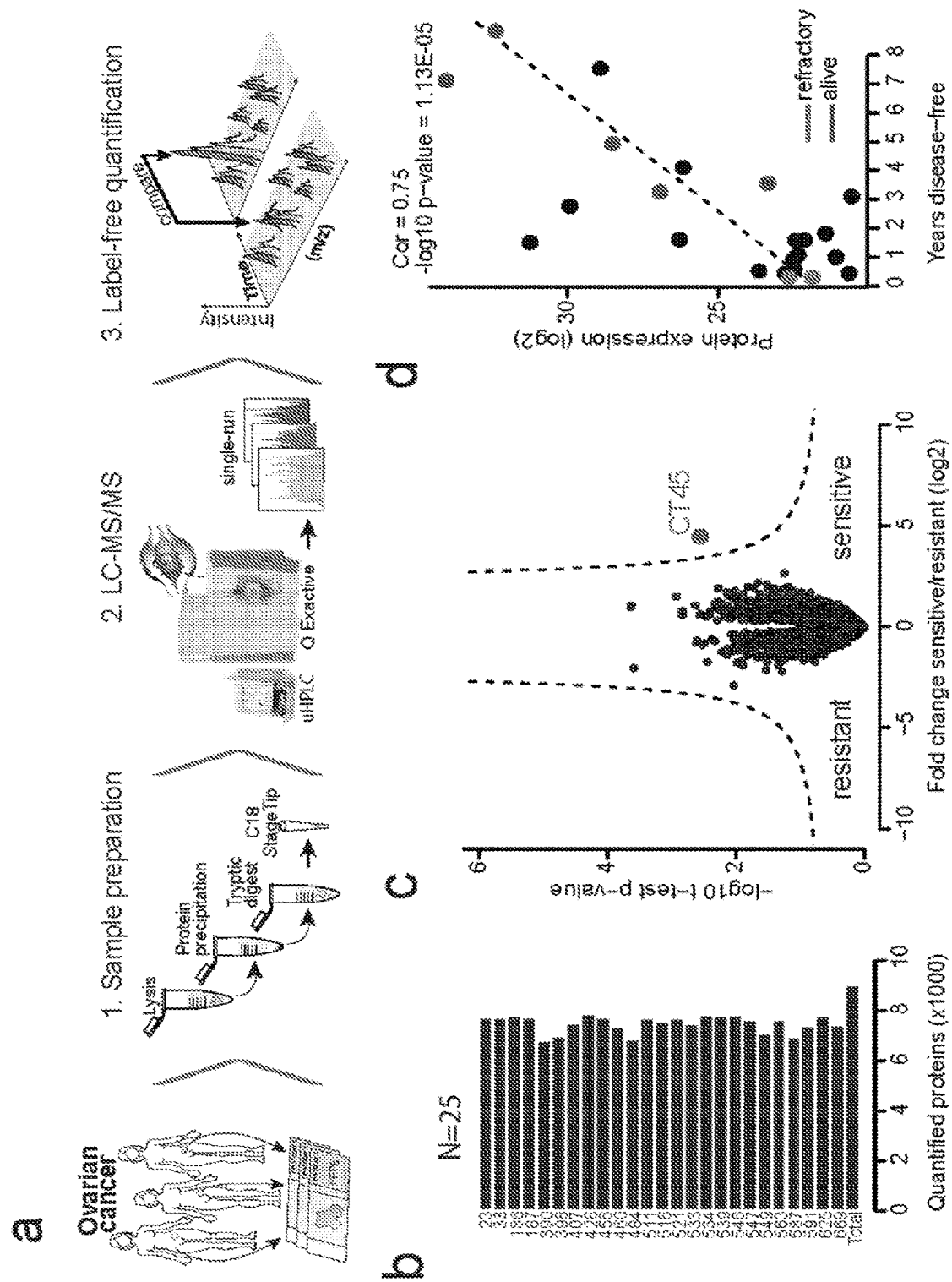
FIG. 1A-D

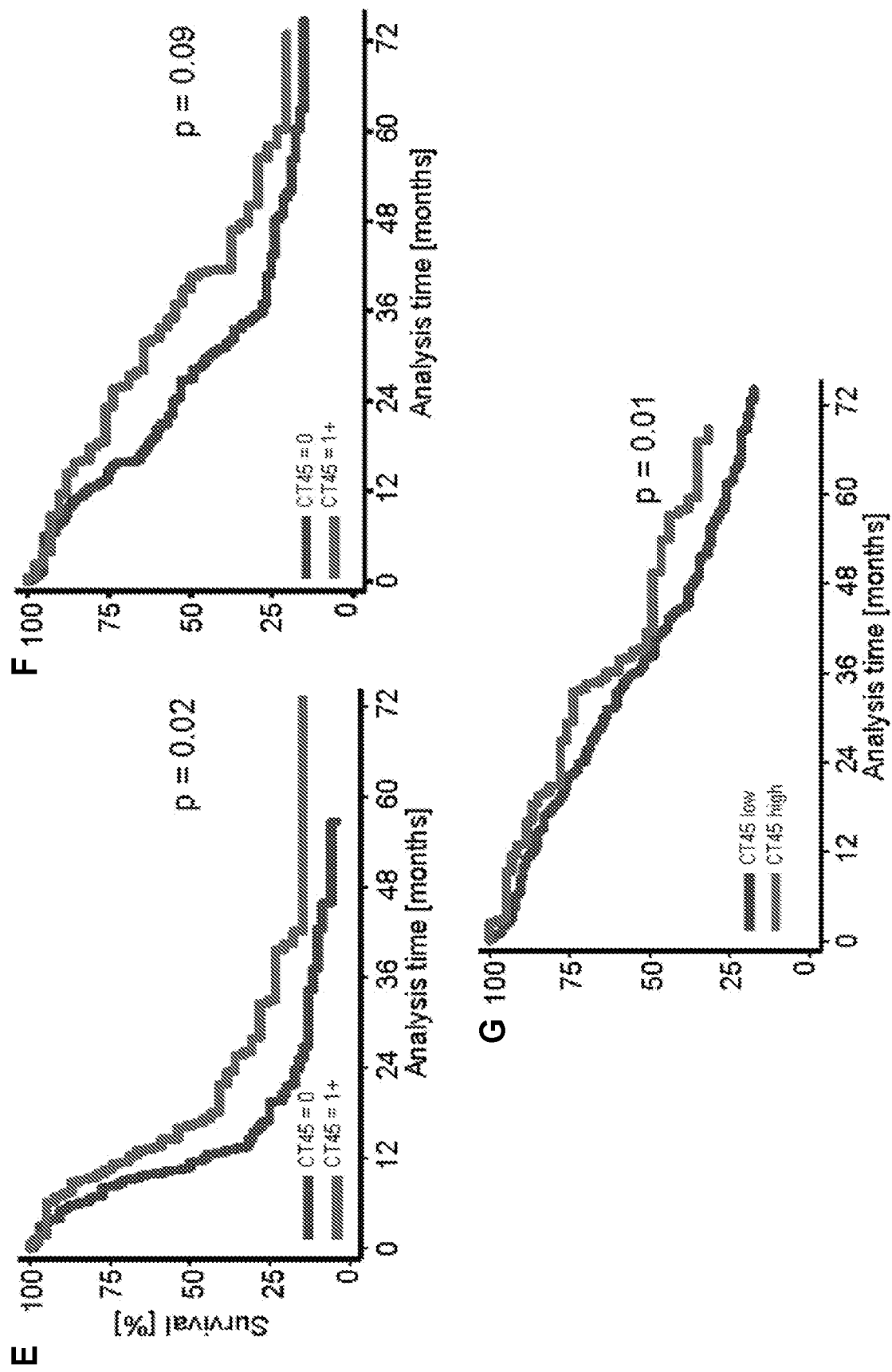
FIG. 1E-G

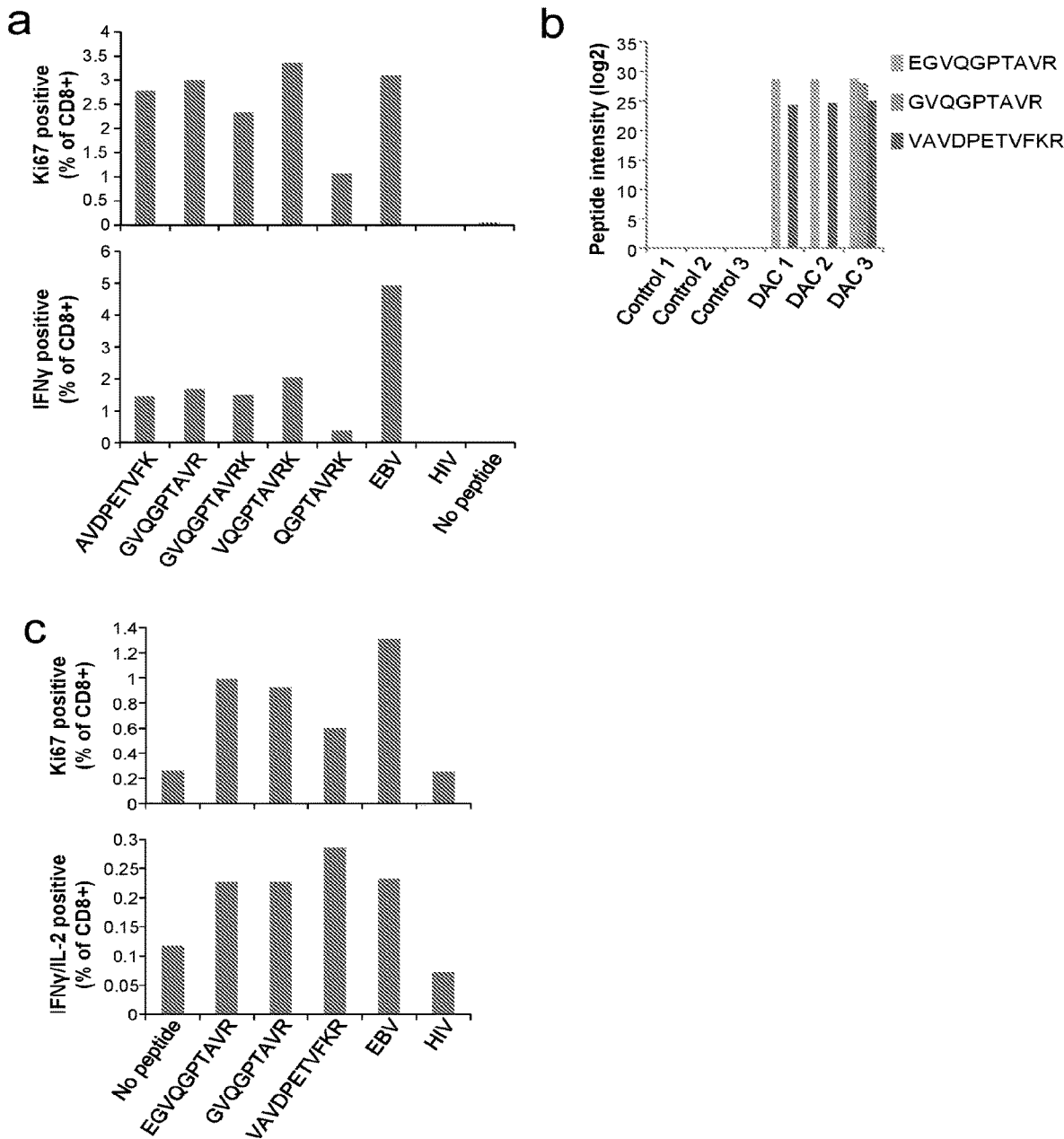
FIG. 2A-C

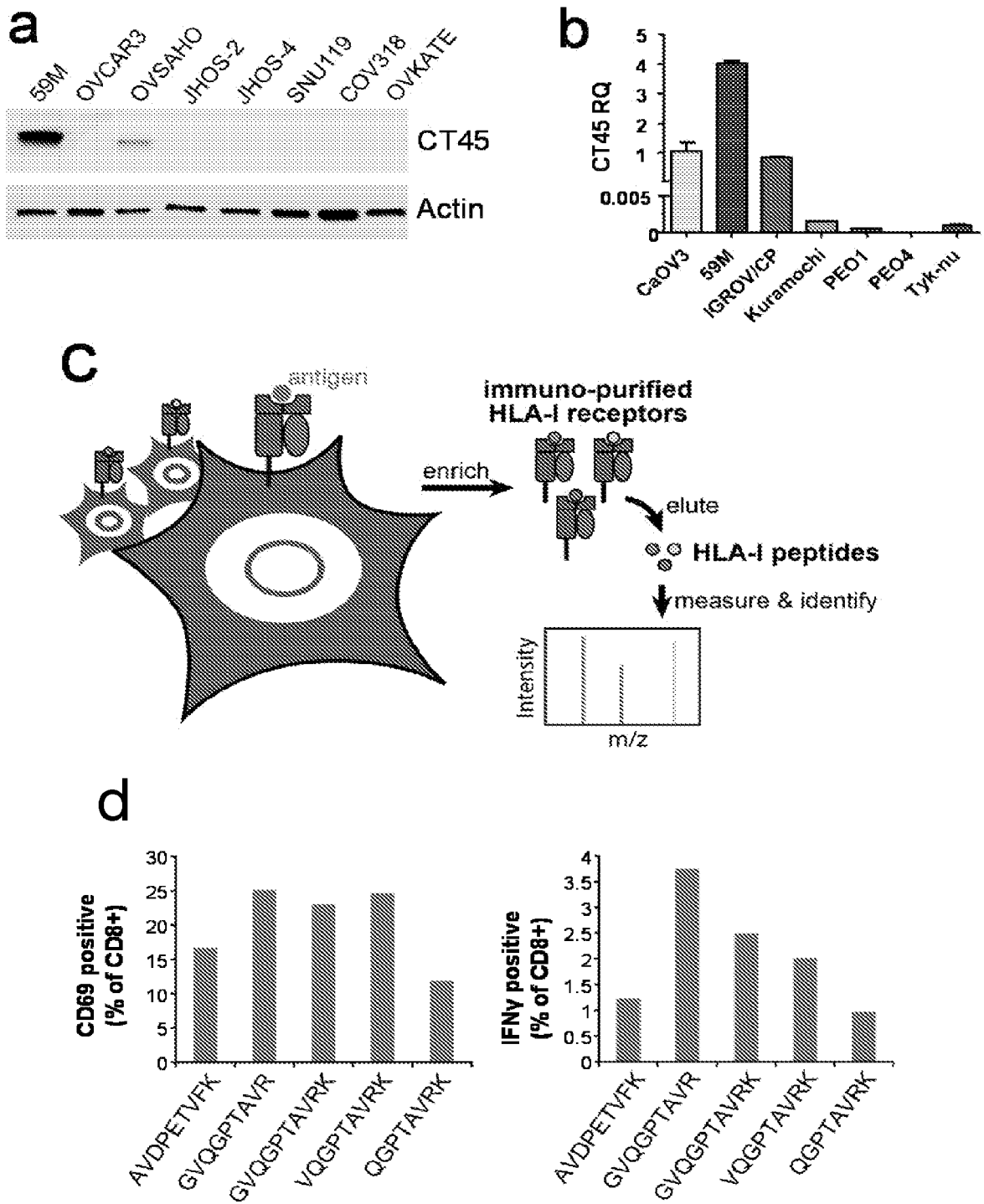
FIG. 5A-D

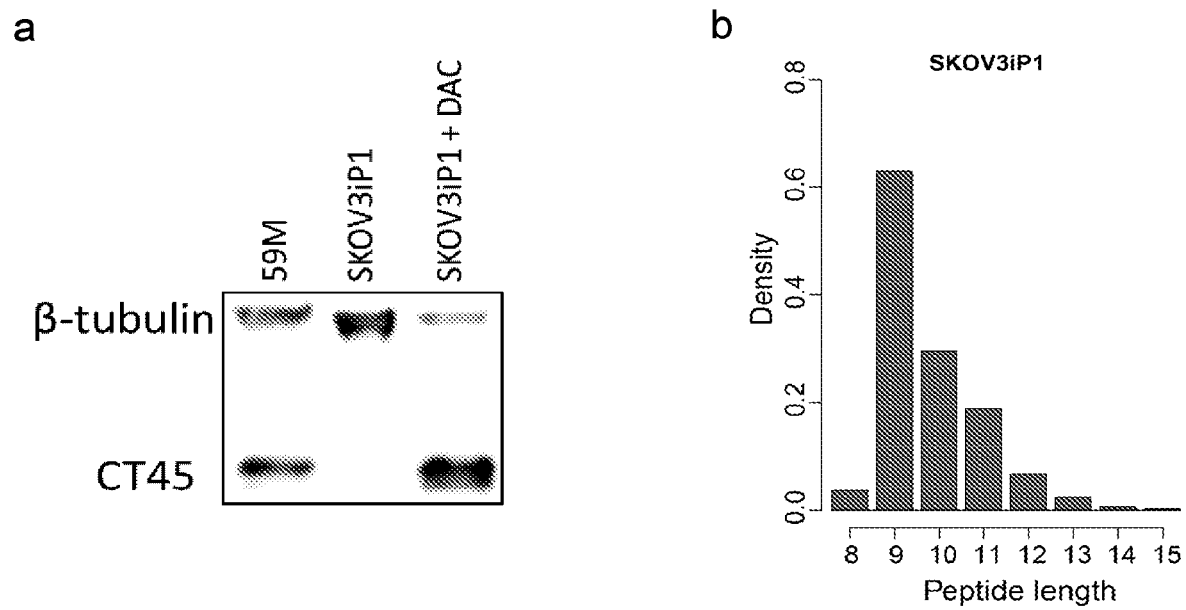
FIG. 6A-B
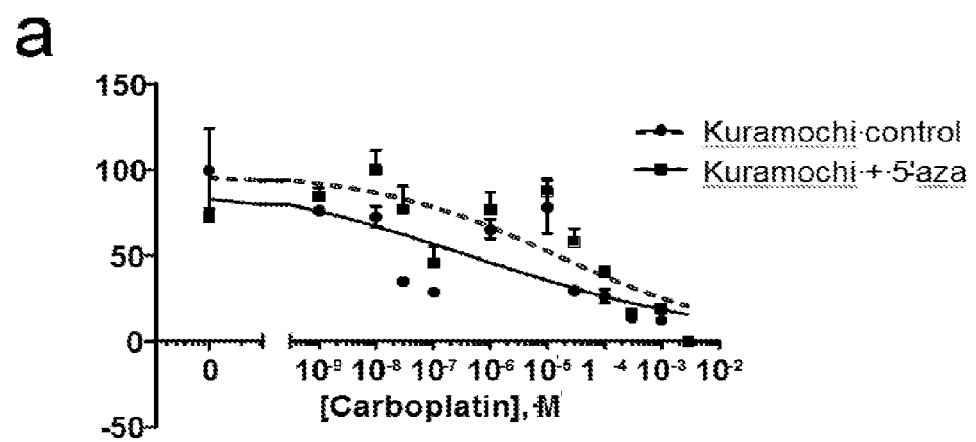
FIG. 7A

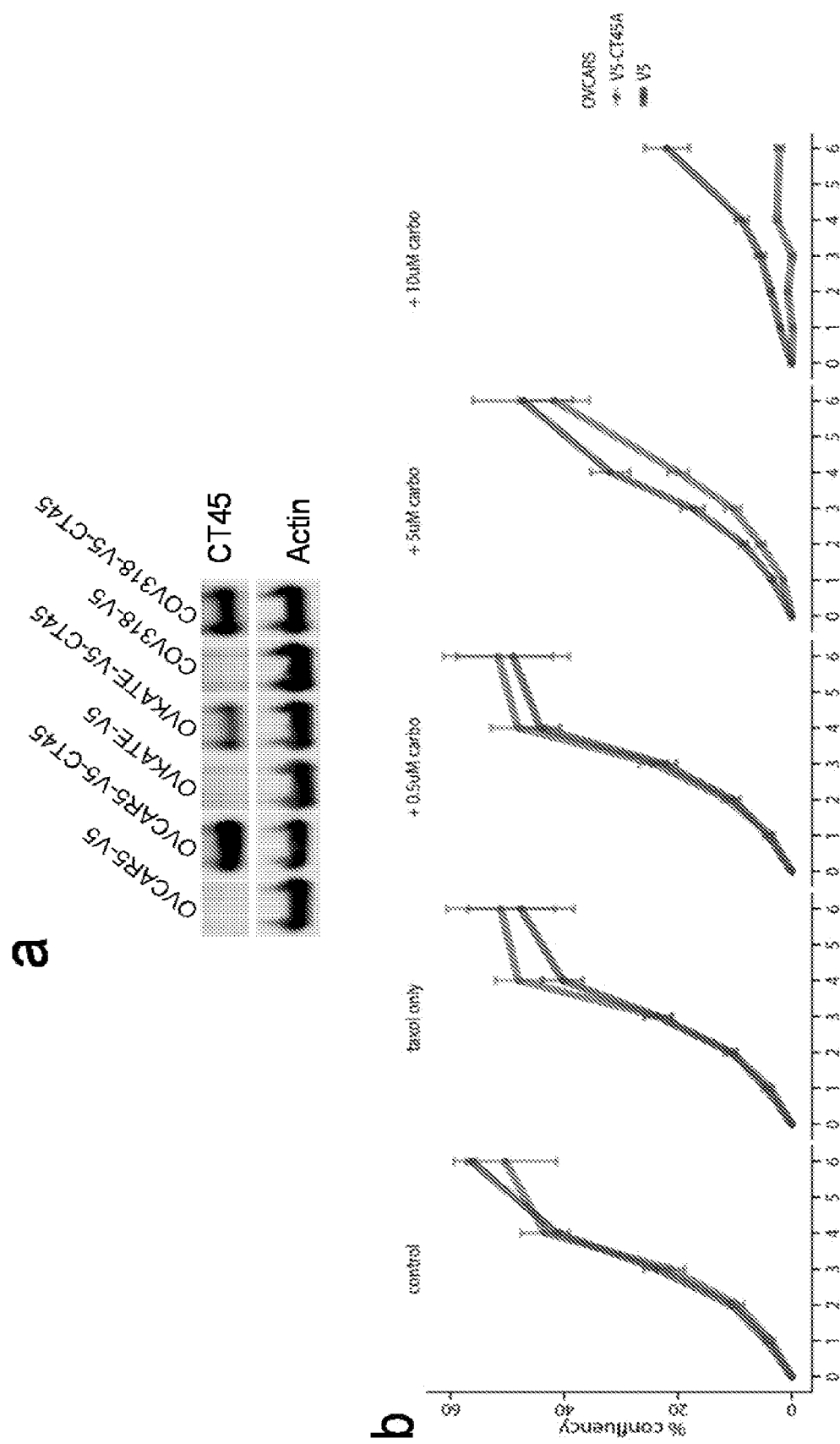
FIG. 8A-B

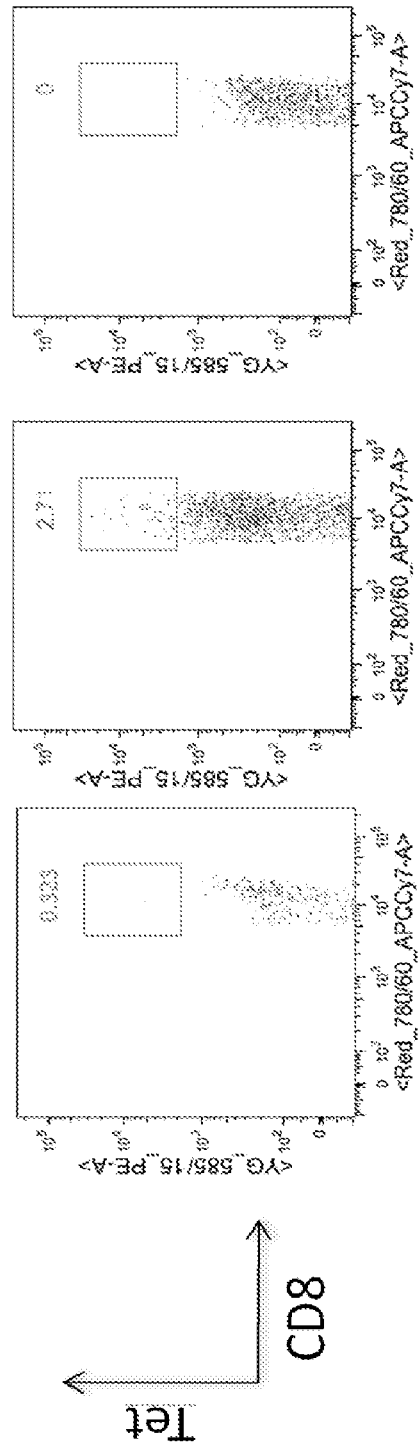
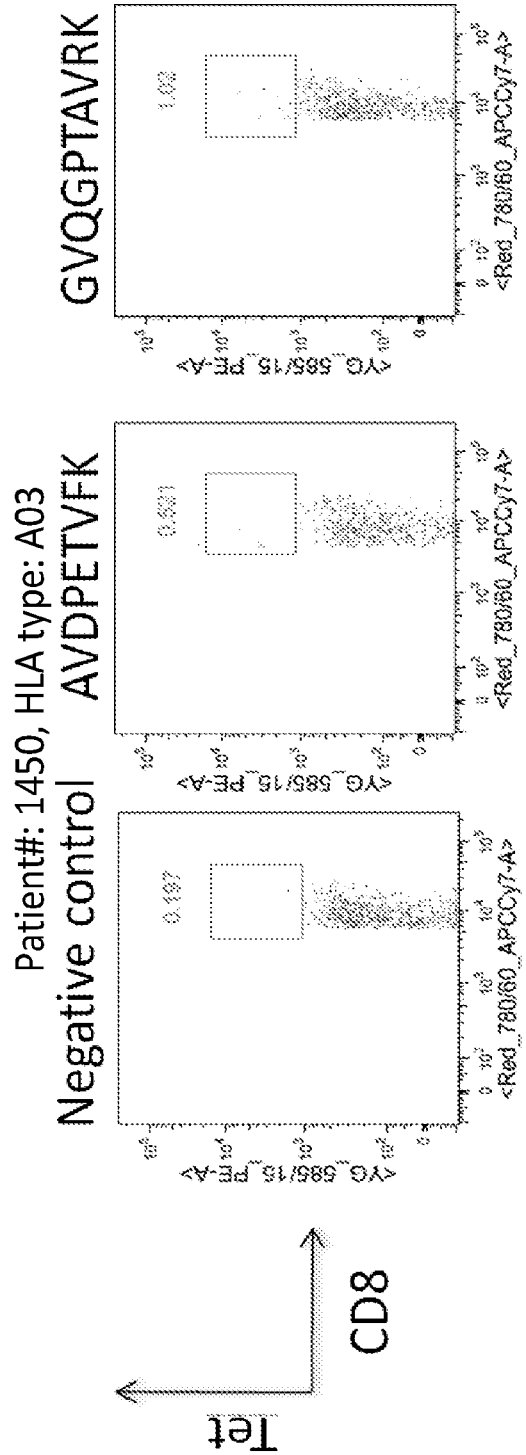
FIG. 9

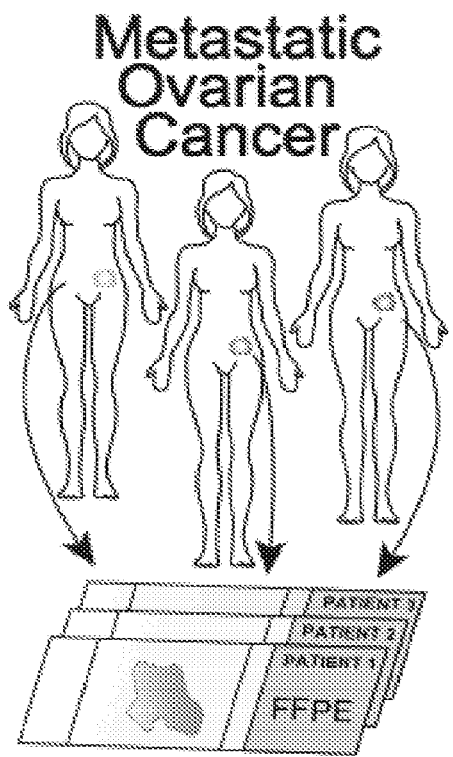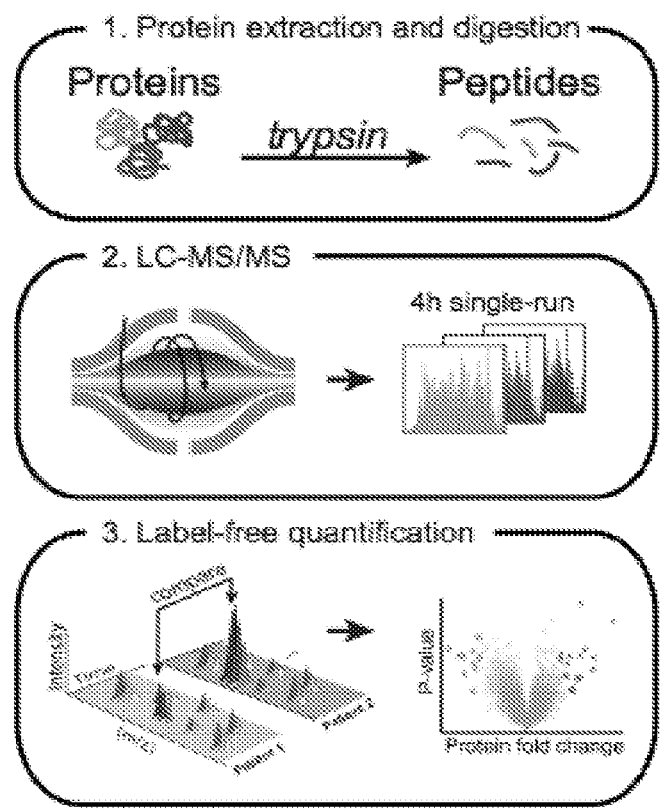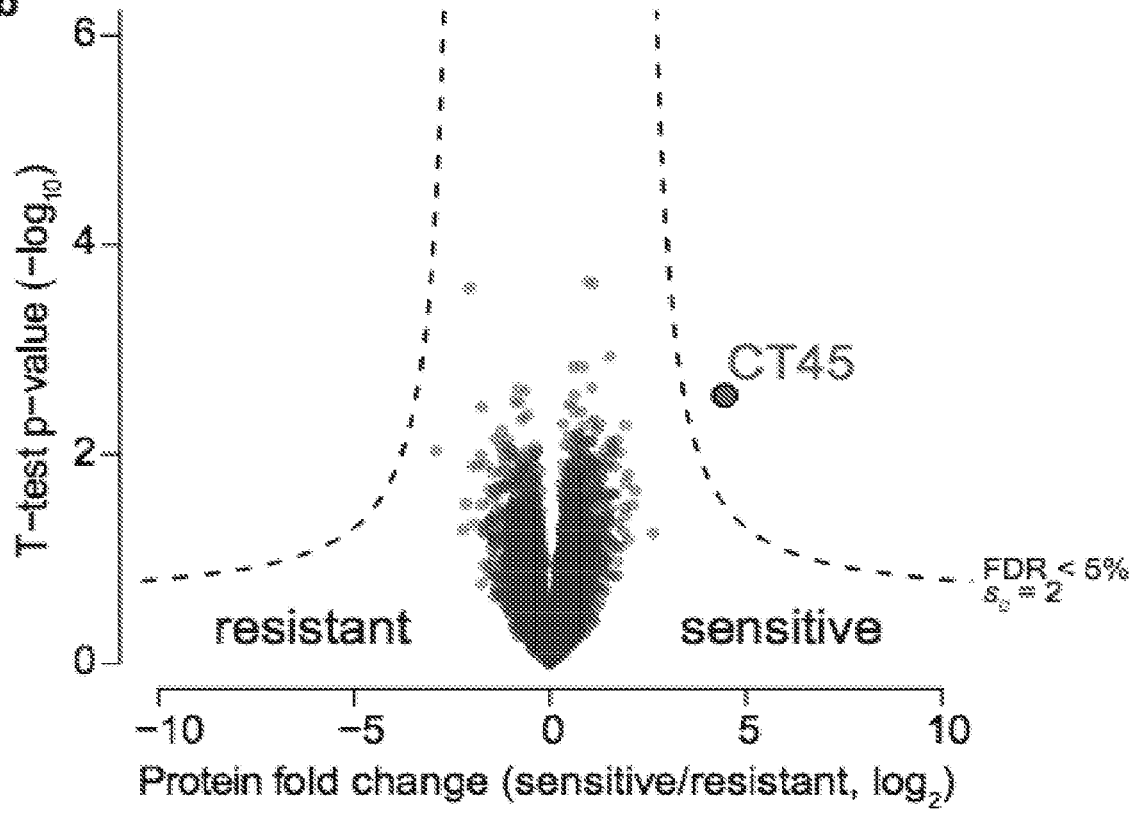
FIG.10A-B

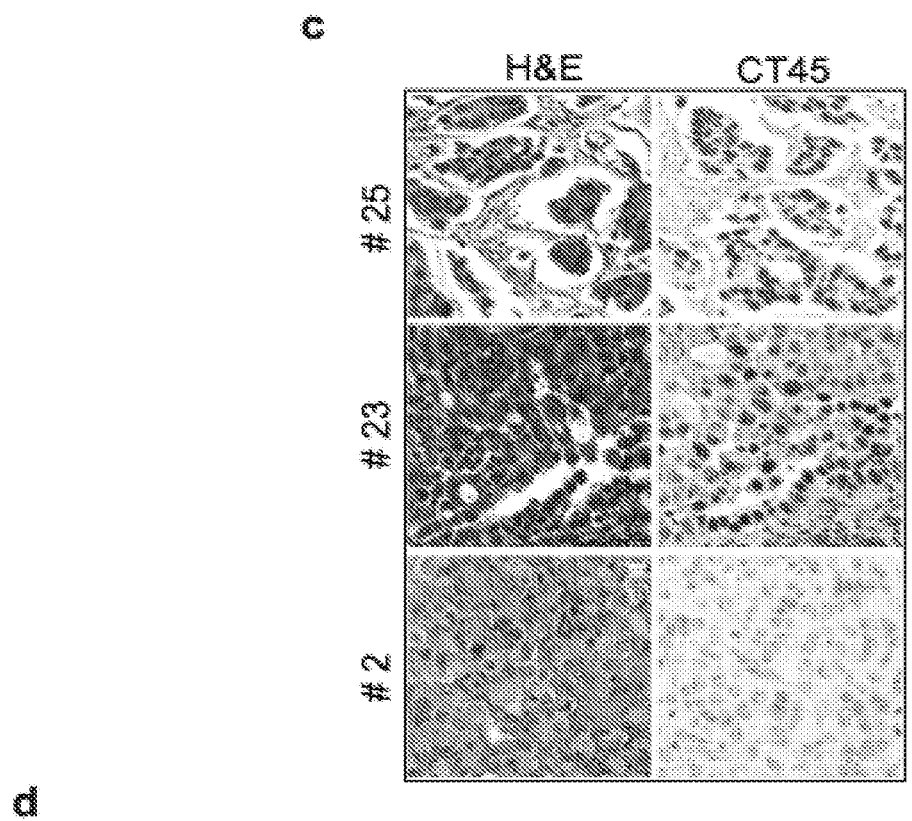
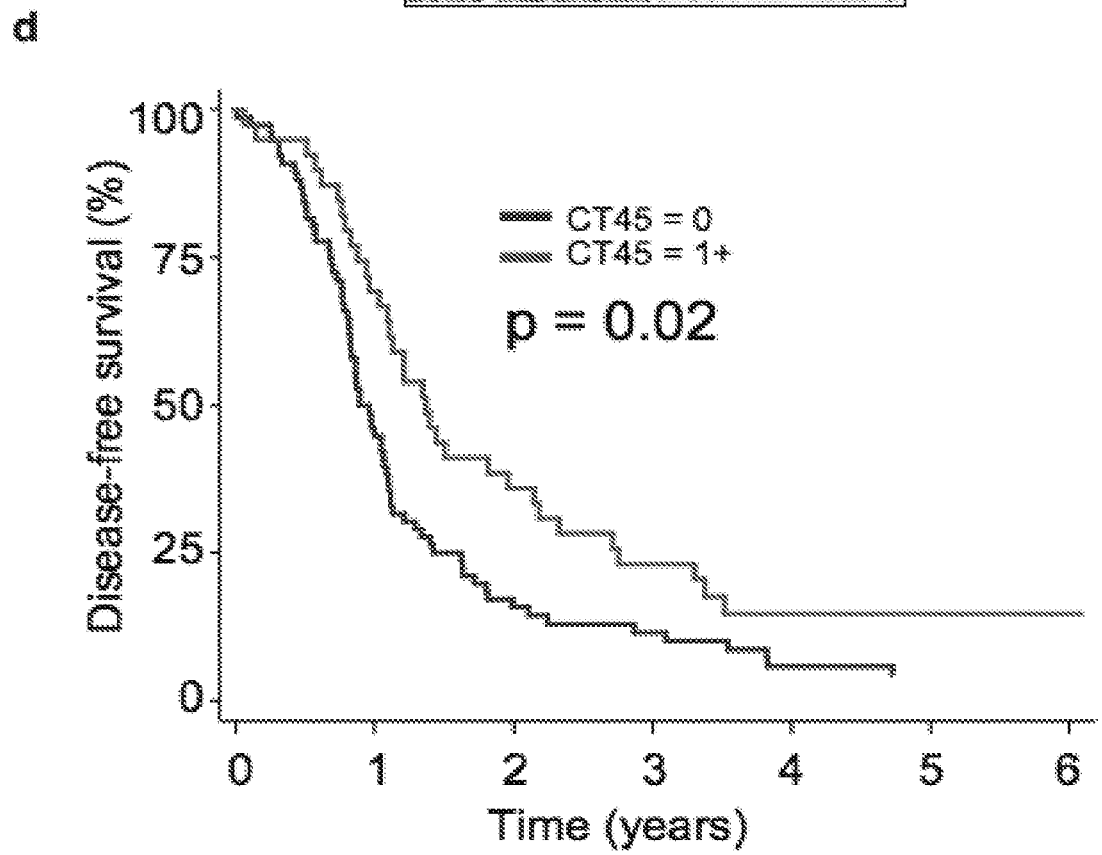
FIG. 10C-D

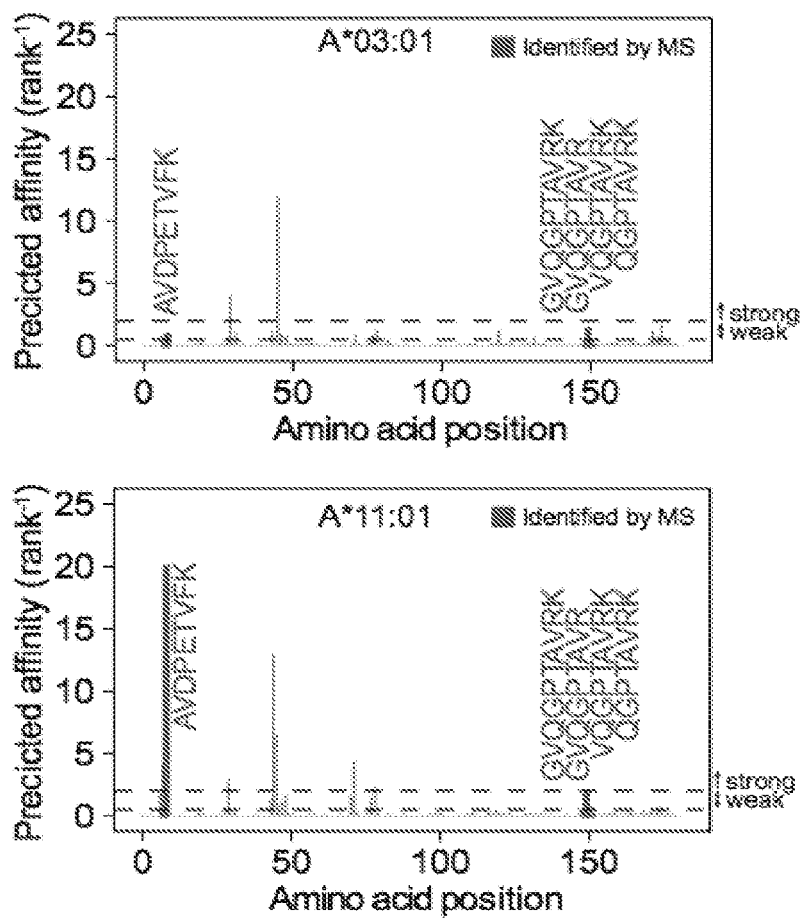
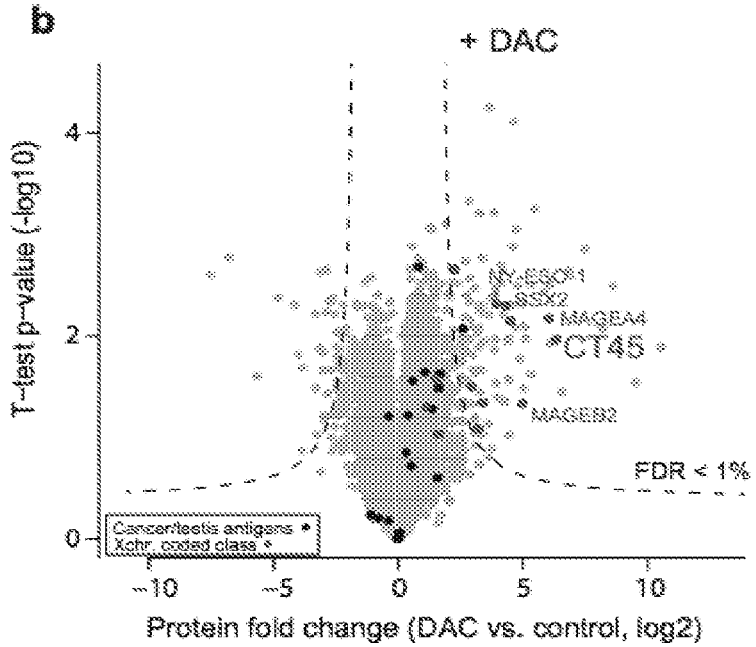
FIG. 11A-B

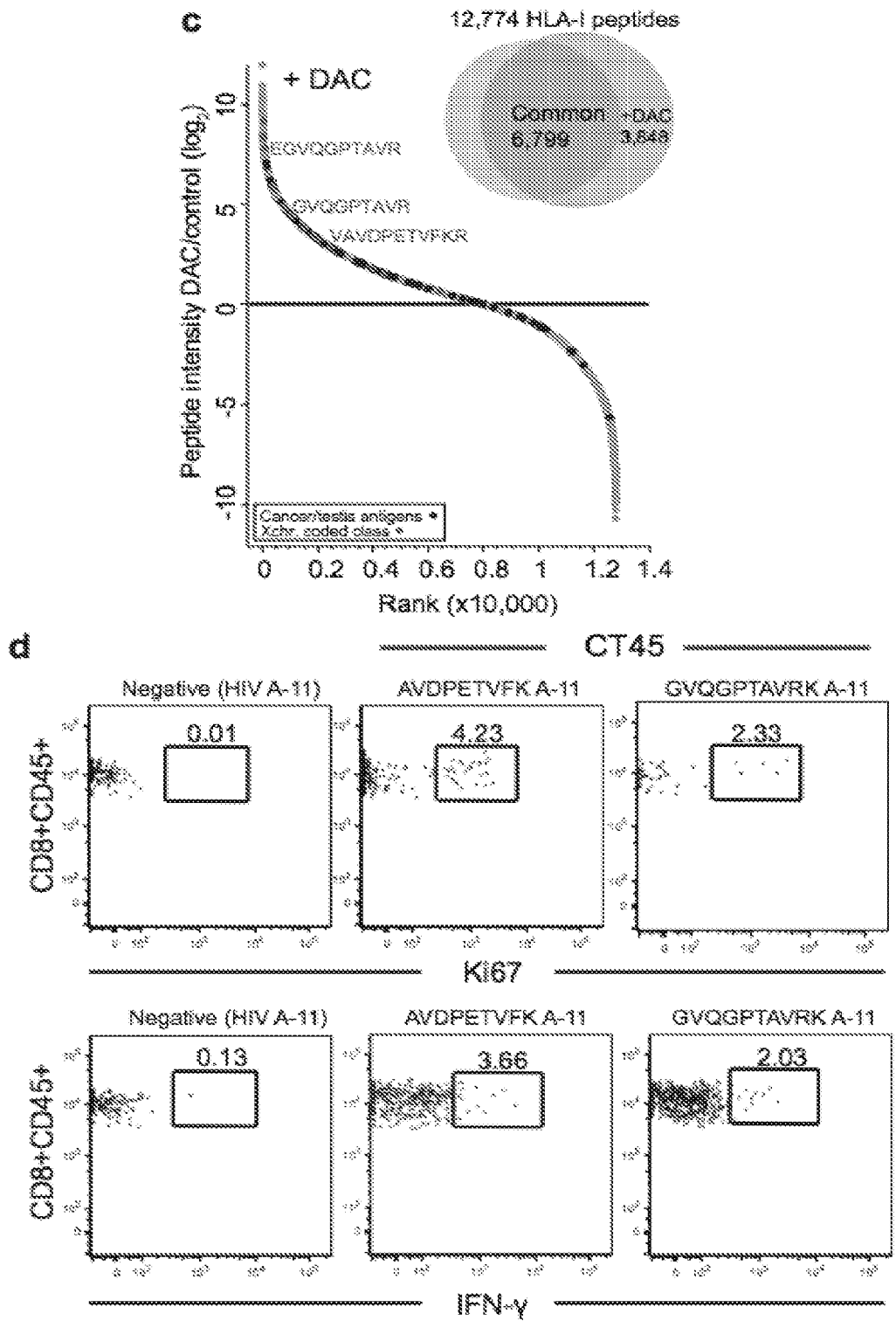
FIG. 11C-D

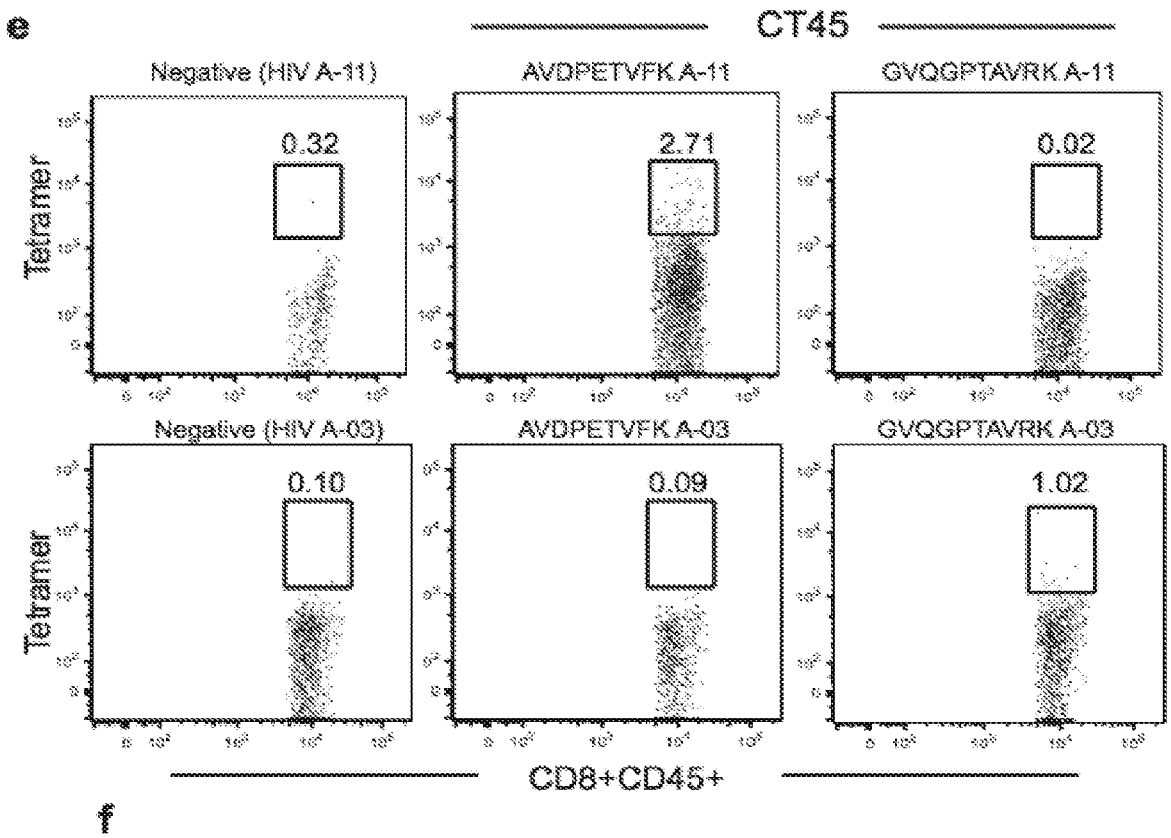
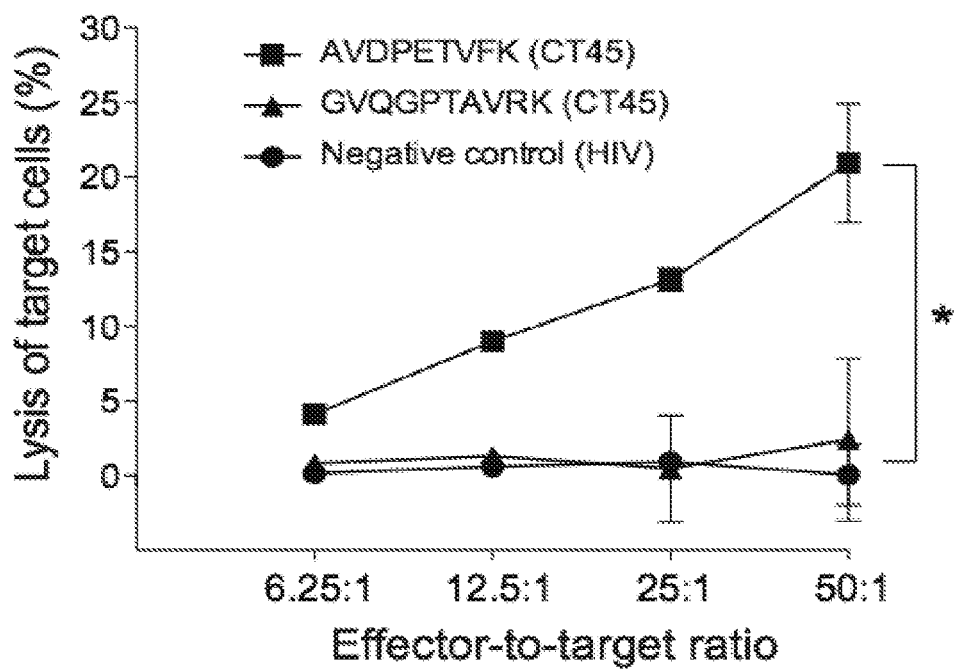
FIG. 11E-F

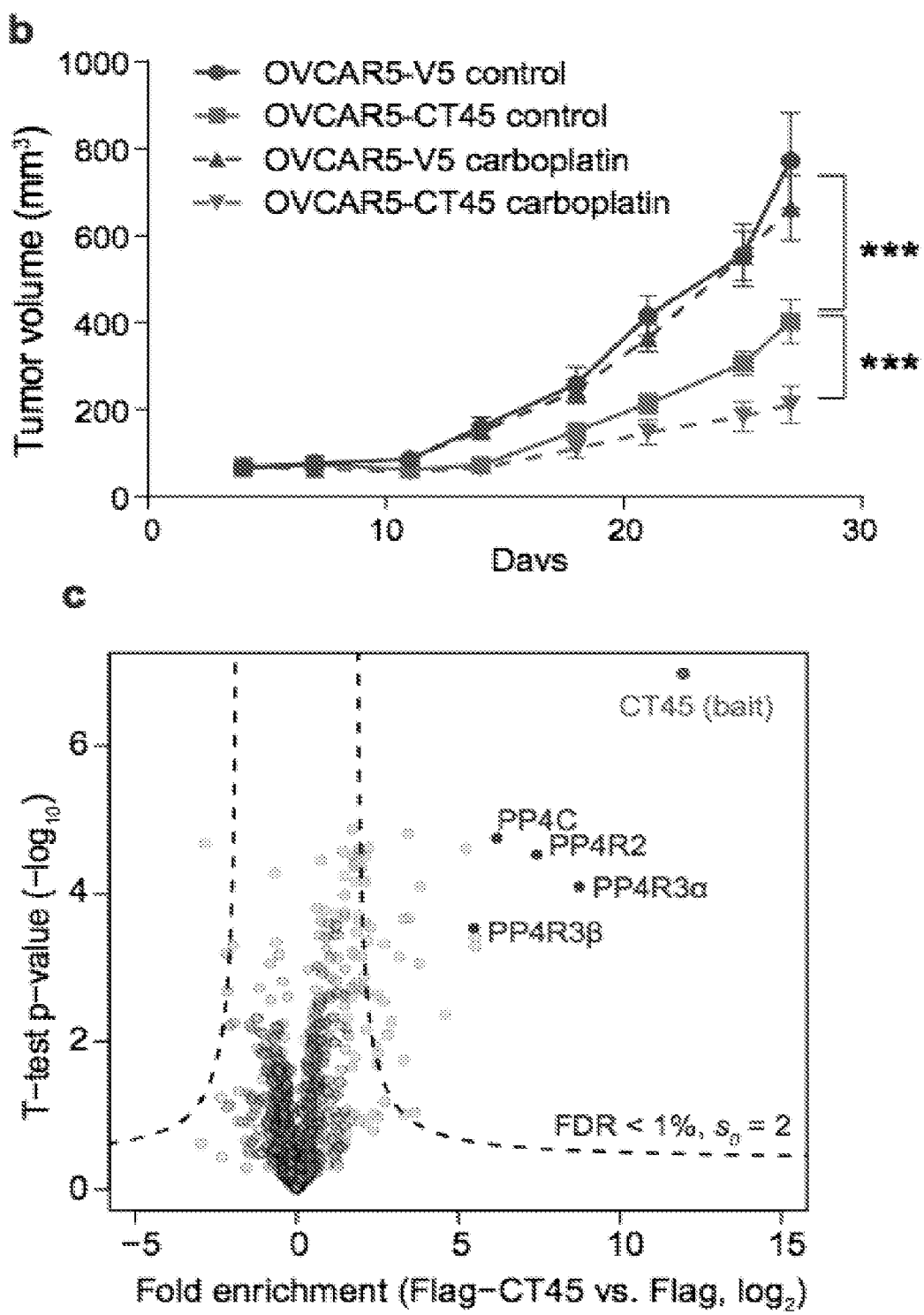
FIG. 12B-C

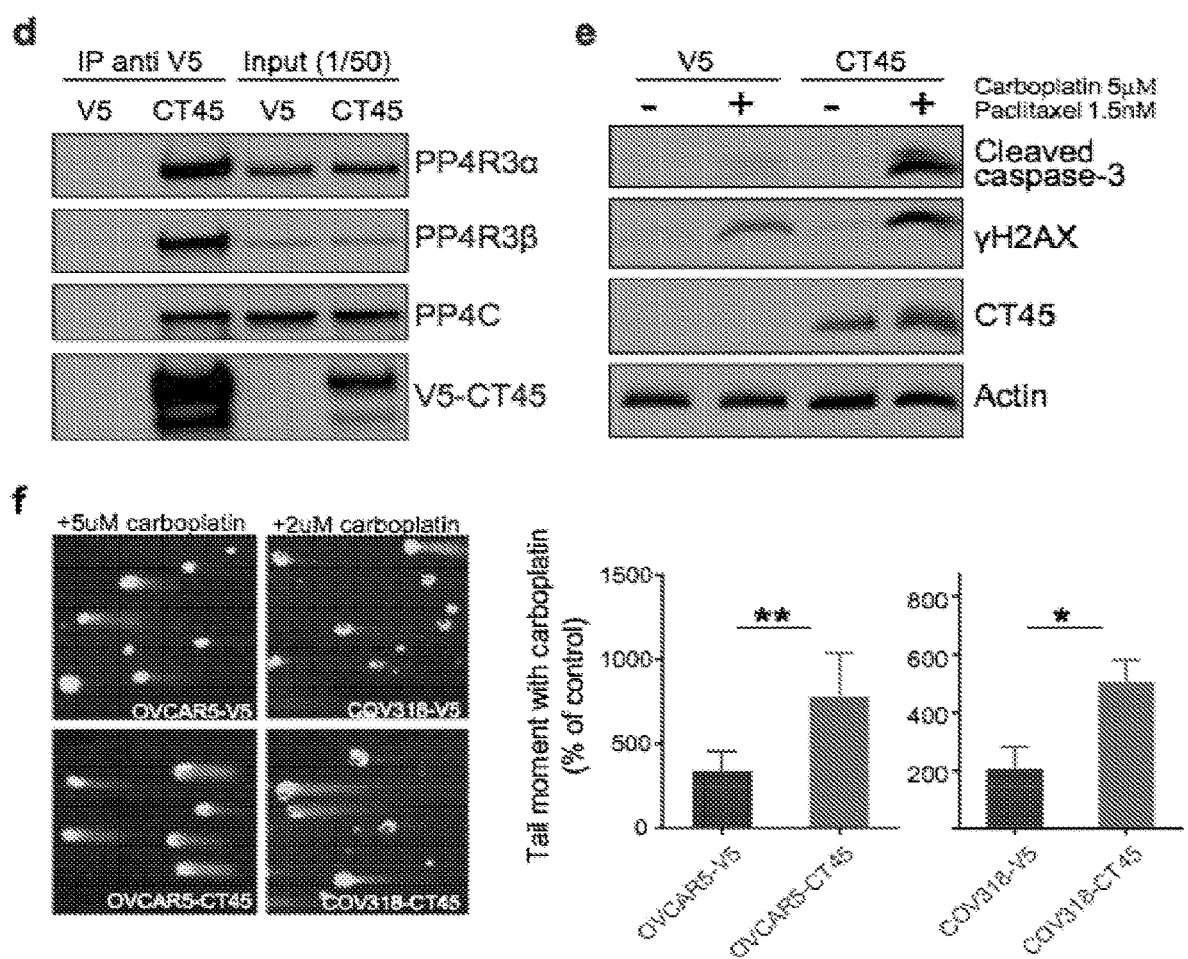
FIG. 12D-F

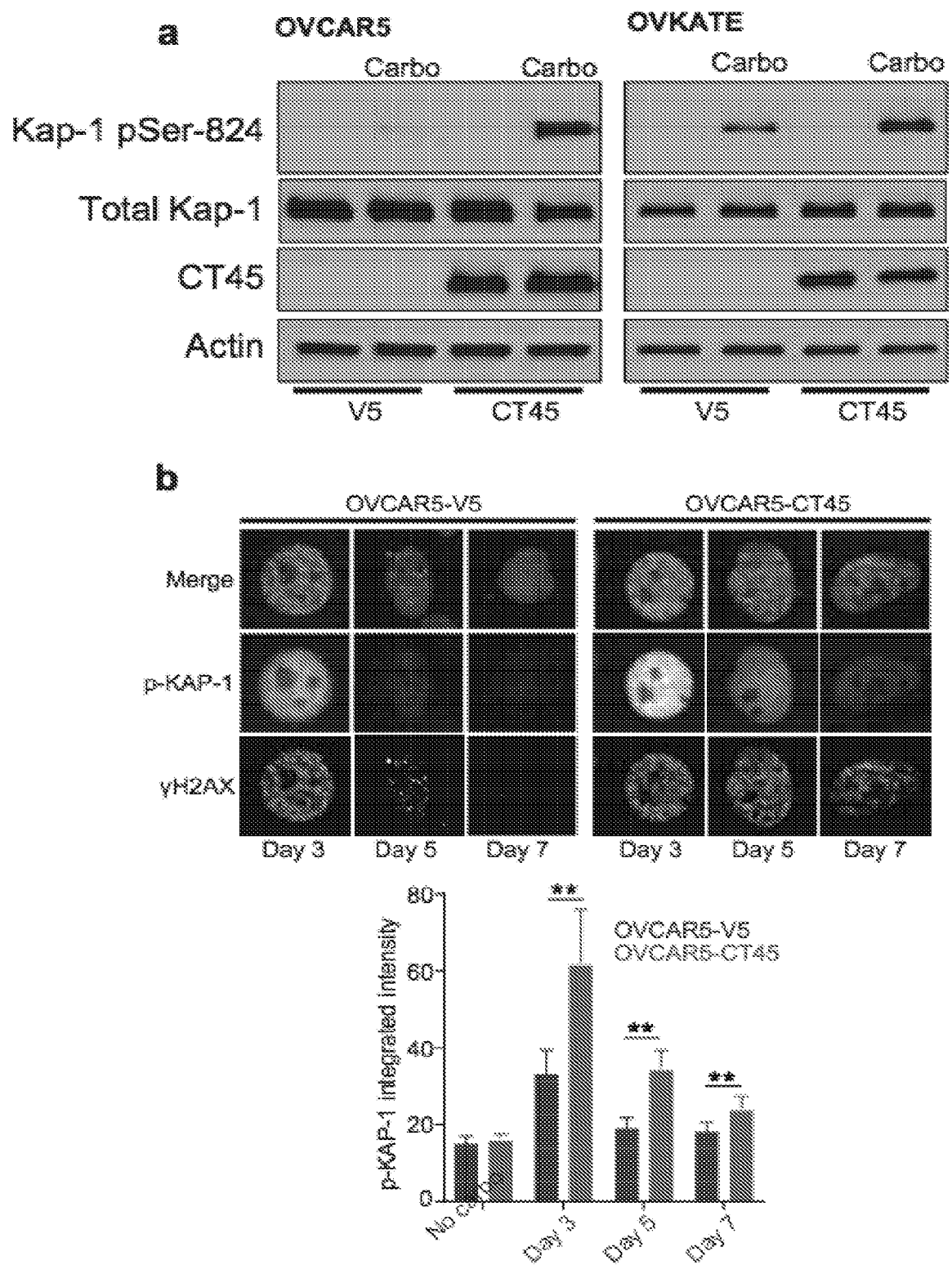
FIG. 13A-B

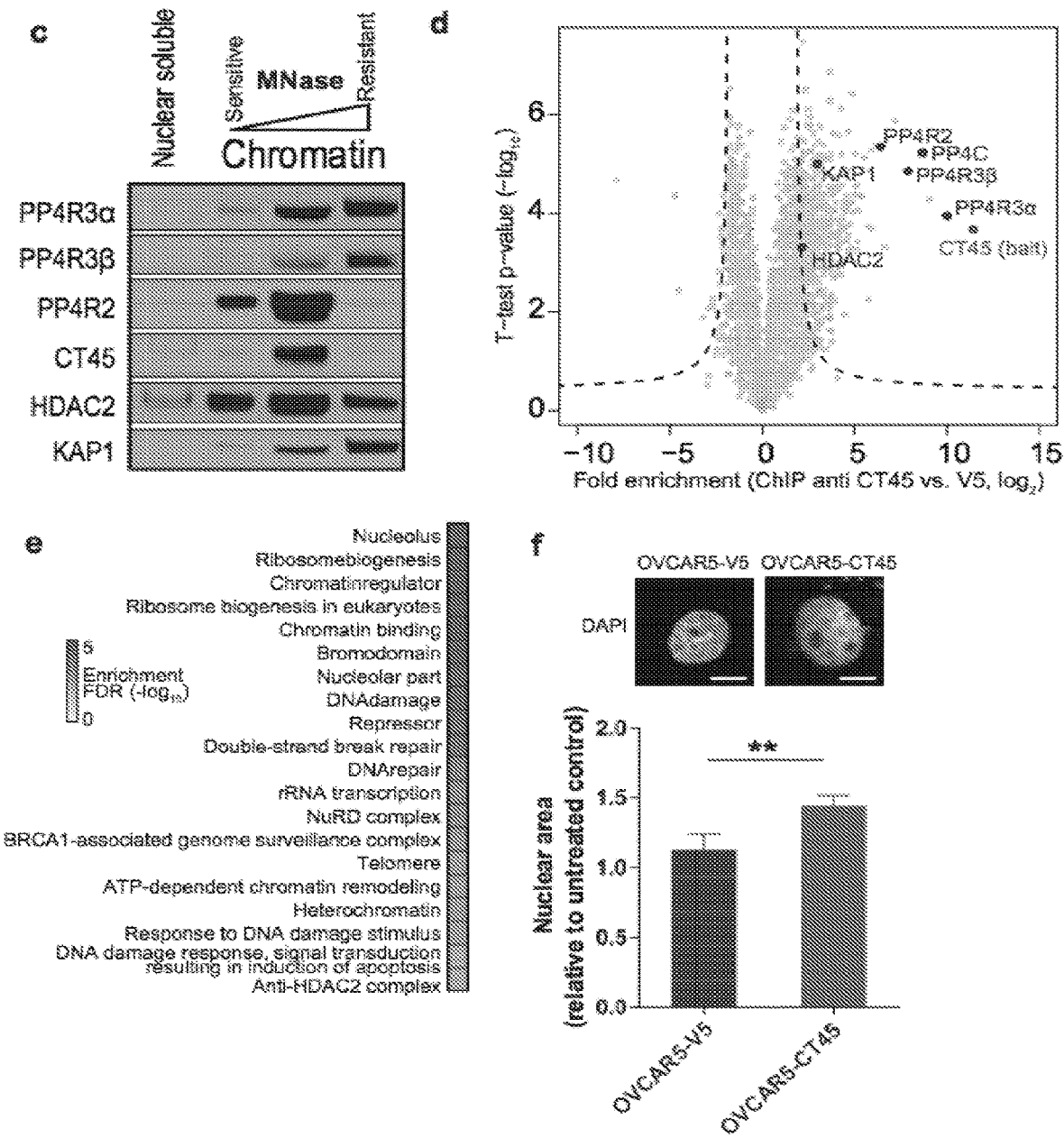
FIG. 13C-F

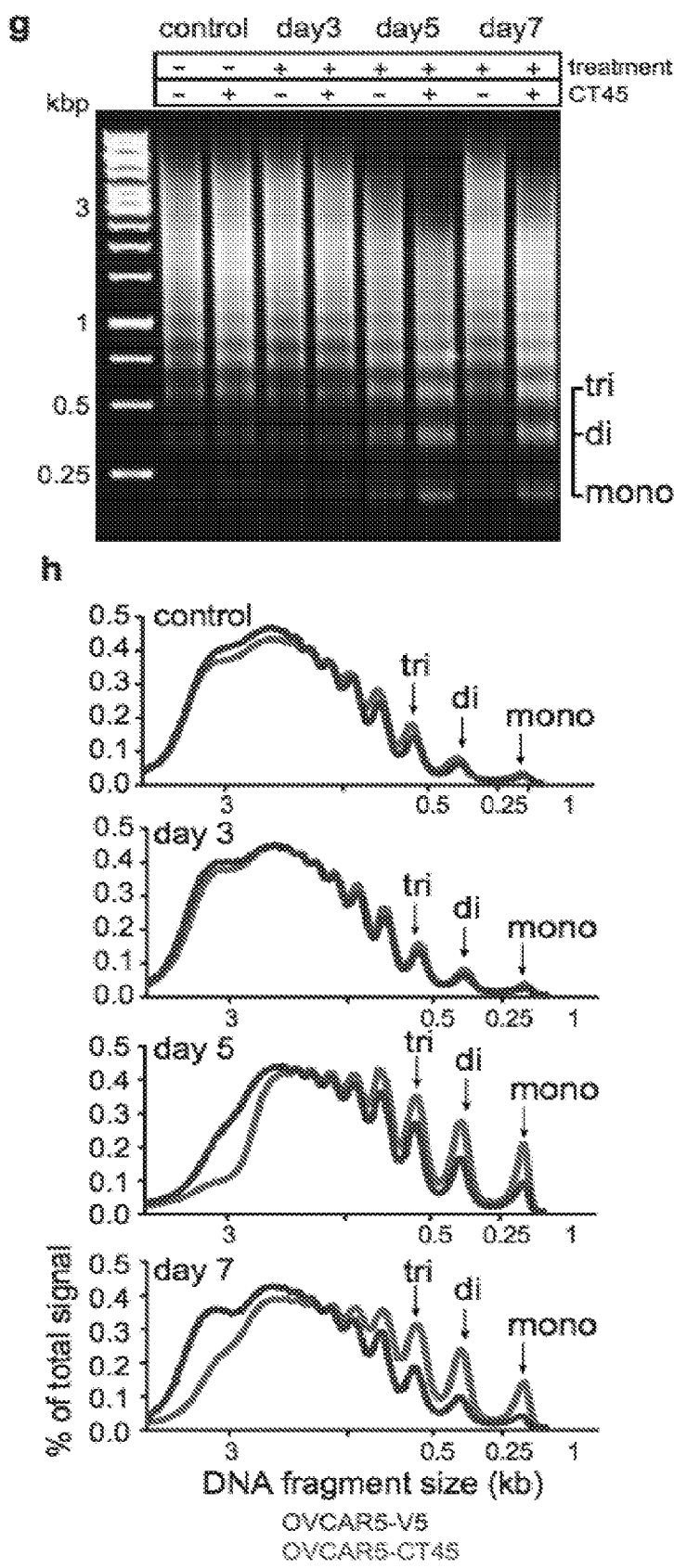
FIG. 13G-H

|  | Chemotherapy Status | | | | P value | All cases |
|---|---|---|---|---|---|---|
|  | Resistant | | Sensitive | | | |
|  | No. | % | No. | % | | |
| Stage | | | | | 1.00 | |
| 3 | 8 | 72.7 | 10 | 71.4 | | 18 |
| 4 | 3 | 27.3 | 4 | 28.6 | | 7 |
| Primary Site | | | | | 0.0850 | |
| Fallopian Tube | 4 | 36.4 | 6 | 42.8 | | 10 |
| Ovary | 7 | 63.6 | 4 | 28.6 | | 11 |
| Peritoneum | 0 | 0 | 4 | 28.6 | | 4 |
| Residual Disease | | | | | 0.0531 | |
| Larger than 1 cm | 8 | 72.7 | 5 | 35.7 | | 13 |
| Smaller than 1 cm | 2 | 18.2 | 9 | 64.3 | | 11 |
| Unknown | 1 | 9.1 | 0 | 0 | | 1 |
| Grade | | | | | 0.4867 | |
| 2 | 0 | 0 | 2 | 14.3 | | 2 |
| 3 | 11 | 100 | 12 | 85.7 | | 23 |
| Chemo Type | | | | | | |
| Adjuvant/1st line | 11 | 100 | 14 | 100 | | |
| Chemo Class | | | | | 1.00 | |
| Platinum only | 0 | 0 | 1 | 7.1 | | 1 |
| Taxane/Platinum | 11 | 100 | 13 | 92.9 | | 24 |
| Progression free survival | | | | | | |
| Median days (range) | 190 (113-391) | | 1160.5 (552-3229) | | < 0.0001 | |
| Overall survival | | | | | | |
| Median days (range) | 448 (228-1489) | | 1550.5 (967-3229) | | <0.0001 | |
| Age | | | | | | |
| Mean age (range) | 60.0 (47-78) | | 67.1 (51-86) | | 0.0908 | |

FIG. 14A

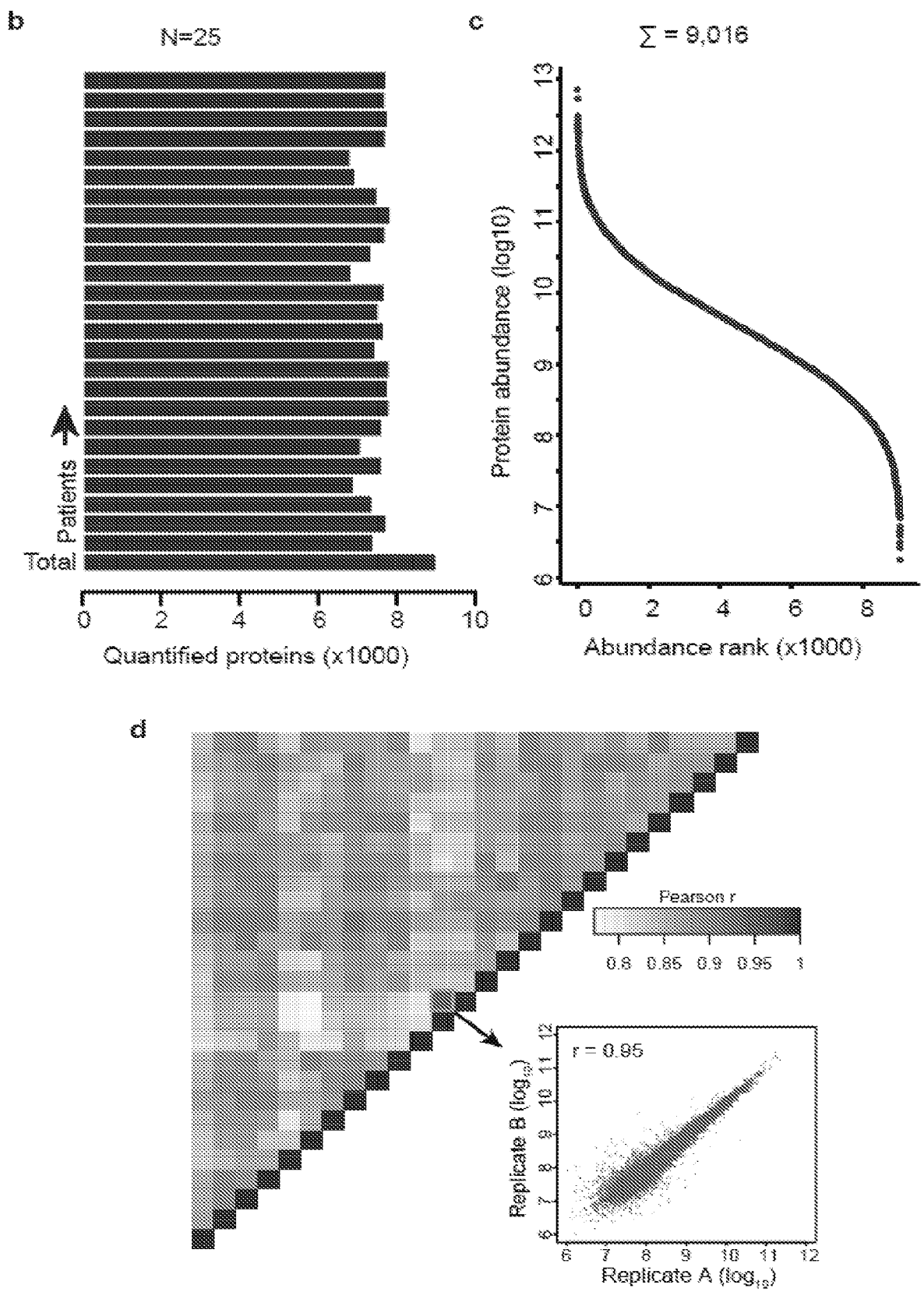
FIG. 14B-D

|  | CT45 Status | | | | |
|---|---|---|---|---|---|
|  | 0 (N=82) | | 1+ (N=42) | | |
|  | No. | % | No. | % | P value |
| Stage | | | | | 0.72 |
| 3 | 56 | 68.29 | 30 | 71.43 | |
| 4 | 26 | 31.71 | 12 | 28.57 | |
| | | | | | |
| Primary Site | | | | | 0.41 |
| Fallopian Tube | 10 | 12.2 | 9 | 21.43 | |
| Ovary | 62 | 75.61 | 29 | 69.05 | |
| Peritoneum | 10 | 12.2 | 4 | 9.52 | |
| | | | | | |
| Residual Disease | | | | | 0.10 |
| Larger than 1 cm | 47 | 57.32 | 17 | 40.48 | |
| Smaller than 1 cm | 34 | 41.46 | 25 | 59.52 | |
| Unknown | 1 | 1.22 | 0 | 0 | |
| | | | | | |
| Grade | | | | | 0.59 |
| 1 | 1 | 1.22 | 0 | 0 | |
| 2 | 22 | 26.83 | 8 | 19.05 | |
| 3 | 59 | 71.95 | 34 | 80.95 | |
| | | | | | |
| Chemo Type | | | | | 0.67 |
| Adjuvant/1st line | 64 | 78.05 | 35 | 83.33 | |
| Neoadjuvant | 13 | 15.85 | 4 | 9.52 | |
| None | 5 | 6.1 | 3 | 7.14 | |
| | | | | | |
| Chemo Class | | | | | 0.19 |
| Other | 4 | 4.88 | 6 | 14.29 | |
| Taxane/Platinum | 73 | 89.02 | 33 | 78.57 | |
| None | 5 | 6.1 | 3 | 7.14 | |
| | | | | | |
| Chemoresistance | | | | | 0.005 |
| resistant | 46 | 56.1 | 10 | 23.81 | |
| intermediate | 11 | 13.41 | 9 | 21.43 | |
| sensitive | 19 | 23.17 | 18 | 42.86 | |
| N/A | 6 | 7.32 | 5 | 11.9 | |
| | | | | | |
| Mean age (range) | 62 | (33-94) | 58 | (33-82) | 0.13 |

FIG. 16A

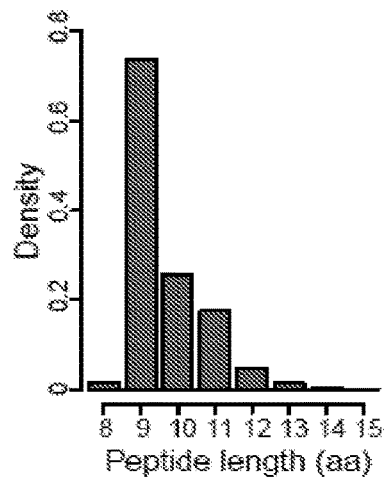

FIG. 17C

>sp|Q5HYN5|CT451_HUMAN Cancer/testis antigen family 45
member A1 OS=Homo sapiens GN=CT45A1 PE=2 SV=1
MTDKTEKV<u>AVDPETVFK</u>RPRECDSPSYQKRQRMALLARKQGAG
DSLIAGSAMSKAKKLMTGHAIPPSQLDSQIDDFTGFSKDRMMQKPG
SNAPVGGNVTSSFSGDDLECRETASSPKSQREINADIKRKLVKELR
CVGQKYEKIFEMLE<u>GVQGPTAVRKR</u>FFESIIKEAARCMRRDFVKH
LKKKLKRMI

→ GVQGPTAVRKR
  VQGPTAVRKR
  GVQGPTAVRK
  QGPTAVRKR

FIG. 17D

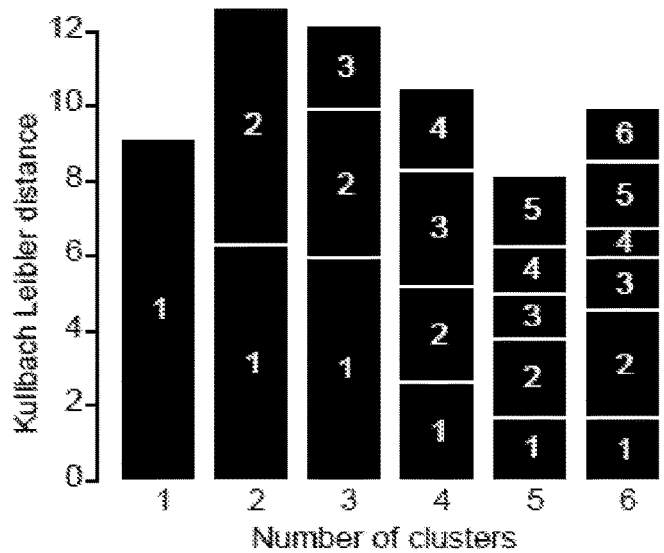

FIG. 17E

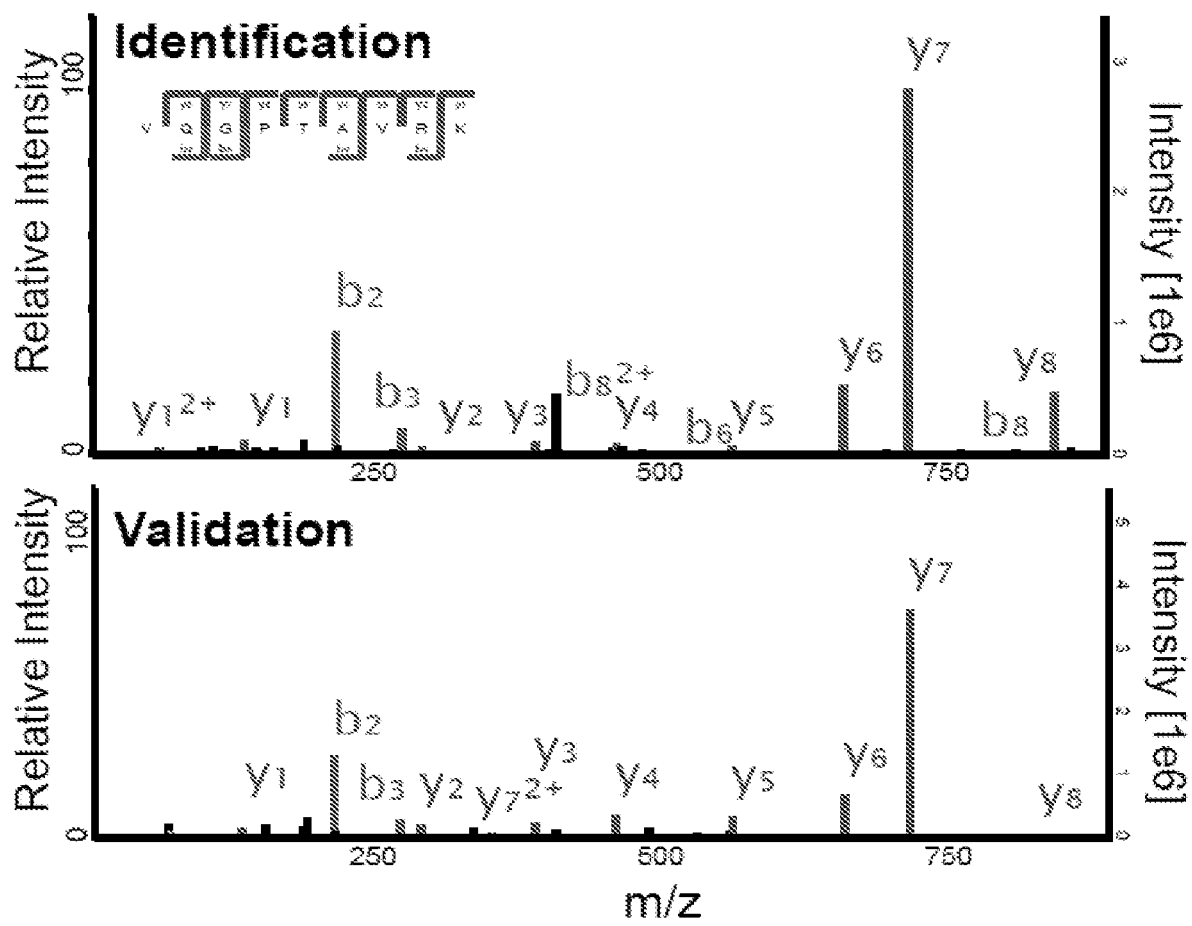
FIG. 17H
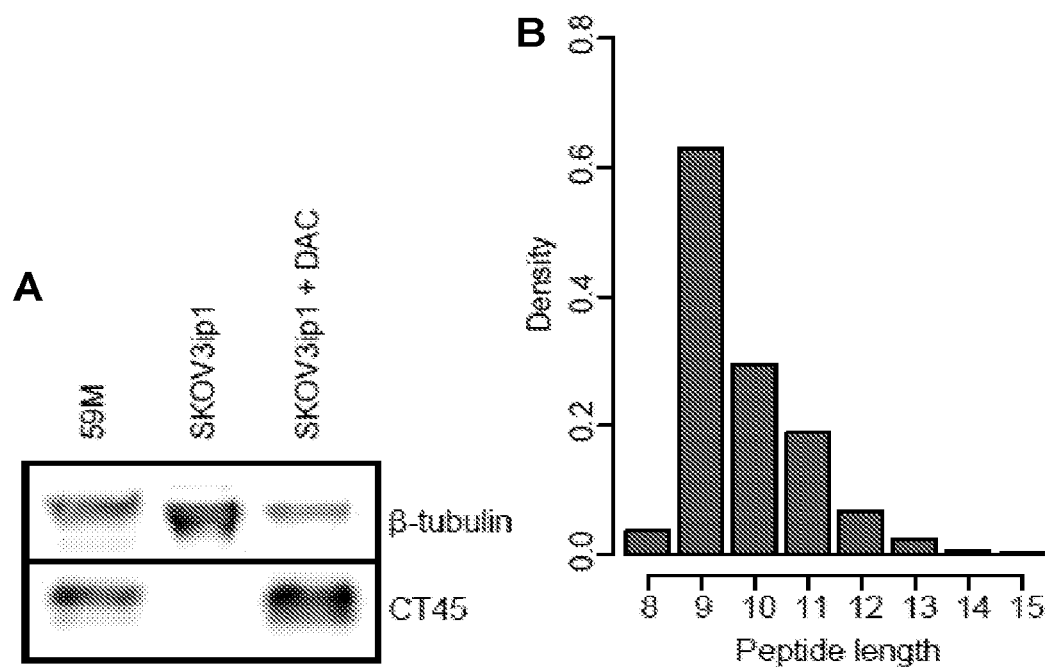
FIG. 18A-B

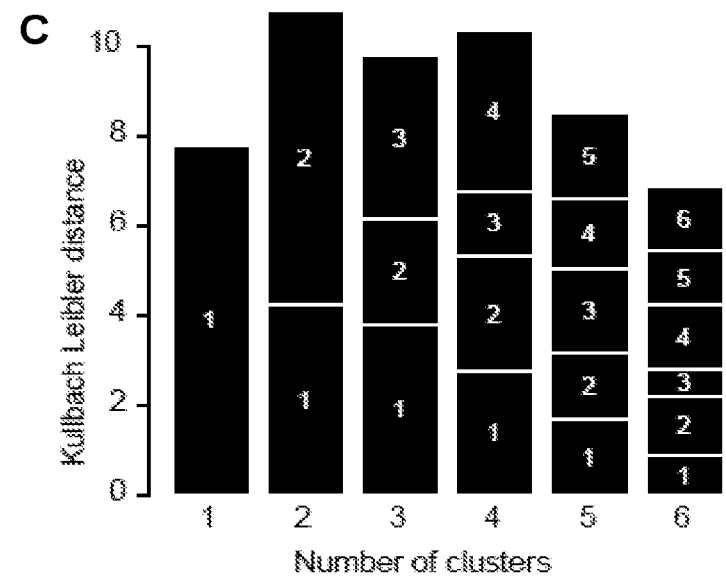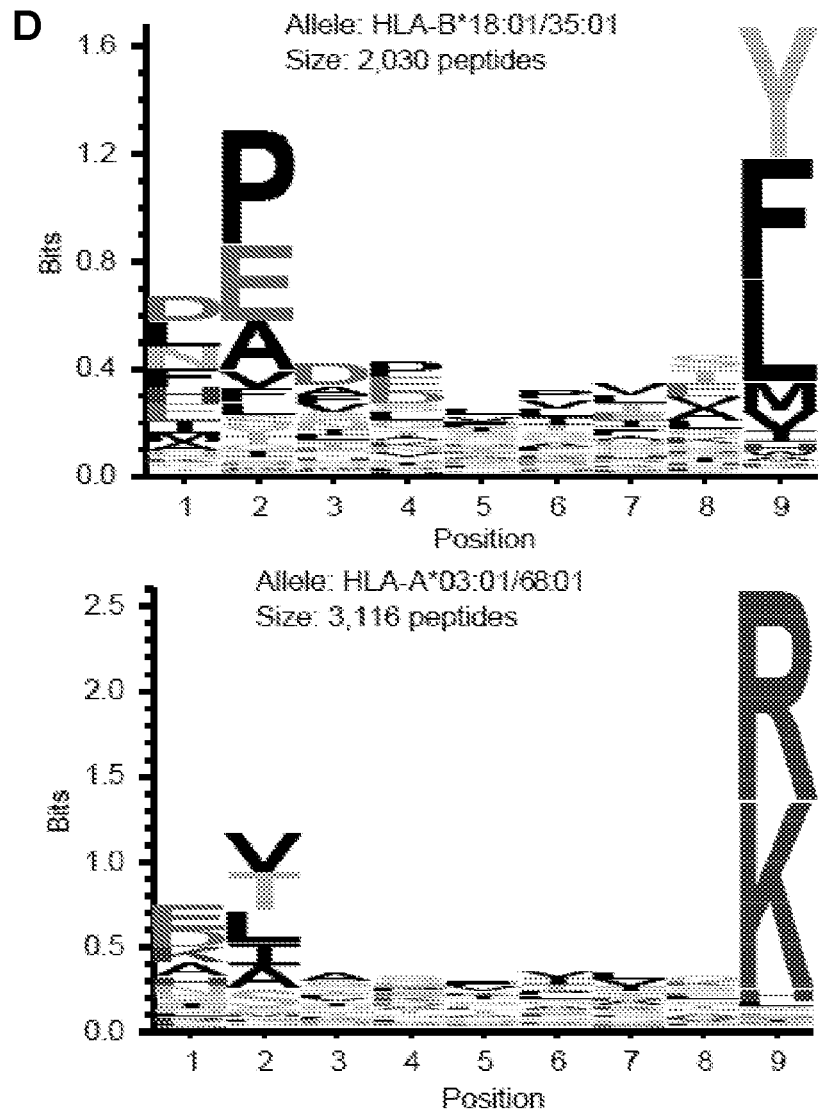
FIG. 18C-D

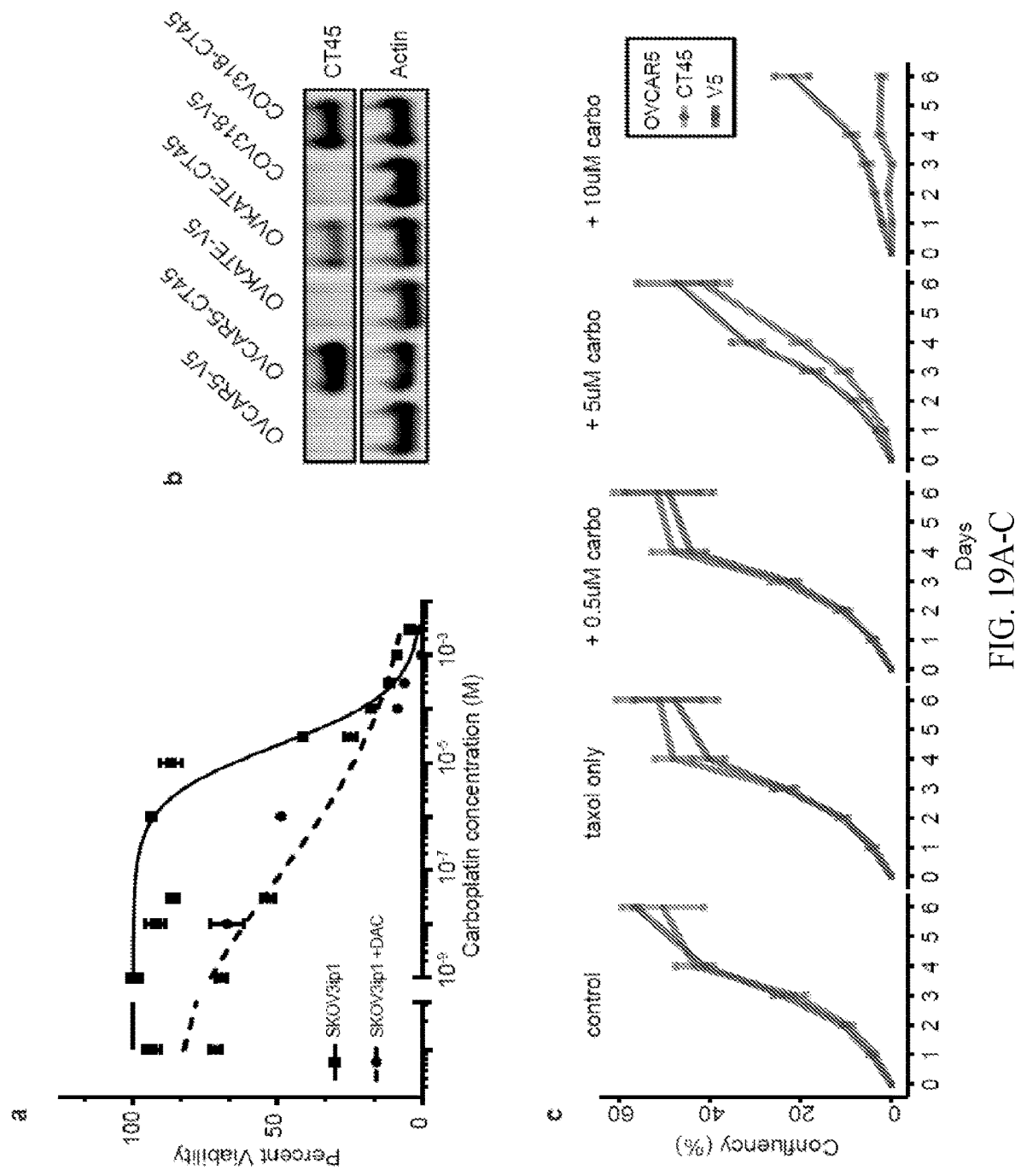
FIG. 19A-C

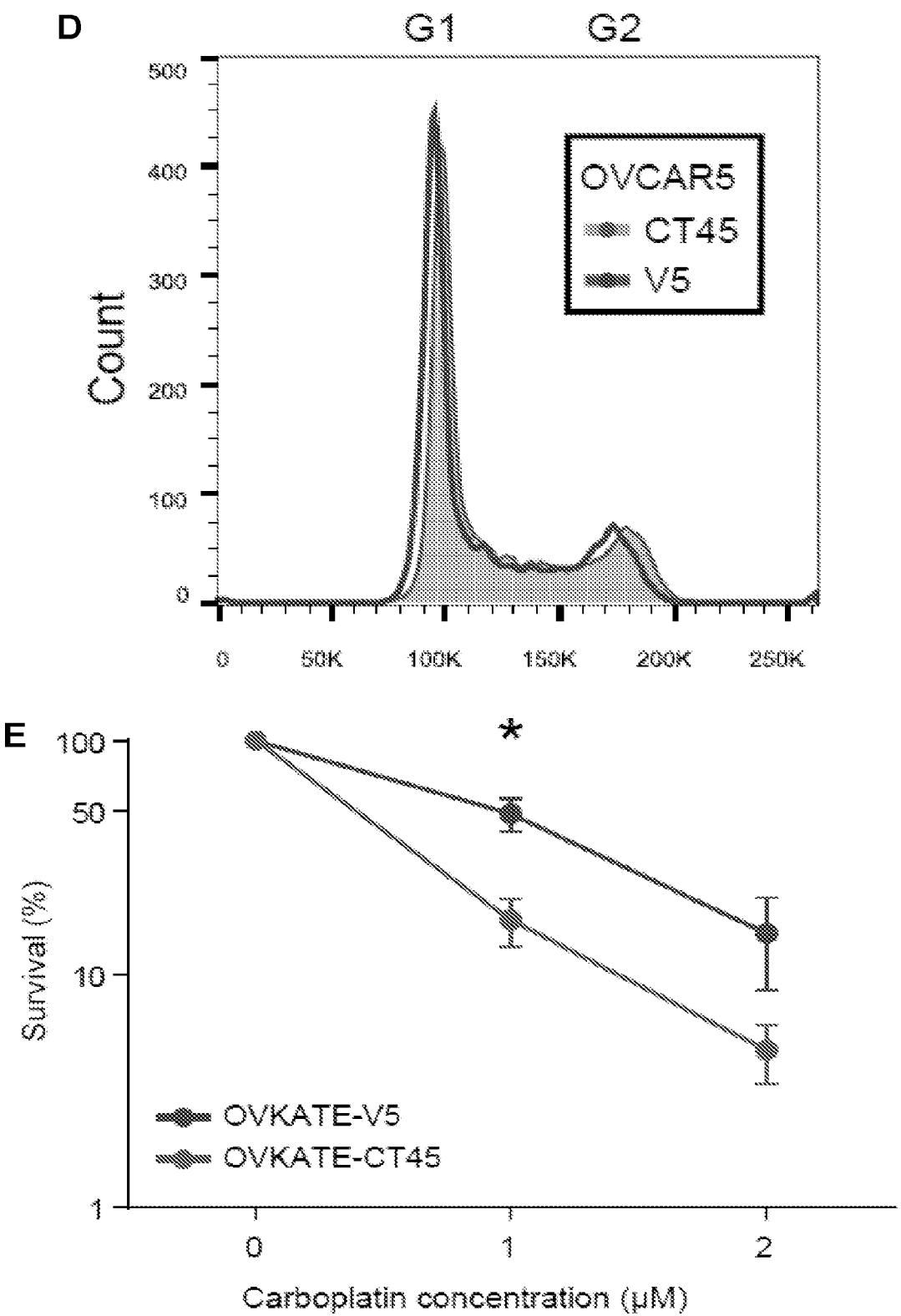
FIG. 19D-E

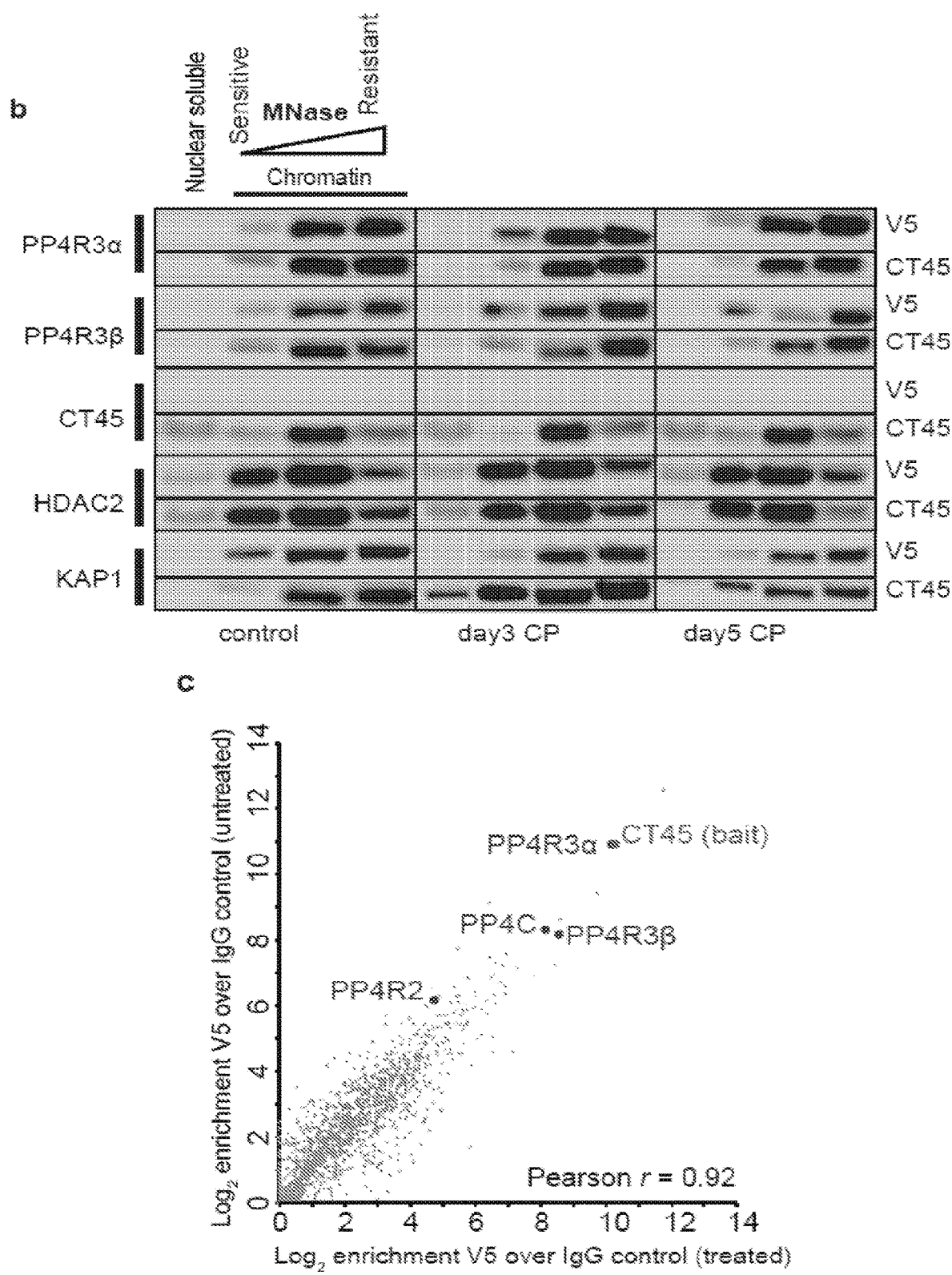
FIG. 20B-C

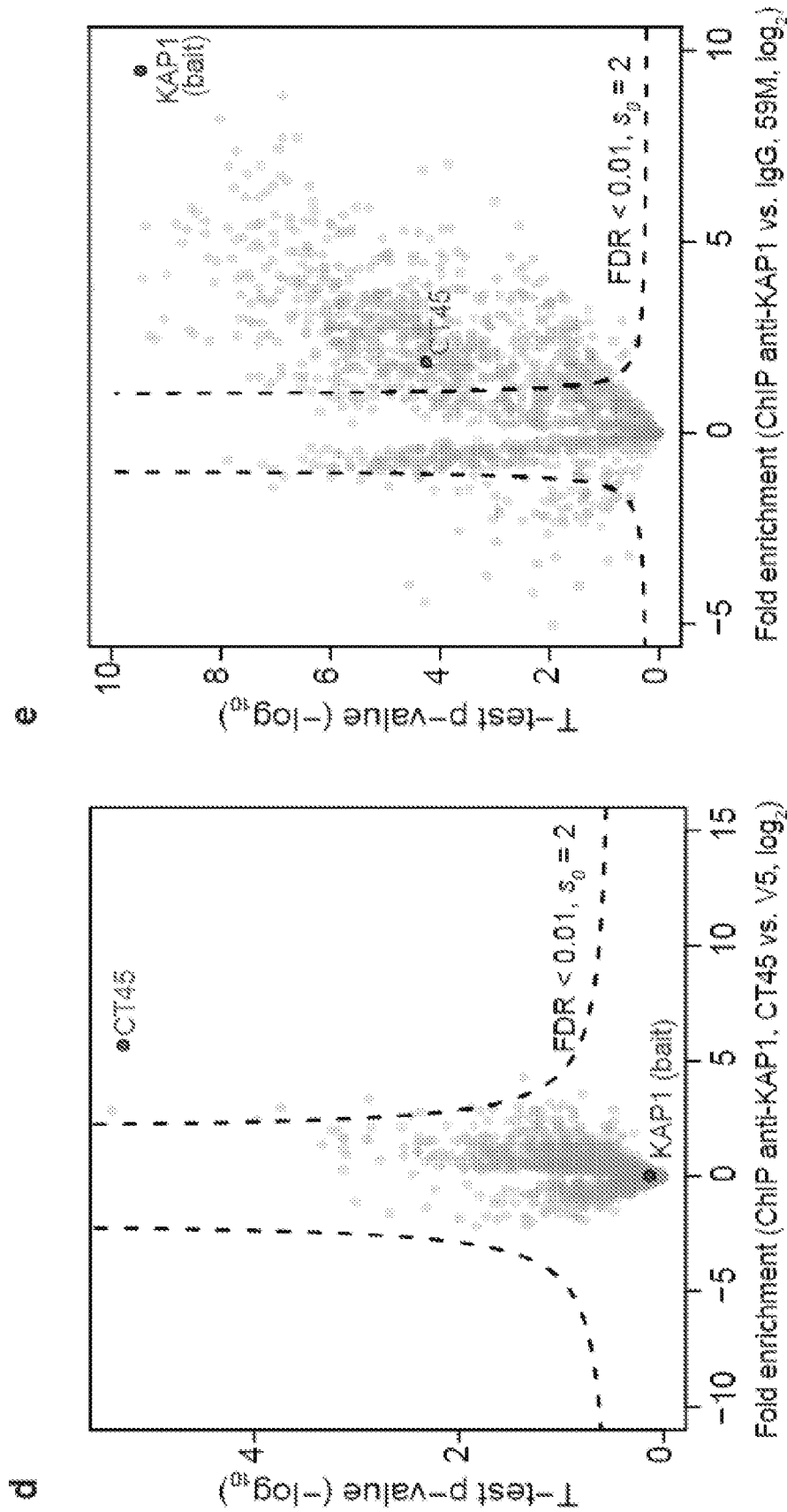
FIG. 20D-E

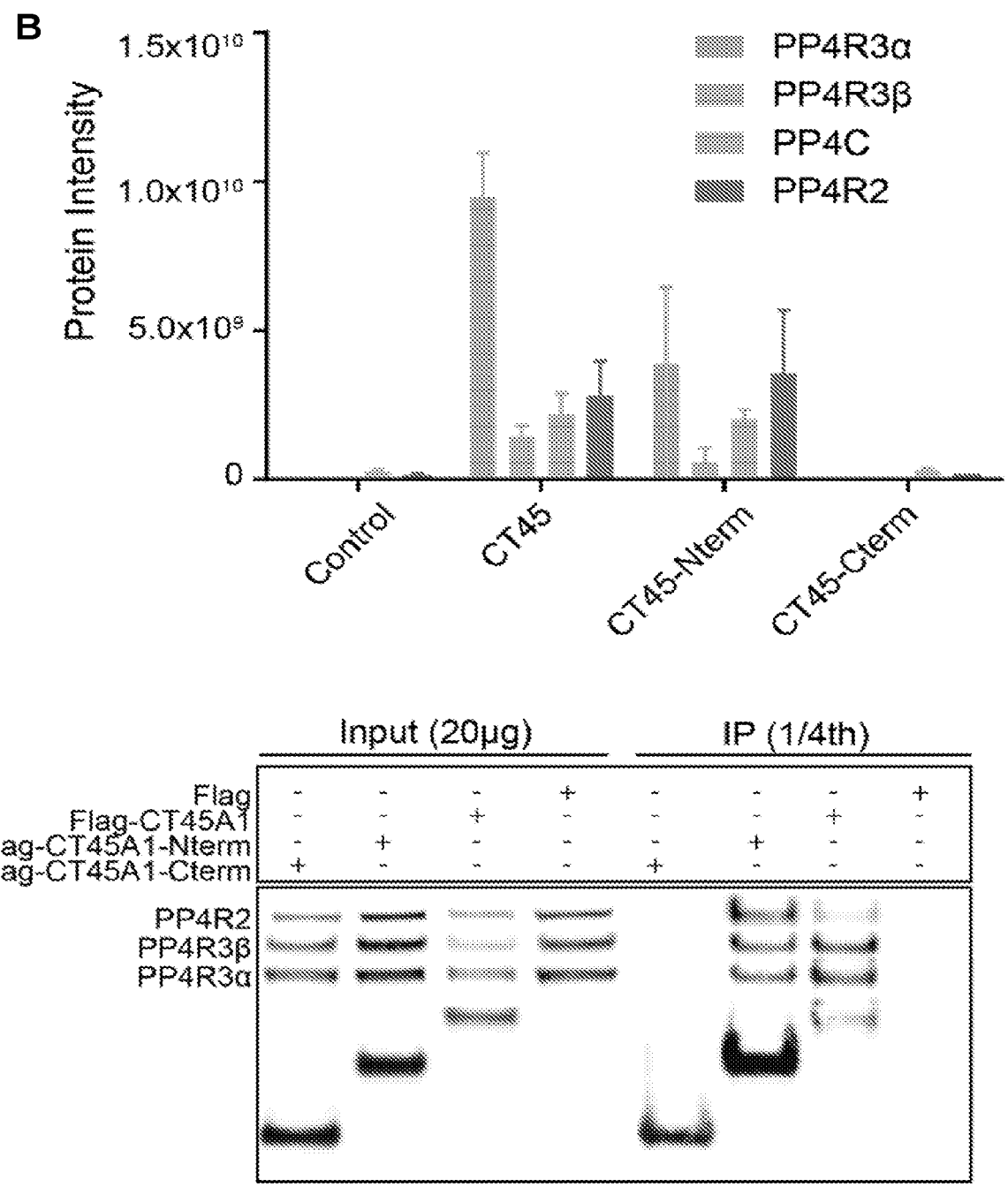
FIG. 24B-C

SEQUENCE LISTING

<160> NUMBER OF SEQ ID NOS: 39

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 1

Ala Val Asp Pro Glu Thr Val Phe Lys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 2

Gly Val Gln Gly Pro Thr Ala Val Arg
1               5

<210> SEQ ID NO 3
<211> LENGTH: 10
<212> TYPE: PRT

<213> ORGANISM: Artificial Sequence
<220> FEATURE:
<223> OTHER INFORMATION: Synthetic Peptide

<400> SEQUENCE: 3

Gly Val Gln Gly Pro Thr Ala Val Arg Lys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 4

Val Gln Gly Pro Thr Ala Val Arg Lys
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 5

Gln Gly Pro Thr Ala Val Arg Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 6

Gln Gly Pro Thr Ala Val Arg
1               5

<210> SEQ ID NO 7
<211> LENGTH: 189
<212> TYPE: PRT
<213> ORGANISM: Artificial Sequence
<220> FEATURE:
<223> OTHER INFORMATION: Synthetic Peptide

<400> SEQUENCE: 7

Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
                20                  25                  30

Met Ala Leu Leu Ala Arg Lys Gln Gly Ala Gly Asp Ser Leu Ile Ala
            35                  40                  45

Gly Ser Ala Met Ser Lys Glu Lys Lys Leu Met Thr Gly His Ala Ile
        50                  55                  60

Pro Pro Ser Gln Leu Asp Ser Gln Ile Asp Asp Phe Thr Gly Phe Ser
65                  70                  75                  80

Lys Asp Gly Met Met Gln Lys Pro Gly Ser Asn Ala Pro Val Gly Gly
                85                  90                  95

Asn Val Thr Ser Ser Phe Ser Gly Asp Asp Leu Glu Cys Arg Glu Thr
                100                 105                 110

```
Ala Ser Ser Pro Lys Ser Gln Arg Glu Ile Asn Ala Asp Ile Lys Arg
            115                 120                 125

Lys Leu Val Lys Glu Leu Arg Cys Val Gly Gln Lys Tyr Glu Lys Ile
        130                 135                 140

Phe Glu Met Leu Glu Gly Val Gln Gly Pro Thr Ala Val Arg Lys Arg
145                 150                 155                 160

Phe Phe Glu Ser Ile Ile Lys Glu Ala Ala Arg Cys Met Arg Arg Asp
                165                 170                 175

Phe Val Lys His Leu Lys Lys Lys Leu Lys Arg Met Ile
            180                 185

<210> SEQ ID NO 8
<211> LENGTH: 189
<212> TYPE: PRT
<213> ORGANISM: Artificial Sequence
<220> FEATURE:
<223> OTHER INFORMATION: Synthetic Peptide

<400> SEQUENCE: 8

Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
            20                  25                  30

Met Ala Leu Leu Ala Arg Lys Gln Gly Ala Gly Asp Ser Leu Ile Ala
        35                  40                  45

Gly Ser Ala Met Ser Lys Glu Lys Lys Leu Met Thr Gly His Ala Ile
    50                  55                  60

Pro Pro Ser Gln Leu Asp Ser Gln Ile Asp Asp Phe Thr Gly Phe Ser
65                  70                  75                  80

Lys Asp Gly Met Met Gln Lys Pro Gly Ser Asn Ala Pro Val Gly Gly
                85                  90                  95

Asn Val Thr Ser Ser Phe Ser Gly Asp Asp Leu Glu Cys Arg Glu Thr
            100                 105                 110

Ala Ser Ser Pro Lys Ser Gln Arg Glu Ile Asn Ala Asp Ile Lys Arg
        115                 120                 125

Lys Leu Val Lys Glu Leu Arg Cys Val Gly Gln Lys Tyr Glu Lys Ile
    130                 135                 140

Phe Glu Met Leu Glu Gly Val Gln Gly Pro Thr Ala Val Arg Lys Arg
145                 150                 155                 160

Phe Phe Glu Ser Ile Ile Lys Glu Ala Ala Arg Cys Met Arg Arg Asp
                165                 170                 175

Phe Val Lys His Leu Lys Lys Lys Leu Lys Arg Met Ile
            180                 185

<210> SEQ ID NO 9
<211> LENGTH: 189
<212> TYPE: PRT
<213> ORGANISM: Artificial Sequence
<220> FEATURE:
<223> OTHER INFORMATION: Synthetic Peptide

<400> SEQUENCE: 9

Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
            20                  25                  30

Met Ala Leu Leu Ala Arg Lys Gln Gly Ala Gly Asp Ser Leu Ile Ala
        35                  40                  45
```

Gly Ser Ala Met Ser Lys Glu Lys Lys Leu Met Thr Gly His Ala Ile
        50                  55                  60

Pro Pro Ser Gln Leu Asp Ser Gln Ile Asp Asp Phe Thr Gly Phe Ser
 65                  70                  75                  80

Lys Asp Gly Met Met Gln Lys Pro Gly Ser Asn Ala Pro Val Gly Gly
                    85                  90                  95

Asn Val Thr Ser Ser Phe Ser Gly Asp Asp Leu Glu Cys Arg Glu Thr
                100                 105                 110

Ala Ser Ser Pro Lys Ser Gln Arg Glu Ile Asn Ala Asp Ile Lys Arg
            115                 120                 125

Lys Leu Val Lys Glu Leu Arg Cys Val Gly Gln Lys Tyr Glu Lys Ile
    130                 135                 140

Phe Glu Met Leu Glu Gly Val Gln Gly Pro Thr Ala Val Arg Lys Arg
145                 150                 155                 160

Phe Phe Glu Ser Ile Ile Lys Glu Ala Ala Arg Cys Met Arg Arg Asp
                165                 170                 175

Phe Val Lys His Leu Lys Lys Lys Leu Lys Arg Met Ile
                180                 185

<210> SEQ ID NO 10
<211> LENGTH: 189
<212> TYPE: PRT
<213> ORGANISM: Artificial Sequence
<220> FEATURE:
<223> OTHER INFORMATION: Synthetic Peptide

<400> SEQUENCE: 10

Met Thr Asp Lys Thr Glu Lys Val Ala Val Asp Pro Glu Thr Val Phe
 1                   5                  10                  15

Lys Arg Pro Arg Glu Cys Asp Ser Pro Ser Tyr Gln Lys Arg Gln Arg
                    20                  25                  30

Met Ala Leu Leu Ala Arg Lys Gln Gly Ala Gly Asp Ser Leu Ile Ala
            35                  40                  45

Gly Ser Ala Met Ser Lys Glu Lys Lys Leu Met Thr Gly His Ala Ile
        50                  55                  60

Pro Pro Ser Gln Leu Asp Ser Gln Ile Asp Asp Phe Thr Gly Phe Ser
 65                  70                  75                  80

Lys Asp Arg Met Met Gln Lys Pro Gly Ser Asn Ala Pro Val Gly Gly
                    85                  90                  95

Asn Val Thr Ser Ser Phe Ser Gly Asp Asp Leu Glu Cys Arg Glu Thr
                100                 105                 110

Ala Ser Ser Pro Lys Ser Gln Arg Glu Ile Asn Ala Asp Ile Lys Arg
            115                 120                 125

Lys Leu Val Lys Glu Leu Arg Cys Val Gly Gln Lys Tyr Glu Lys Ile
    130                 135                 140

Phe Glu Met Leu Glu Gly Val Gln Gly Pro Thr Ala Val Arg Lys Arg
145                 150                 155                 160

Phe Phe Glu Ser Ile Ile Lys Glu Ala Ala Arg Cys Met Arg Arg Asp
                165                 170                 175

Phe Val Lys His Leu Lys Lys Lys Leu Lys Arg Met Ile
                180                 185

<210> SEQ ID NO 11
<211> LENGTH: 189
<212> TYPE: PRT
<213> ORGANISM: Artificial Sequence
<220> FEATURE:
<223> OTHER INFORMATION: Synthetic Peptide

<400> SEQUENCE: 11

Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
                20                  25                  30

Met Ala Leu Leu Ala Arg Lys Gln Gly Ala Gly Asp Ser Leu Ile Ala
            35                  40                  45

Gly Ser Ala Met Ser Lys Ala Lys Lys Leu Met Thr Gly His Ala Ile
        50                  55                  60

Pro Pro Ser Gln Leu Asp Ser Gln Ile Asp Asp Phe Thr Gly Phe Ser
65                  70                  75                  80

Lys Asp Arg Met Met Gln Lys Pro Gly Ser Asn Ala Pro Val Gly Gly
                85                  90                  95

Asn Val Thr Ser Ser Phe Ser Gly Asp Asp Leu Glu Cys Arg Glu Thr
            100                 105                 110

Ala Ser Ser Pro Lys Ser Gln Arg Glu Ile Asn Ala Asp Ile Lys Arg
        115                 120                 125

Lys Leu Val Lys Glu Leu Arg Cys Val Gly Gln Lys Tyr Glu Lys Ile
    130                 135                 140

Phe Glu Met Leu Glu Gly Val Gln Gly Pro Thr Ala Val Arg Lys Arg
145                 150                 155                 160

Phe Phe Glu Ser Ile Ile Lys Glu Ala Ala Arg Cys Met Arg Arg Asp
                165                 170                 175

Phe Val Lys His Leu Lys Lys Lys Leu Lys Arg Met Ile
                180                 185

<210> SEQ ID NO 12
<211> LENGTH: 189
<212> TYPE: PRT
<213> ORGANISM: Artificial Sequence
<220> FEATURE:
<223> OTHER INFORMATION: Synthetic Peptide

<400> SEQUENCE: 12

Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
                20                  25                  30

Met Ala Leu Leu Ala Arg Lys Gln Gly Ala Gly Asp Ser Leu Ile Ala
            35                  40                  45

Gly Ser Ala Met Ser Lys Ala Lys Lys Leu Met Thr Gly His Ala Ile
        50                  55                  60

Pro Pro Ser Gln Leu Asp Ser Gln Ile Asp Asp Phe Thr Gly Phe Ser
65                  70                  75                  80

Lys Asp Arg Met Met Gln Lys Pro Gly Ser Asn Ala Pro Val Gly Gly
                85                  90                  95

Asn Val Thr Ser Ser Phe Ser Gly Asp Asp Leu Glu Cys Arg Glu Thr
            100                 105                 110

Ala Ser Ser Pro Lys Ser Gln Gln Glu Ile Asn Ala Asp Ile Lys Arg
        115                 120                 125

Lys Leu Val Lys Glu Leu Arg Cys Val Gly Gln Lys Tyr Glu Lys Ile
    130                 135                 140

```
Phe Glu Met Leu Glu Gly Val Gln Gly Pro Thr Ala Val Arg Lys Arg
145                 150                 155                 160

Phe Phe Glu Ser Ile Ile Lys Glu Ala Ala Arg Cys Met Arg Arg Asp
            165                 170                 175

Phe Val Lys His Leu Lys Lys Lys Leu Lys Arg Met Ile
        180                 185

<210> SEQ ID NO 13
<211> LENGTH: 189
<212> TYPE: PRT
<213> ORGANISM: Artificial Sequence
<220> FEATURE:
<223> OTHER INFORMATION: Synthetic Peptide

<400> SEQUENCE: 13

Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
            20                  25                  30

Met Ala Leu Leu Ala Arg Lys Gln Gly Ala Gly Asp Ser Leu Ile Ala
        35                  40                  45

Gly Ser Ala Met Ser Lys Glu Lys Lys Leu Met Thr Gly His Ala Ile
    50                  55                  60

Pro Pro Ser Gln Leu Asp Ser Gln Ile Asp Asp Phe Thr Gly Phe Ser
65                  70                  75                  80

Lys Asp Arg Met Met Gln Lys Pro Gly Ser Asn Ala Pro Val Gly Gly
                85                  90                  95

Asn Val Thr Ser Ser Phe Ser Gly Asp Asp Leu Glu Cys Arg Glu Thr
            100                 105                 110

Ala Phe Ser Pro Lys Ser Gln Gln Glu Ile Asn Ala Asp Ile Lys Arg
        115                 120                 125

Gln Leu Val Lys Glu Leu Arg Cys Val Gly Gln Lys Tyr Glu Lys Ile
    130                 135                 140

Phe Glu Met Leu Glu Gly Val Gln Gly Pro Thr Ala Val Arg Lys Arg
145                 150                 155                 160

Phe Phe Glu Ser Ile Ile Lys Glu Ala Ala Arg Cys Met Arg Arg Asp
            165                 170                 175

Phe Val Lys His Leu Lys Lys Lys Leu Lys Arg Met Ile
        180                 185

<210> SEQ ID NO 14
<211> LENGTH: 189
<212> TYPE: PRT
<213> ORGANISM: Artificial Sequence
<220> FEATURE:
<223> OTHER INFORMATION: Synthetic Peptide

<400> SEQUENCE: 14

Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
            20                  25                  30

Met Ala Leu Leu Ala Arg Lys Gln Gly Ala Gly Asp Ser Leu Ile Ala
        35                  40                  45

Gly Ser Ala Met Ser Lys Glu Lys Lys Leu Met Thr Gly His Ala Ile
    50                  55                  60
```

```
Pro Pro Ser Gln Leu Asp Ser Gln Ile Asp Asp Phe Thr Gly Phe Ser
 65                  70                  75                  80

Lys Asp Arg Met Met Gln Lys Pro Gly Ser Asn Ala Pro Val Gly Gly
                 85                  90                  95

Asn Val Thr Ser Ser Phe Ser Gly Asp Asp Leu Glu Cys Arg Glu Thr
            100                 105                 110

Ala Phe Ser Pro Lys Ser Gln Gln Glu Ile Asn Ala Asp Ile Lys Arg
        115                 120                 125

Gln Leu Val Lys Glu Leu Arg Cys Val Gly Gln Lys Tyr Glu Lys Ile
    130                 135                 140

Phe Glu Met Leu Glu Gly Val Gln Gly Pro Thr Ala Val Arg Lys Arg
145                 150                 155                 160

Phe Phe Glu Ser Ile Ile Lys Glu Ala Ala Arg Cys Met Arg Arg Asp
                165                 170                 175

Phe Val Lys His Leu Lys Lys Lys Leu Lys Arg Met Ile
                180                 185

<210> SEQ ID NO 15
<211> LENGTH: 189
<212> TYPE: PRT
<213> ORGANISM: Artificial Sequence
<220> FEATURE:
<223> OTHER INFORMATION: Synthetic Peptide

<400> SEQUENCE: 15

Met Thr Asp Lys Thr Glu Lys Val Ala Val Asp Pro Glu Thr Val Phe
 1               5                  10                  15

Lys Arg Pro Arg Glu Cys Asp Ser Pro Ser Tyr Gln Lys Arg Gln Arg
                 20                  25                  30

Met Ala Leu Leu Ala Arg Lys Gln Gly Ala Gly Asp Ser Leu Ile Ala
             35                  40                  45

Gly Ser Ala Met Ser Lys Glu Lys Lys Leu Met Thr Gly His Ala Ile
 50                  55                  60

Pro Pro Ser Gln Leu Asp Ser Gln Ile Asp Asp Phe Thr Gly Phe Ser
 65                  70                  75                  80

Lys Asp Arg Met Met Gln Lys Pro Gly Ser Asn Ala Pro Val Gly Gly
                 85                  90                  95

Asn Val Thr Ser Ser Phe Ser Gly Asp Asp Leu Glu Cys Arg Glu Thr
            100                 105                 110

Ala Phe Ser Pro Lys Ser Gln Gln Glu Ile Asn Ala Asp Ile Lys Arg
        115                 120                 125

Gln Leu Val Lys Glu Leu Arg Cys Val Gly Gln Lys Tyr Glu Lys Ile
    130                 135                 140

Phe Glu Met Leu Glu Gly Val Gln Gly Pro Thr Ala Val Arg Lys Arg
145                 150                 155                 160

Phe Phe Glu Ser Ile Ile Lys Glu Ala Ala Arg Cys Met Arg Arg Asp
                165                 170                 175

Phe Val Lys His Leu Lys Lys Lys Leu Lys Arg Met Ile
                180                 185

<210> SEQ ID NO 16
<211> LENGTH: 189
<212> TYPE: PRT
<213> ORGANISM: Artificial Sequence
<220> FEATURE:
<223> OTHER INFORMATION: Synthetic Peptide
```

<400> SEQUENCE: 16

Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
                20                  25                  30

Met Ala Leu Leu Ala Arg Lys Gln Gly Ala Gly Asp Ser Leu Ile Ala
                35                  40                  45

Gly Ser Ala Met Ser Lys Glu Lys Lys Leu Met Thr Gly His Ala Ile
50                  55                  60

Pro Pro Ser Gln Leu Asp Ser Gln Ile Asp Asp Phe Thr Gly Phe Ser
65                  70                  75                  80

Lys Asp Gly Met Met Gln Lys Pro Gly Ser Asn Ala Pro Val Gly Gly
                85                  90                  95

Asn Val Thr Ser Asn Phe Ser Gly Asp Asp Leu Glu Cys Arg Gly Ile
                100                 105                 110

Ala Ser Ser Pro Lys Ser Gln Gln Glu Ile Asn Ala Asp Ile Lys Cys
                115                 120                 125

Gln Val Val Lys Glu Ile Arg Cys Leu Gly Arg Lys Tyr Glu Lys Ile
130                 135                 140

Phe Glu Met Leu Glu Gly Val Gln Gly Pro Thr Ala Val Arg Lys Arg
145                 150                 155                 160

Phe Phe Glu Ser Ile Ile Lys Glu Ala Ala Arg Cys Met Arg Arg Asp
                165                 170                 175

Phe Val Lys His Leu Lys Lys Lys Leu Lys Arg Met Ile
                180                 185

<210> SEQ ID NO 17
<211> LENGTH: 189
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (55)..(55)
<223> OTHER INFORMATION: Xaa is Ala or Glu
<220> FEATURE:
<221> NAME/KEY: MISC_FEATURE
<222> LOCATION: (83)..(83)
<223> OTHER INFORMATION: Xaa is Gly or Arg
<220> FEATURE:
<221> NAME/KEY: MISC_FEATURE
<222> LOCATION: (101)..(101)
<223> OTHER INFORMATION: Xaa is Ser or Asn
<220> FEATURE:
<221> NAME/KEY: MISC_FEATURE
<222> LOCATION: (111)..(111)
<223> OTHER INFORMATION: Xaa is Gly or Glu
<220> FEATURE:
<221> NAME/KEY: MISC_FEATURE
<222> LOCATION: (112)..(112)
<223> OTHER INFORMATION: Xaa is Iso or Thr
<220> FEATURE:
<221> NAME/KEY: MISC_FEATURE
<222> LOCATION: (114)..(114)
<223> OTHER INFORMATION: Xaa is Ser or Phe
<220> FEATURE:
<221> NAME/KEY: MISC_FEATURE
<222> LOCATION: (120)..(120)
<223> OTHER INFORMATION: Xaa is Gln or Arg
<220> FEATURE:
<221> NAME/KEY: MISC_FEATURE
<222> LOCATION: (128)..(128)
<223> OTHER INFORMATION: Xaa is Arg or Cys
<220> FEATURE:
<221> NAME/KEY: MISC_FEATURE

```
<222> LOCATION: (129)..(129)
<223> OTHER INFORMATION: Xaa is Lys or Gln
<220> FEATURE:
<221> NAME/KEY: MISC_FEATURE
<222> LOCATION: (130)..(130)
<223> OTHER INFORMATION: Xaa is Leu or Val
<220> FEATURE:
<221> NAME/KEY: MISC_FEATURE
<222> LOCATION: (134)..(134)
<223> OTHER INFORMATION: Xaa is Iso or Leu
<220> FEATURE:
<221> NAME/KEY: MISC_FEATURE
<222> LOCATION: (137)..(137)
<223> OTHER INFORMATION: Xaa is Leu or Val
<220> FEATURE:
<221> NAME/KEY: MISC_FEATURE
<222> LOCATION: (139)..(139)
<223> OTHER INFORMATION: Xaa is Arg or Gln

<400> SEQUENCE: 17

Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
            20                  25                  30

Met Ala Leu Leu Ala Arg Lys Gln Gly Ala Gly Asp Ser Leu Ile Ala
        35                  40                  45

Gly Ser Ala Met Ser Lys Xaa Lys Lys Leu Met Thr Gly His Ala Ile
50                  55                  60

Pro Pro Ser Gln Leu Asp Ser Gln Ile Asp Asp Phe Thr Gly Phe Ser
65                  70                  75                  80

Lys Asp Xaa Met Met Gln Lys Pro Gly Ser Asn Ala Pro Val Gly Gly
                85                  90                  95

Asn Val Thr Ser Xaa Phe Ser Gly Asp Asp Leu Glu Cys Arg Xaa Xaa
            100                 105                 110

Ala Xaa Ser Pro Lys Ser Gln Xaa Glu Ile Asn Ala Asp Ile Lys Xaa
        115                 120                 125

Xaa Xaa Val Lys Glu Xaa Arg Cys Xaa Gly Xaa Lys Tyr Glu Lys Ile
        130                 135                 140

Phe Glu Met Leu Glu Gly Val Gln Gly Pro Thr Ala Val Arg Lys Arg
145                 150                 155                 160

Phe Phe Glu Ser Ile Ile Lys Glu Ala Ala Arg Cys Met Arg Arg Asp
                165                 170                 175

Phe Val Lys His Leu Lys Lys Lys Leu Lys Arg Met Ile
                180                 185

<210> SEQ ID NO 18
<211> LENGTH: 119
<212> TYPE: PRT
<213> ORGANISM: Artificial Sequence
<220> FEATURE:
<223> OTHER INFORMATION: Synthetic Peptide

<400> SEQUENCE: 18

Thr Asp Lys Thr Glu Lys Val Ala Val Asp Pro Glu Thr Val Phe Lys
1               5                   10                  15

Arg Pro Arg Glu Cys Asp Ser Pro Ser Tyr Gln Lys Arg Gln Arg Met
            20                  25                  30

Ala Leu Leu Ala Arg Lys Gln Gly Ala Gly Asp Ser Leu Ile Ala Gly
        35                  40                  45

Ser Ala Met Ser Lys Glu Lys Lys Leu Met Thr Gly His Ala Ile Pro
50                  55                  60
```

```
Pro Ser Gln Leu Asp Ser Gln Ile Asp Asp Phe Thr Gly Phe Ser Lys
 65                  70                  75                  80

Asp Gly Met Met Gln Lys Pro Gly Ser Asn Ala Pro Val Gly Gly Asn
                 85                  90                  95

Val Thr Ser Ser Phe Ser Gly Asp Asp Leu Glu Cys Arg Glu Thr Ala
            100                 105                 110

Ser Ser Pro Lys Ser Gln Arg
            115
```

<210> SEQ ID NO 19
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 19

```
Met Thr Asp Lys Thr Glu Lys Val Ala Val Asp Pro Glu Thr Val Phe
  1               5                  10                  15

Lys Arg Pro Arg Glu Cys Asp Ser Pro Ser Tyr Gln Lys Arg Gln Arg
                 20                  25                  30

Met Ala Leu Leu Ala Arg Lys Gln Gly Ala Gly Asp Ser Leu Ile Ala
             35                  40                  45

Gly Ser Ala Met Ser Lys Glu Lys Lys Leu Met Thr Gly His Ala Ile
 50                  55                  60

Pro Pro Ser Gln Leu Asp Ser Gln Ile Asp Asp Phe Thr Gly Phe Ser
 65                  70                  75                  80

Lys Asp Gly Met Met Gln Lys Pro Gly Ser Asn Ala Pro Val Gly Gly
                 85                  90                  95

Asn Val Thr Ser Ser Phe Ser Gly Asp Asp Leu Glu Cys Arg Glu Thr
            100                 105                 110

Ala Ser Ser Pro Lys Ser Gln Arg
            115                 120
```

<210> SEQ ID NO 20
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 20

```
Met Thr Asp Lys Thr Glu Lys Val Ala Val Asp Pro Glu Thr Val Phe
  1               5                  10                  15

Lys Arg Pro Arg Glu Cys Asp Ser Pro Ser Tyr Gln Lys Arg Gln Arg
                 20                  25                  30

Met Ala Leu Leu Ala Arg Lys Gln Gly Ala Gly Asp Ser Leu Ile Ala
             35                  40                  45

Gly Ser Ala Met Ser Lys Glu Lys Lys Leu Met Thr Gly His Ala Ile
 50                  55                  60

Pro Pro Ser Gln Leu Asp Ser Gln Ile Asp Asp Phe Thr Gly Phe Ser
 65                  70                  75                  80

Lys Asp Gly Met Met Gln Lys Pro Gly Ser Asn Ala Pro Val Gly Gly
                 85                  90                  95

Asn Val Thr Ser Ser Phe Ser Gly Asp Asp Leu Glu Cys Arg Glu Thr
            100                 105                 110

Ala Ser Ser Pro Lys Ser Gln Arg
            115                 120
```

<210> SEQ ID NO 21
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 21

```
Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
                20                  25                  30

Met Ala Leu Leu Ala Arg Lys Gln Gly Ala Gly Asp Ser Leu Ile Ala
            35                  40                  45

Gly Ser Ala Met Ser Lys Glu Lys Lys Leu Met Thr Gly His Ala Ile
        50                  55                  60

Pro Pro Ser Gln Leu Asp Ser Gln Ile Asp Asp Phe Thr Gly Phe Ser
65                  70                  75                  80

Lys Asp Arg Met Met Gln Lys Pro Gly Ser Asn Ala Pro Val Gly Gly
                85                  90                  95

Asn Val Thr Ser Ser Phe Ser Gly Asp Asp Leu Glu Cys Arg Glu Thr
            100                 105                 110

Ala Ser Ser Pro Lys Ser Gln Arg
        115                 120
```

<210> SEQ ID NO 22
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 22

```
Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
                20                  25                  30

Met Ala Leu Leu Ala Arg Lys Gln Gly Ala Gly Asp Ser Leu Ile Ala
            35                  40                  45

Gly Ser Ala Met Ser Lys Ala Lys Lys Leu Met Thr Gly His Ala Ile
        50                  55                  60

Pro Pro Ser Gln Leu Asp Ser Gln Ile Asp Asp Phe Thr Gly Phe Ser
65                  70                  75                  80

Lys Asp Arg Met Met Gln Lys Pro Gly Ser Asn Ala Pro Val Gly Gly
                85                  90                  95

Asn Val Thr Ser Ser Phe Ser Gly Asp Asp Leu Glu Cys Arg Glu Thr
            100                 105                 110

Ala Ser Ser Pro Lys Ser Gln Arg
        115                 120
```

<210> SEQ ID NO 23
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 23

Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
            20                  25                  30

Met Ala Leu Leu Ala Arg Lys Gln Gly Ala Gly Asp Ser Leu Ile Ala
        35                  40                  45

Gly Ser Ala Met Ser Lys Ala Lys Lys Leu Met Thr Gly His Ala Ile
50                  55                  60

Pro Pro Ser Gln Leu Asp Ser Gln Ile Asp Asp Phe Thr Gly Phe Ser
65                  70                  75                  80

Lys Asp Arg Met Met Gln Lys Pro Gly Ser Asn Ala Pro Val Gly Gly
                85                  90                  95

Asn Val Thr Ser Ser Phe Ser Gly Asp Asp Leu Glu Cys Arg Glu Thr
            100                 105                 110

Ala Ser Ser Pro Lys Ser Gln Gln
            115                 120

<210> SEQ ID NO 24
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 24

Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
            20                  25                  30

Met Ala Leu Leu Ala Arg Lys Gln Gly Ala Gly Asp Ser Leu Ile Ala
        35                  40                  45

Gly Ser Ala Met Ser Lys Glu Lys Lys Leu Met Thr Gly His Ala Ile
50                  55                  60

Pro Pro Ser Gln Leu Asp Ser Gln Ile Asp Asp Phe Thr Gly Phe Ser
65                  70                  75                  80

Lys Asp Arg Met Met Gln Lys Pro Gly Ser Asn Ala Pro Val Gly Gly
                85                  90                  95

Asn Val Thr Ser Ser Phe Ser Gly Asp Asp Leu Glu Cys Arg Glu Thr
            100                 105                 110

Ala Phe Ser Pro Lys Ser Gln Gln
            115                 120

<210> SEQ ID NO 25
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 25

Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
            20                  25                  30

Met Ala Leu Leu Ala Arg Lys Gln Gly Ala Gly Asp Ser Leu Ile Ala
        35                  40                  45

```
Gly Ser Ala Met Ser Lys Glu Lys Lys Leu Met Thr Gly His Ala Ile
        50                  55                  60

Pro Pro Ser Gln Leu Asp Ser Gln Ile Asp Asp Phe Thr Gly Phe Ser
 65                  70                  75                  80

Lys Asp Arg Met Met Gln Lys Pro Gly Ser Asn Ala Pro Val Gly Gly
                85                  90                  95

Asn Val Thr Ser Ser Phe Ser Gly Asp Asp Leu Glu Cys Arg Glu Thr
                100                 105                 110

Ala Phe Ser Pro Lys Ser Gln Gln
                115                 120

<210> SEQ ID NO 26
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 26

Met Thr Asp Lys Thr Glu Lys Val Ala Val Asp Pro Glu Thr Val Phe
 1               5                  10                  15

Lys Arg Pro Arg Glu Cys Asp Ser Pro Ser Tyr Gln Lys Arg Gln Arg
                20                  25                  30

Met Ala Leu Leu Ala Arg Lys Gln Gly Ala Gly Asp Ser Leu Ile Ala
                35                  40                  45

Gly Ser Ala Met Ser Lys Glu Lys Lys Leu Met Thr Gly His Ala Ile
        50                  55                  60

Pro Pro Ser Gln Leu Asp Ser Gln Ile Asp Asp Phe Thr Gly Phe Ser
 65                  70                  75                  80

Lys Asp Arg Met Met Gln Lys Pro Gly Ser Asn Ala Pro Val Gly Gly
                85                  90                  95

Asn Val Thr Ser Ser Phe Ser Gly Asp Asp Leu Glu Cys Arg Glu Thr
                100                 105                 110

Ala Phe Ser Pro Lys Ser Gln Gln
                115                 120

<210> SEQ ID NO 27
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 27

Met Thr Asp Lys Thr Glu Lys Val Ala Val Asp Pro Glu Thr Val Phe
 1               5                  10                  15

Lys Arg Pro Arg Glu Cys Asp Ser Pro Ser Tyr Gln Lys Arg Gln Arg
                20                  25                  30

Met Ala Leu Leu Ala Arg Lys Gln Gly Ala Gly Asp Ser Leu Ile Ala
                35                  40                  45

Gly Ser Ala Met Ser Lys Glu Lys Lys Leu Met Thr Gly His Ala Ile
        50                  55                  60

Pro Pro Ser Gln Leu Asp Ser Gln Ile Asp Asp Phe Thr Gly Phe Ser
 65                  70                  75                  80

Lys Asp Gly Met Met Gln Lys Pro Gly Ser Asn Ala Pro Val Gly Gly
                85                  90                  95
```

Asn Val Thr Ser Ser Phe Ser Gly Asp Asp Leu Glu Cys Arg Gly Ile
            100                 105                 110

Ala Ser Ser Pro Lys Ser Gln Gln
        115                 120

<210> SEQ ID NO 28
<211> LENGTH: 120
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (111)..(112)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid

<400> SEQUENCE: 28

Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
            20                  25                  30

Met Ala Leu Leu Ala Arg Lys Gln Gly Ala Gly Asp Ser Leu Ile Ala
        35                  40                  45

Gly Ser Ala Met Ser Lys Xaa Lys Lys Leu Met Thr Gly His Ala Ile
50                  55                  60

Pro Pro Ser Gln Leu Asp Ser Gln Ile Asp Asp Phe Thr Gly Phe Ser
65                  70                  75                  80

Lys Asp Xaa Met Met Gln Lys Pro Gly Ser Asn Ala Pro Val Gly Gly
            85                  90                  95

Asn Val Thr Ser Xaa Phe Ser Gly Asp Asp Leu Glu Cys Arg Xaa Xaa
            100                 105                 110

Ala Xaa Ser Pro Lys Ser Gln Xaa
        115                 120

<210> SEQ ID NO 29
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 29

Gly Val Gln Gly Pro Thr Ala Val Arg Lys Arg
1               5                   10

```
<210> SEQ ID NO 30
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 30

Val Gln Gly Pro Thr Ala Val Arg Lys Arg
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 31

Gln Gly Pro Thr Ala Val Arg Lys Arg
1               5

<210> SEQ ID NO 32
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 32

Glu Gly Val Gln Gly Pro Thr Ala Val Arg
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 33

Val Ala Val Asp Pro Glu Thr Val Phe Lys Arg
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 34

Arg Leu Arg Pro Gly Gly Lys Lys Lys
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 35

Gln Val Pro Leu Arg Pro Met Thr Tyr Lys
1               5                   10

<210> SEQ ID NO 36
```

```
<211> LENGTH: 9
<212> TYPE: PRT
<213> ORGANISM: Artificial Sequence
<220> FEATURE:
<223> OTHER INFORMATION: Allele: HLA-B*35:01
<220> FEATURE:
<221> NAME/KEY: misc_feature
<222> LOCATION: (1)..(9)
<223> OTHER INFORMATION: Xaa can be any naturally occurring amino acid

<400> SEQUENCE: 36

Xaa Xaa Xaa Xaa Xaa Xaa Xaa Xaa Xaa
1               5

<210> SEQ ID NO 37
<211> LENGTH: 9
<212> TYPE: PRT
<213> ORGANISM: Artificial Sequence
<220> FEATURE:
<223> OTHER INFORMATION: Allele: HLA-A*03:01/11:01
<220> FEATURE:
<221> NAME/KEY: misc_feature
<222> LOCATION: (1)..(9)
<223> OTHER INFORMATION: Xaa can be any naturally occurring amino acid

<400> SEQUENCE: 37

Xaa Xaa Xaa Xaa Xaa Xaa Xaa Xaa Xaa
1               5

<210> SEQ ID NO 38
<211> LENGTH: 9
<212> TYPE: PRT
<213> ORGANISM: Artificial Sequence
<220> FEATURE:
<223> OTHER INFORMATION: Allele: HLA-B*18:0135:01
<220> FEATURE:
<221> NAME/KEY: misc_feature
<222> LOCATION: (1)..(9)
<223> OTHER INFORMATION: Xaa can be any naturally occurring amino acid

<400> SEQUENCE: 38

Xaa Xaa Xaa Xaa Xaa Xaa Xaa Xaa Xaa
1               5

<210> SEQ ID NO 39
<211> LENGTH: 9
<212> TYPE: PRT
<213> ORGANISM: Artificial Sequence
<220> FEATURE:
<223> OTHER INFORMATION: Allele: HLA-A*03:01/68:01
<220> FEATURE:
<221> NAME/KEY: misc_feature
<222> LOCATION: (1)..(9)
<223> OTHER INFORMATION: Xaa can be any naturally occurring amino acid

<400> SEQUENCE: 39

Xaa Xaa Xaa Xaa Xaa Xaa Xaa Xaa Xaa
1               5
```

METHODS OF TREATING CANCERS WITH CT45 TARGETED THERAPIES

CROSS-REFERENCE TO RELATED APPLICATIONS

This application is division of U.S. patent application Ser. No. 16/300,267 filed Nov. 9, 2018, which is a national phase application under 35 U.S.C. § 371 of International Application No. PCT/IB2017/052781 filed May 11, 2017, which claims the benefit of priority of U.S. Provisional Patent Application No. 62/334,782 filed May 11, 2016. The entire contents of each of the above-referenced disclosures are specifically incorporated herein by reference without disclaimer.

SEQUENCE LISTING

The instant application contains a Sequence Listing which has been submitted electronically in ASCII format and is hereby incorporated by reference in its entirety. Said ASCII copy, created on Jan. 26, 2022, is named Sequence Listing.txt and is 37,129 bytes in size.

BACKGROUND OF THE INVENTION

I. Field of the Invention

Embodiments are directed generally to biology and medicine. In certain aspects there are methods and compositions for treating cancers.

II. Background

Resistance to chemotherapy is a major factor in the poor survival rate of women who develop ovarian cancers such as high-grade serous ovarian carcinoma (HGSOC), the most malignant form of ovarian cancer. HSC accounts for 70% of all ovarian cancers, and 60% of deaths related to the disease. Every year, around 80,000 women worldwide die of HGSOC, a figure that has barely altered in recent decades. Because of the aggressive nature of epithelial ovarian cancers, there is little room for trial and error when it comes to selecting the appropriate treatment. More recently, technological advances in personalized medicine have streamlined the ways we treat cancer, and knowledge about how a cancer is likely to respond to a treatment will ultimately lead to more effective therapies than the trial and error approach.

There is a need in the art for advanced personalized treatments in aggressive epithelial ovarian cancers and for new therapies that specifically target aggressive cancer cells.

SUMMARY OF THE INVENTION

The current disclosure fulfills the aforementioned need in the art by providing methods for treating ovarian cancer based on specific antigen expression of the cancer. Furthermore, the expressed antigen may be used in immunotherapeutic methods for treatment of the ovarian cancer.

Aspects of the disclosure relate to isolated T cells comprising a chimeric antigen receptor (CAR) or a T cell receptor (TCR), wherein the CAR or TCR specifically binds to a CT45 polypeptide. In some embodiments, the CT45 polypeptide comprises a sequence selected from SEQ ID NOS: 1-6 or 29-33 or a polypeptide with at least 70% identity to SEQ ID NO:1-6 or 29-33. In specific embodiments, one or more of these sequences may be excluded.

SEQ ID NOS: 1-6 and 29-33 correspond to AVDPETVFK (SEQ ID NO:1); GVQGPTAVR (SEQ ID NO:2); GVQGPTAVRK (SEQ ID NO:3); VQGPTAVRK (SEQ ID NO: 4); QGPTAVRK (SEQ ID NO:5); QGPTAVR (SEQ ID NO:6); GVQGPTAVRKR (SEQ ID NO: 29); VQGPTAVRKR (SEQ ID NO:30); QGPTAVRKR (SEQ ID NO:31); EGVQGPTAVR (SEQ ID NO:32); and VAVDPETVFKR (SEQ ID NO:33). In some embodiments or the cells and methods described herein, the polypeptide is or is at least 70%, 75%, 80%, 85%, 90%, 91%, 92%, 93%, 94%, 95%, 96%, 97%, 98%, or 99% identical or similar to one of SEQ ID NOS: 1-6 or 29-33. In some embodiments, the polypeptide has at least 3, 4, 5, 6, 7, 8, 9, 10, 11, 12, 13, 14, 15, 16, 17, 18, 19, 20, 25, 30, 35, 40, 50, 75, or 100 contiguous amino acids (or any derivable range therein) of a polypeptide described herein. In further embodiments, a polypeptide may have one of these sequences except it may have, have at least, or have at most 1, 2, 3, 4, 5, 6, 7 or more amino acid substitutions (or any range derivable therein, which may or may not be conservative substitutions. In further embodiments, a polypeptide may have one of these sequences except the amino acid at position 1, 2, 3, 4, 5, 6, 7, 8, 9, 10, 11, 12, 13, and/or 14 may be deleted, substituted, or their may be an addition of 1, 2, 3, 4, 5, 6 or more amino acids (and any range derivable therein) before or after the amino acid (going from the N-terminal end to the C-terminal end of the polypeptide. In some embodiments, the polypeptide is a polypeptide described in FIG. 4 or a fragment thereof or one with a certain percentage or identity to a polypeptide shown in FIG. 4. In some embodiments of the methods, cells, and bi-specific T-cell engagers of the disclosure, the CT45 polypeptide is a CT45A polypeptide. CT45A polypeptides are shown in FIG. 4.

In some embodiments, the polypeptide comprises SEQ ID NO: 1, 3, or 6 or a polypeptide with at least 70% identity to SEQ ID NO:1, 3, or 6.

In some embodiments, the TCR is heterologous. The TCR may be a TCR gene that is transferred from another organism. In some embodiments, the TCR gene (or genes) are extra-chromosomal.

Further aspects of the disclosure relate to isolated dendritic cells comprising an extra-chromosomal CT45 polypeptide. In some embodiments, the polypeptide comprises a sequence selected from SEQ ID NOS: 1-6 or 29-33 or a polypeptide with at least 70% identity to SEQ ID NO: 1-6 or 29-33. In some embodiments, the polypeptide comprises SEQ ID NO:1, 3, or 6 or a polypeptide with at least 70% identity to SEQ ID NO:1, 3, or 6.

Yet further aspects relate to isolated dendritic cells primed with a CT45 polypeptide. In some embodiments, the polypeptide comprises a sequence selected from SEQ ID NOS: 1-6 or 29-33 or a polypeptide with at least 70% identity to SEQ ID NO: 1-6 or 29-33. In some embodiments, the polypeptide comprises SEQ ID NO:1, 3, or 6 or a polypeptide with at least 70% identity to SEQ ID NO:1, 3, or 6.

Further aspects relate to a bispecific T-cell engager that comprises a single-chain fragment variable that specifically binds to a CT45 polypeptide. In some embodiments, the polypeptide comprises a sequence selected from SEQ ID NOS: 1-6 or 29-33 or a polypeptide with at least 70% identity to SEQ ID NO:1-6 or 29-33. In some embodiments, the polypeptide comprises SEQ ID NO: 1, 3, or 6 or a polypeptide with at least 70% identity to SEQ ID NO:1, 3, or 6.

Further aspects of the disclosure relate to antibodies with specificity for a CT45 polypeptide. In some embodiments, the antibody has a specificity for one or more of SEQ ID NOS: 1-6 or 29-33. Further aspects include a method of making the antibody comprising administration of a peptide having an amino acid sequence of SEQ ID NOS: 1-6 or 29-33 and isolating antibodies. In some embodiments, the isolated antibodies are cloned, sequenced, and/or made into hybridomas. Further aspects of the disclosure relate to a hybridoma cell line expressing an antibody specific for a CT45 peptide of SEQ ID NOS: 1-6 or 29-33.

The disclosure also relates to a method for treating ovarian cancer in a patient comprising administering the T cells, dendritic cells, antibodies, or bi-specific T-cell engagers described herein. In some embodiments, the patient has been determined to have a CT45-expressing ovarian cancer. In some embodiments, the ovarian cancer is high-grade serous ovarian cancer (HGSOC). In some embodiments, the T cells or dendritic cells are autologous. In some embodiments, the T cells or dendritic cells are derived from a precursor cell that is differentiated into a T cell or a dendritic cell in vitro. In some embodiments, the method comprises administering T cells to the patient. In some embodiments, the T cells are contacted with one or more of IL-2, anti-CD3, and allo-reactive feeder cells prior to administration to the patient. In some embodiments, the method further comprises lymphodepletion of the patient prior to administration of the T cells. In some embodiments, the method further comprises administration of IL-2. The IL-2 may be administered before, after, or concurrently with the cells or bi-specific T-cell engager. In some embodiments, the T cells have been contacted with a maturation agent. In some embodiments, the maturation agent is one or more of GM-CSF, IL-1β, TNF-α, and PGE2. In some embodiments, the method further comprises administration of an additional therapeutic agent. In some embodiments, the additional therapeutic is selected from a chemotherapeutic agent, a checkpoint inhibitor, a MUC-1 inhibitor, a CD40 activator, an IDO inhibitor, and an OX86 agonists. In some embodiments, the additional therapeutic is a chemotherapeutic agent. In some embodiments, the chemotherapeutic agent is a DNA damaging agent. In some embodiments, the DNA damaging agent is a platinum-containing compound. In some embodiments, the platinum-containing compound is cisplatin, carboplatin, oxaliplatin, nedaplatin, triplatin tetranitrate, phenanthriplatin, picoplatin, or satraplatin. In some embodiments, the method further comprises administration of an ionizing radiation therapy. In some embodiments, the method further comprises administration of a DNA methyltransferase inhibitor prior to administration of the dendritic cells, T cells, or bi-specific T-cell engager. In some embodiments, the patient is determined to have a cancer with low or no significant expression of CT45.

A further aspect relates to a method for treating ovarian cancer in a patient comprising contacting a T cell with a CT45 polypeptide and administering the T cells to the patient. In some embodiments, the patient has been determined to have a CT45-expressing ovarian cancer. In some embodiments, the T cells are autologous. In some embodiments, the T cells are PBMCs. In some embodiments, the CT45 polypeptide comprises a sequence selected from SEQ ID NOS: 1-6 or 29-33 or a polypeptide with at least 70% identity to SEQ ID NO: 1-6 or 29-33. In some embodiments, the ovarian cancer is high-grade serous ovarian cancer (HGSOC). In some embodiments, the ovarian cancer is one described herein. In some embodiments, the T cells are contacted with one or more of IL-2, anti-CD3, and allo-reactive feeder cells prior to administration to the patient. In some embodiments, the method further comprises lymphodepletion of the patient prior to administration of the T cells. In some embodiments, the method further comprises administration of IL-2. The IL-2 may be administered before, after, or concurrently with the cells or bi-specific T-cell engager. In some embodiments, the method further comprises administration of an additional therapeutic agent. In some embodiments, the additional therapeutic is selected from a chemotherapeutic agent, a checkpoint inhibitor, a MUC-1 inhibitor, a CD40 activator, an IDO inhibitor, and an OX86 agonists. In some embodiments, the additional therapeutic is a chemotherapeutic agent. In some embodiments, the chemotherapeutic agent is a DNA damaging agent. In some embodiments, the DNA damaging agent is a platinum-containing compound. In some embodiments, the platinum-containing compound is cisplatin, carboplatin, oxaliplatin, nedaplatin, triplatin tetranitrate, phenanthriplatin, picoplatin, or satraplatin. In some embodiments, the method further comprises administration of an ionizing radiation therapy. In some embodiments, the method further comprises administration of a DNA methyltransferase inhibitor prior to administration of the dendritic cells, T cells, or bi-specific T-cell engager. In some embodiments, the patient is determined to have a cancer with low or no significant expression of CT45.

A further aspect of the disclosure relates to a method for treating a patient determined to have a CT45-expressing ovarian cancer comprising administering a chemotherapeutic agent to the patient. In some embodiments, the CT45-expressing ovarian cancer is determined to be a high-expressing ovarian cancer. In some embodiments, the chemotherapeutic agent is a DNA damaging agent. In some embodiments, the DNA damaging agent is a platinum-containing compound. In some embodiments, the compound is cisplatin, carboplatin, oxaliplatin, nedaplatin, triplatin tetranitrate, phenanthriplatin, picoplatin, or satraplatin. In some embodiments, the method further comprises administration of an additional therapeutic agent. In some embodiments, the additional therapeutic is selected from a checkpoint inhibitor, a MUC-1 inhibitor, a CD40 activator, an IDO inhibitor, and an OX86 agonists. In some embodiments, the ovarian cancer is HGSOC. In some embodiments, the ovarian cancer is one described herein.

A further aspect relates to a method for treating a patient with ovarian cancer comprising: treating the patient with a chemotherapeutic agent after the patient is determined to have a high level of CT45 expression in a cancerous sample from the patient compared to a control; or treating the patient with DNA methyltransferase inhibitors, surgery, PP4 inhibitors, hormone therapy, targeted therapy and/or radiation therapy after the patient is determined to have a low level of CT45 expression in a cancerous sample from the patient compared to a control. In some embodiments, the method further comprises measuring the expression level of CT45 in a cancerous sample from the patient. In some embodiments, the method further comprises comparing the expression level of CT45 in the cancerous sample from the patient to the expression level of CT45 in a control. In some embodiments, the method further comprises comparing the expression level of CT45 in the cancerous sample from the patient to a cut-off value. In some embodiments, the ovarian cancer is HGSOC. In some embodiments, the chemotherapeutic agent is a DNA damaging agent. In some embodiments, the DNA damaging agent is a platinum-containing compound. In some embodiments, the compound is cisplatin, carboplatin, oxaliplatin, nedaplatin, triplatin tetranitrate, phenanthriplatin, picoplatin, or satraplatin. In some embodiments, the method further comprises administration of an additional therapeutic agent. In some embodiments, the treatment for a patient determined to have a high level of expression excludes PP4 inhibitors In some embodiments, the additional therapeutic is selected from a checkpoint inhibitor, a MUC-1 inhibitor, a CD40 activator, an IDO inhibitor, and an OX86 agonists. In some embodiments, the treatment for the patient determined to have a low level of CT45 expression excludes chemotherapy. In some embodiments, the treatment for the patient determined to have a low level of CT45 expression comprises a PP4 inhibitor and a DNA damaging agent. In some embodiments, the PP4 inhibitor comprises a CT45 peptide or polypeptide. In some embodiments, the DNA methyltransferase inhibitor comprises 5-aza-2'-deoxycytidine. In some embodiments, the treatment for the patient determined to have a low level of CT45 expression comprises a DNA methyltransferase inhibitor and a DNA damaging agent. In some embodiments, the treatment for the patient determined to have a low expression level of CT45 comprises administration of a DNA methyltransferase inhibitor. In some embodiments, the method further comprises administration of a chemotherapeutic after administration of the DNA methyltransferase inhibitor. In some embodiments, the DNA methyltransferase inhibitor is decitabine. In some embodiments, the DNA methyltransferase inhibitor is azacitidine.

A further aspect relates to a method for determining whether a patient having ovarian cancer will be chemosensitive and/or is likely to have disease-free survival, the method comprising: determining that the patient will be chemosensitive and/or is likely to have disease-free survival when the expression level of CT45 in a cancerous sample from the patient is determined to be elevated compared to the expression level of CT45 in a non-cancerous sample; or determining that the patient will be chemoresistant or develop chemoresistance and/or is not likely to have disease-free survival when the expression level of CT45 in a cancerous sample from the patient is determined to be not significantly different or lower than the expression level of CT45 in a non-cancerous sample. In some embodiments, the method further comprises measuring the expression level of CT45 in a cancerous sample from the patient. In some embodiments, the method further comprises comparing the expression level of CT45 in the cancerous sample from the patient to a control level of expression. In some embodiments, the method further comprises comparing the level of expression of CT45 in the biological sample from the patient to a cut-off value. In some embodiments, the method further comprises treating the patient determined to be chemosensitive with a chemotherapeutic agent. In some embodiments, the chemotherapeutic agent is a DNA damaging agent. In some embodiments, the DNA damaging agent is a platinum-containing compound. In some embodiments, the compound is cisplatin, carboplatin, oxaliplatin, nedaplatin, triplatin tetranitrate, phenanthriplatin, picoplatin, or satraplatin. In some embodiments, the ovarian cancer is HGSOC. In some embodiments, the method further comprises treating the patient determined to be chemosensitive with a DNA methyltransferase inhibitor. In some embodiments, the method further comprises administration of a chemotherapeutic after administration of the DNA methyltransferase inhibitor. In some embodiments, the DNA methyltransferase inhibitor is decitabine. In some embodiments, the DNA methyltransferase inhibitor is azacitidine. In some embodiments, the method further comprises treating the patient determined to be chemoresistant or develop chemoresistance with a treatment regimen that excludes chemotherapy.

Further aspects of the disclosure relate to a kit comprising an agent for detecting CT45 expression. In some embodiments, the agent detects CT45 protein expression or mRNA expression. In some embodiments, the agent comprises one or more nucleic acid probes for amplification of a CT45 nucleic acid from a biological sample. In some embodiments, the agent is an antibody. In some embodiments, the agent is labeled. In some embodiments, the agent detects a polypeptide having a sequence comprising a sequence of one of SEQ ID NOS: 1-6 or 29-33 or a nucleotide encoding a polypeptide of SEQ ID NOS: 1-6 or 29-33.

In some embodiments of the methods described herein, the ovarian cancer is high-grade serous ovarian cancer (HGSOC). In some embodiments, the ovarian cancer is an epithelial cancer. In some embodiments, the ovarian cancer is a fallopian or peritoneal cancer.

In some embodiments, the method further comprises monitoring the patient for cancer under intensive surveillance after the patient has been classified as having a poor prognosis. In some embodiments, the method further comprises monitoring the patient for cancer under regular surveillance after the patient has been classified as having a favorable prognosis. In some embodiments, the method further comprises treating the patient for cancer under regular surveillance if the patient is classified as having a favorable prognosis.

Further aspects of the disclosure relate to a method for treating a patient with ovarian cancer comprising: administering to the patient a CT45 polypeptide. In some embodiments, the CT45 peptide comprises a polypeptide of any one of SEQ ID NOS: 7-28 or a polypeptide with at least 70% identity to a polypeptide of SEQ ID NOS: 7-28. In some embodiments, the method further comprises administration of a chemotherapeutic agent. In some embodiments, the chemotherapeutic agent is a DNA damaging agent. In some embodiments, the DNA damaging agent is a platinum-containing compound. In some embodiments, the compound is cisplatin, carboplatin, oxaliplatin, nedaplatin, triplatin tetranitrate, phenanthriplatin, picoplatin, or satraplatin. In some embodiments, the ovarian cancer comprises a CT45-low-expressing ovarian cancer. In some embodiments, the patient has been determined to have a CT45 low-expressing cancer.

Any of the methods described herein may be implemented on tangible computer-readable medium comprising computer-readable code that, when executed by a computer, causes the computer to perform one or more operations. In some embodiments, there is a tangible computer-readable medium comprising computer-readable code that, when executed by a computer, causes the computer to perform operations comprising: a) receiving information corresponding to the level of expression of CT45 in a cancer sample of a patient suspected of having or determined to have a cancer; and b) determining a difference value in the expression level of CT45 using the information corresponding to the level of expression of CT45 in the cancer sample as compared to a control or reference level that is normal or indicating favorable prognosis. In further embodiments, the receiving information comprises receiving the information corresponding to the expression level from a tangible data storage device.

In some embodiments, the method further comprises recording the classification or the expression level of CT45 in a tangible, computer-readable medium or a tangible data storage device. In some embodiments, the method further comprises reporting the classification or the expression level of CT45 to the patient, a health care payer, a physician, an insurance agent, or a tangible data storage device. In additional embodiments the medium further comprises computer-readable code that, when executed by a computer, causes the computer to perform one or more additional operations comprising sending information corresponding to the difference value to a tangible data storage device; calculating a prognosis score for the patient; classifying the patient as having a favorable prognosis or poor prognosis; or determining a management, surveillance or treatment plan for the patient.

In some embodiments, the prognosis score is expressed as a number that represents a probability of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% likelihood (or any range derivable therein) that a patient has a chance of poor survival or cancer recurrence or poor response to a particular treatment. Alternatively, the probability may be expressed generally in percentiles, quartiles, or deciles.

In some embodiments, determination of calculation of a diagnostic, prognostic, or risk score is performed by applying classification algorithms based on the expression values of biomarkers with differential expression p values of about, between about, or at most about 0.005, 0.006, 0.007, 0.008, 0.009, 0.01, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.03, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, 0.1, 0.2, 0.3, 0.4, 0.5, 0.6, 0.7, 0.8, 0.9 or higher (or any range derivable therein). In certain embodiments, the prognosis score is calculated using one or more statistically significantly differentially expressed biomarkers (either individually or as difference pairs), including expression or activity levels in a gene or protein corresponding to CT45.

In some embodiments, a polypeptide according to the current disclosure is or is at least 70%, 75%, 80%, 85%, 90%, 91%, 92%, 93%, 94%, 95%, 96%, 97%, 98%, or 99% identical or similar (or any derivable range therein) to a polypeptide described herein, such as SEQ ID NOS: 1-6 or 29-33. In some embodiments, the polypeptide comprises at least 3, 4, 5, 6, 7, 8, 9, 10, 11, 12, 13, 14, 15, 16, 17, 18, 19, 20, 25, 30, 35, 40, 50, 75, or 100 contiguous amino acids (or any derivable range therein) of a polypeptide described herein.

In some embodiments, a polypeptide of the disclosure comprises a polypeptide variant of SEQ ID NOS: 1-6 or 29-33, wherein the variant comprises amino acid substitutions at one or more amino acids at positions 1, 2, 3, 4, 5, 6, 7, 8, 9, 10, or 11 of SEQ ID NOS: 1-6 or 29-33. In some embodiments, a polypeptide of the disclosure comprises a polypeptide variant of SEQ ID NOS: 1-6 or 29-33, wherein the variant comprises one or more amino acid substitutions of a R, H, K, D, E, S, T, N, Q, C, U, G, P, A, V, I, L, M, F, Y, or W for the amino acid at position 1, 2, 3, 4, 5, 6, 7, 8, 9, 10, or 11 of SEQ ID NOS: 1-6 or 29-33.

In certain aspects the amino acid substitution can be any of the other 20 amino acids. In some embodiments, conservative amino acid substitutions can be specifically excluded from possible amino acid substitutions. In some embodiments, only non-conservative substitutions are included. In some embodiments, non-conservative amino acid substitutions can be specifically excluded from possible amino acid substitutions. In some embodiments, only conservative substitutions are included.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Embodiments concern determining that the level of expression or activity of CT45. In some embodiments, that level is compared to a control in order to determine whether the expression level or activity of CT45 is elevated as compared to the level in non-cancerous tissue. The control may be a non-cancerous tissue or it may be a cancerous tissue. If the control is a cancerous tissue a sample may be determined to have an elevated level of CT45 because the levels in the control and the patient sample are similar, such as within, at least or at most 1, 2, 3, or 4 standard deviations (or any range derivable therein) of one another.

In some embodiments, a low level of expression of CT45 comprises a level of expression that is within 1, 2, 3, 4, 5, 6, or 7 standard deviations from a non-cancerous control. In some embodiments, a low level of expression of CT45 comprises a level of expression that is less than 20, 15, 10, 5, 2, or 1% of a non-cancerous control. In some embodiments, a high level of expression of CT45 comprises a level of expression that is more than 10, 15, 20, 25, 30, 35, 40, 45, 50, 55, 60, 65, 70, 80, 90, 100, 200, 300, 400, 500, 1000, 5000, or 10000% control. In some embodiments, the low level of expression and/or the high level of expression is based on a cut-off value, and values below the cut-off correspond to a low level of expression, and values above the cut-off correspond to a high level of expression. In some embodiments, the cut-off is determined by a ROC analysis. In some embodiments, the cut-off is based on a ROC analysis, wherein the cut-off separates the populations of known patients into high and low-expressers with a p-value of less than 0.01, 0.001, 0.0001, or 0.00001 (or any derivable range therein) or an area under the curve (AUC) of greater than 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, or 1.0. In some embodiments, low-expressing CT45 cancers and high-expressing CT45 cancers are determined from control. For example, a low-expressing CT45 cancer may be determined to be low-expressing or classified as low-expressing when the level of CT45 expression in the cancer is within 0.1, 1, 2, 3, 4, 5, or 10 standard deviations from the level of expression in a non-cancerous tissue (such as ovarian tissue) or the level of expression of CT45 in cancer patients without disease-free survival, patients with a poor prognosis, and/or patients who have developed chemoresistance. A high-expressing CT45 cancer may be determined to be high-expressing or classified as high-expressing when the level of CT45 expression in the cancer is within 0.1, 1, 2, 3, 4, 5, or 10 standard deviations from the level of expression in cancer patients with disease-free survival, patients with a favorable prognosis, and/or patients who have not developed chemoresistance (or are determined to be chemosensitive).

In some embodiments, the cut-off value, low-expressing cancer, and/or high-expressing cancer is determined from immunofluorescence of the CT45 polypeptide. In some embodiments, the cut-off value is determined from a biological sample and is at least, at most, or exactly 0.1, 0.2, 0.3, 0.4, 0.5, 0.6, 0.7, 0.8, 0.9, 1, 1.1, 1.2, 1.3. 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3. 3.4, 3.5, 3.6, 3.7, 3.8, 3.9, 4.0, 4.1, 4.2, 4.3, 4.4, 4.5, 4.6, 4.7, 4.8, 4.9, 5.0, 5.15.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.4, 8.6, 8.7, 8.8, 8.9, 9.0, 9.1, 9.2, 9.3, 9.4, 9.5, 9.6, 9.7, 9.8, 9.9, or 10 pg/ml, ng/ml, µg/ml, pg/µl, ng/µl, or µg/µl (or any derivable range therein).

In some embodiments, the elevated level is at least 1, 1.5, 2, 2.5, 3, 3.5, 4, 4.5, 5, 5.5, 6, 7, 8, 9, 10, 12, 14, 16, 18, 20, 50, 100, 150, 200, 250, 500, or 1000 fold (or any derivable range therein) or at least 10, 20, 30, 40, 50, 60, 70, 80, 90, 100, 200, 300, 400, 500, 600, 700, 800, or 900%, or any derivable range therein.

Further aspects of the disclosure relate to a composition comprising a CT45 polypeptide and a chemotherapeutic agent. In some embodiments, the CT45 peptide comprises a polypeptide of any one of SEQ ID NOS: 7-28 or a polypeptide with at least 70% identity to a polypeptide of SEQ ID NOS: 7-28. In some embodiments, the chemotherapeutic agent is a DNA damaging agent. In some embodiments, the DNA damaging agent is a platinum-containing compound. In some embodiments, the compound is cisplatin, carboplatin, oxaliplatin, nedaplatin, triplatin tetranitrate, phenanthriplatin, picoplatin, or satraplatin. In some aspects, the disclosure relates to a composition comprising a DNA methylation inhibitor and a platinum containing chemotherapeutic agent cus as cisplatin, carboplatin, oxaliplatin, nedaplatin, triplatin tetranitrate, phenanthriplatin, picoplatin, or satraplatin. In some embodiments, the disclosure relates to a composition comprising decitabine and a a platinum containing chemotherapeutic agent such as cisplatin, carboplatin, oxaliplatin, nedaplatin, triplatin tetranitrate, phenanthriplatin, picoplatin, or satraplatin. In some embodiment, the disclosure relates to a composition comprising decitabine and carboplatin. In some embodiments, the disclosure relates to a composition comprising a CT45 polypeptide and carboplatin. The compositions of the disclosure may be used in any of the methods described herein.

The terms "ameliorating," "inhibiting," or "reducing," or any variation of these terms, when used in the claims and/or the specification includes any measurable decrease or complete inhibition to achieve a desired result.

As used herein, "increased expression" or "decreased expression" refers to an expression level of a biomarker in the subject's sample as compared to a reference level representing the same biomarker or a different biomarker. In certain aspects, the reference level may be a reference level of expression from a normal sample, such as a non-cancerous tissue from the same subject, particularly normal mucosa, or a sample from a different subject that does not have the cancer to be treated. Alternatively, the reference level may be a reference level of expression from a different subject or group of subjects, such as a reference level of expression from a subject or a group of subjects that have a favorable prognosis of cancer, such as having at most 20, 30, 40, or 50, 60, 70, 80% recurrence risk (or any range derivable therefrom) or at least 50, 60, 70, 80, or 90% survival chance (or any range derivable therefrom) of cancer relative to a group of poor prognosis or favorable prognosis subjects or a combination thereof. Alternatively, the reference level may be a reference level of expression from a subject or a group of subjects that has a poor prognosis, such as having a high recurrence risk of more than 50, 60, 70, 80, or 90 (or any range derivable therefrom) or at most 20, 30, 40, or 50, 60, 70, 80% survival chance (or any range derivable therefrom) relative to a group of poor prognosis or favorable prognosis subjects or a combination thereof. The combined group may be randomly selected or may be a group of clinical trial subjects, subjects in a particular geographic area, an age group, a gender group, or a stage of colorectal cancer, or any group based on one or more predetermined classification criteria, like inclusion or exclusion of patients that have favorable or poor prognosis.

A person of ordinary skill in the art understands that an expression level from a test subject may be determined to have an elevated level of expression, a similar level of expression or a decreased level of expression compared to a reference level.

"Diagnosis" may refer to the process of attempting to determine or identify a possible disease or disorder, or to the opinion reached by this process. From the point of view of statistics the diagnostic procedure may involve classification tests.

"Prognosis" may refer to a prediction of how a patient will progress, and whether there is a chance of recovery. "Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. Prognosis may also include prediction of favorable responses to cancer treatments, such as a conventional cancer therapy.

A "subject," "individual" or "patient" is used interchangeably herein and refers to a vertebrate, for example a primate, a mammal or preferably a human. Mammals include, but are not limited to equines, canines, bovines, ovines, murines, rats, simians, humans, farm animals, sport animals and pets. In some embodiments, the subject is a human subject.

In some embodiments, the method further comprises administration of pain medication and/or additional therapeutics. In some embodiments, the method further comprises administration of a traditional therapeutic for cancer such as chemotherapy and/or surgery. In some embodiments, the additional therapeutic is one known in the art and/or described herein.

Use of the one or more compositions may be employed based on methods described herein. Use of one or more compositions may be employed in the preparation of medicaments for treatments according to the methods described herein. Other embodiments are discussed throughout this application. Any embodiment discussed with respect to one aspect of the disclosure applies to other aspects of the disclosure as well and vice versa. The embodiments in the Example section are understood to be embodiments that are applicable to all aspects of the technology described herein.

As used herein, "treatment" or "therapy" is an approach for obtaining beneficial or desired clinical results. This includes: reduce the alleviation of symptoms, the reduction of inflammation, the inhibition of cancer cell growth, and/or the reduction of tumor size. In some embodiments, the term treatment refers to the inhibition or reduction of cancer cell proliferation in a subject having cancer.

The term "therapeutically effective amount" refers to an amount of the drug that treats or inhibits cancer in the subject. In some embodiments, the therapeutically effective amount inhibits at least or at most or exactly 100, 99, 98, 96, 94, 92, 90, 85, 80, 75, 70, 65, 60, 55, 50, 40, 30, 20, or 10%, or any derivable range therein, of CT45 activity.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used in this specification and the claim(s), when referring to a particular therapeutic drug regimen, the words "consisting essentially of" includes therapeutic drug remiments including, as active ingredients, only the recited active ingredients and excludes any active ingredients not recited.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-G Proteomics identifies CT45 expression to predict long-term survival in HGSOC. a, Summary of the shotgun proteomics workflow applied to FFPE biobank specimens from ovarian cancer patients. Following tissue lysis and homogenization, purified proteins were digested by trypsin and desalted peptides separated by ultra-high performance liquid chromatography. All samples were measured in single-run analysis using a Q Exactive mass spectrometer. Label-free proteome quantification was achieved with the MaxQuant software. b, Number of quantified proteins per patient (median=7,634 proteins) and total (9,016 proteins). c, Volcano plot of chemotherapy resistant versus sensitive patient proteomes. Expression fold changes (t-test difference) are shown on the X-axis and plotted against the t-test p-value (−log 10, permutation-based FDR corrected). Dashed lines indicate significance threshold (FDR<0.05, S0=2). The cancer-testis antigen CT45 is significantly higher expressed in the chemotherapy sensitive patient group. d, Correlation analysis of disease-free survival time versus CT45 protein expression (log 2) for 25 HGSOC patients. e, f, Kaplan-Meier survival analysis based on CT45 staining scores from ovarian cancer TMAs for disease-free survival (e) and overall survival (f). Advanced stage HGSOC patients comparing a staining score of 0 (N=82) versus 1+ (N=42). g, Kaplan-Meier survival analysis based on RNA-seq TCGA data. Overall survival of patients with low CT45 (N=229) versus high CT45 expression (N=76). Significance was determined using the log-rank test.

FIG. 2A-C. CT45 is an antigenic target in ovarian cancer patients. a, Percent of CD8+ tumor associated T cells from ascites staining positive for Ki67 (upper) and IFN-γ and IL-2 (lower) following stimulation with CT45-derived peptides. EBV is a positive control peptide and HIV is a negative control peptide. The amino acid sequences on the x-axis of the bottom graph correspond to SEQ ID NOS: 1-5, respectively. b, Log 2 intensities of CT45 peptides as detected my mass spectrometry from HLA-I pulldowns following DAC treatment in SKOV3ip1 cells. The amino acid sequences in the figure legend correspond to SEQ ID NOS: 32, 2, and 33, respectively, top to bottom. c, Percent of CD8+ tumor associated T cells from ascites staining positive for Ki67 (upper) and IFN-γ and IL-2 (lower) following stimulation with CT45-derived peptides identified after DAC treatment. EBV is a positive control peptide and HIV is a negative control peptide The amino acid sequences on the x-axis of the bottom graph correspond to SEQ ID NOS: 32, 2, and 33, respectively.

Figure 4:
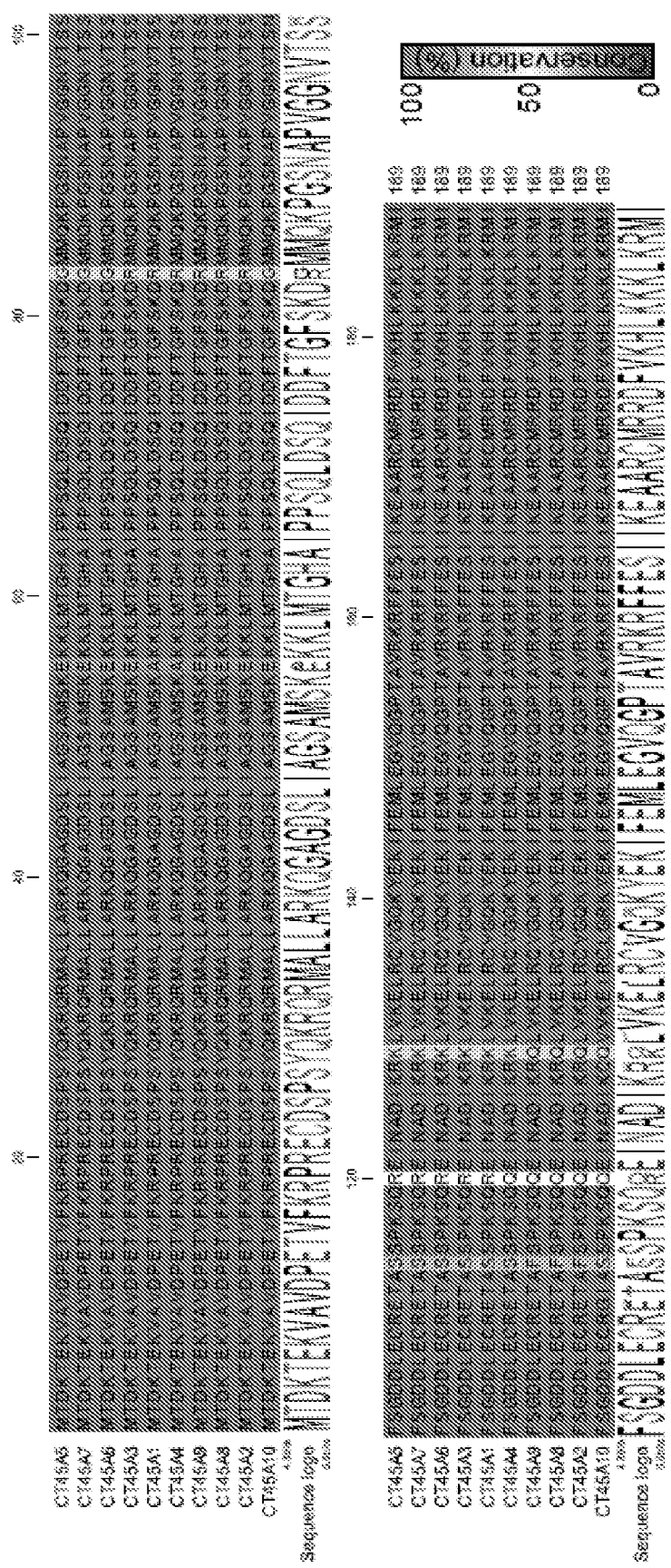

FIG. 4. CT45 gene homology and staining validation. Amino acid alignment of the 10 members of the CT45 gene family. The sequences of each variant corresponds to SEQ ID NO:7-17, respectively, top to bottom.

FIG. 5A-D. HLA-I peptidemics reveals presentation of CT45-derived peptides. a, Western blot of CT45 protein expression in 8 ovarian cancer cell lines. b, qRT-PCR of CT45 RNA expression in 7 ovarian cancer cell lines. c, Schematic of immuno-peptidomics strategy to identify HLA-I binding peptides. HLA-I complexes with peptides are pulled down with an antibody specific for HLA-I. Peptides are eluted away from the HLA complex and identified by mass spectrometry. f, Stimulation of CD8+ tumor infiltrating HLA-A*11:01+ T cells from omental tumor with CT45-derived peptides Percent of T-cells staining positive for CD69 (left) and IFN-γ (right) following. The amino acid sequences on the x-axis at the bottom of both of the graphs correspond to SEQ ID NOS: 1-5, respectively for each graph.

FIG. 6A-B. CT45-derived peptides are presented after DAC treatment. a, Western blot of CT45 protein expression in SKOV3ip1 (HLA-A*03:01, 68:01) following DAC treatment. 59M is the positive control. b, Histogram of the identified peptide lengths from the DAC treated SKOV3ip1 cell line.

Figure 7B:
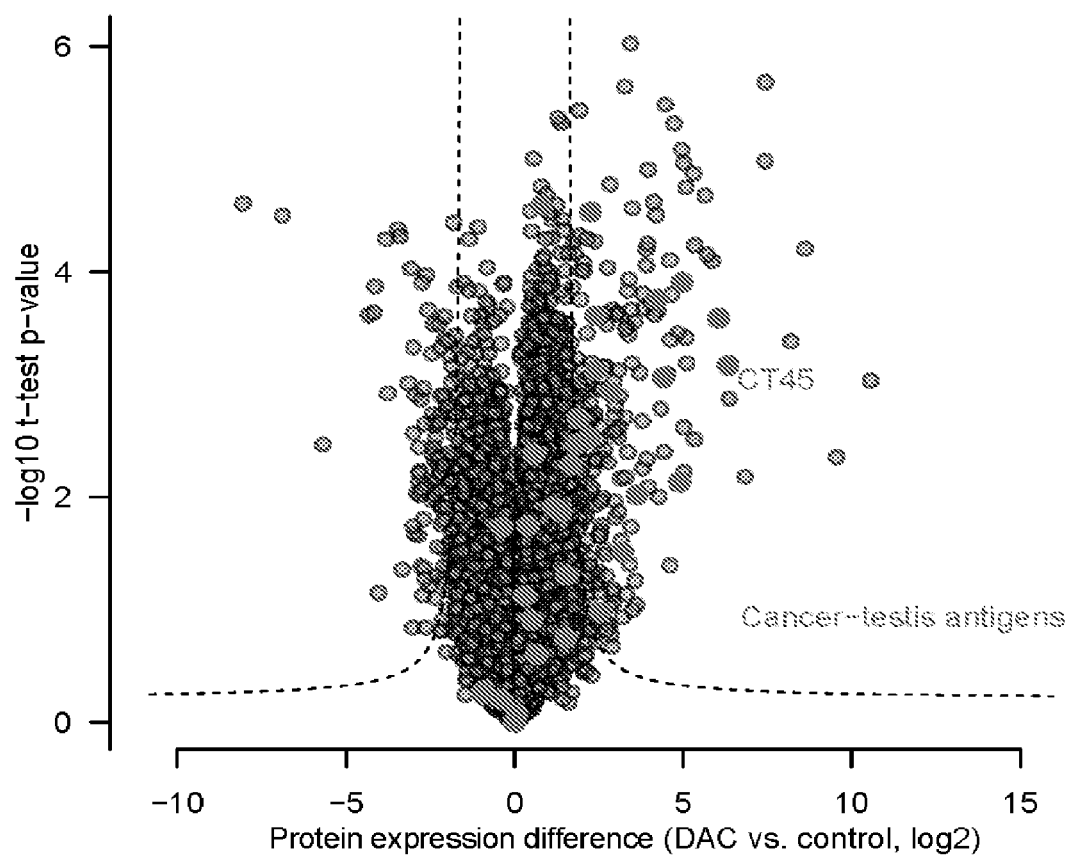

FIG. 7A-B. DAC upregulates cancer testis antigens. a, MTT of Kuramochi cells treated with DAC (5'-aza) and carboplatin. b, Volcano plot of control SKOV3ip1 versus DAC treated SKOV3ip1 proteomes. Cancer-testis antigens are shown in light grey.

FIG. 8A-B. CT45 sensitizes cancer cells to carboplatin. a, Western blot of CT45 expression in ovarian cancer cell lines transduced with a CT45A5 lentivirus. b, Proliferation of OVCAR5 control (V5) or CT45 expressing cells with increasing concentrations of carboplatin.

FIG. 9 shows the immunogenicity of CT45 polypeptides. The FACS analysis demonstrates that T cells directly bind to the HLA complex containing CT45 peptides. The amino acid sequences above the second and third graph on the top correspond to SEQ ID NOS: 1 and 3, respectively and the sequences above the second and third graph on the bottom correspond to SEQ ID NOS: 1 and 3, respectively.

FIG. 10A-D. Proteomics identifies CT45 expression to predict long-term survival in HGSOC. A, Summary of the shotgun proteomics workflow applied to FFPE biobank specimens from ovarian cancer patients. Following tissue lysis and homogenization, purified proteins were digested and analyzed in single-run HPLC-MS using a Q Exactive mass spectrometer. Data were analyzed and quantified in MaxQuant. B, Volcano plot of chemotherapy resistant versus sensitive patient proteomes. Expression fold changes are plotted against the t-test p-value. Dashed lines indicate the significance threshold (FDR<0.05, $s_0$=2). C, Immunohistochemistry for CT45 and corresponding H&E staining in serial sections of tumor from 3 prepresentative patients. D, Kaplan-Meier survival analysis based on CT45 staining scores for ovarian cancer TMAs for disease-free survival. Advanced stage HGSOC patients comparing in a staining score of 0 (N=82) versus 1+ (N=42).

FIG. 11A-F. CT45 is a native tumor antigen. A, Predicted binding affinities (NetMHC4.0) for HLA class I peptides of CT45 with a length of 8-11 amino acids. Affinities are plotted on the y-axis as % rank-1. Weak affinity cut-off: % rank <2, high affinity cut-off: % rank <0.5. Peptides identified by MS are shown. The sequences in the top and bottom graphs correspond to SEQ ID NOS: 1, 3, 2, 4, and 5, left to right, respectively. B, Volcano plot of the proteomic comparison between 5-aza-2'-deoxycytidine (DAC) treated and control SKOV3iP1 ovarian cancer cells. Protein fold change (t-test difference, log 2) is plotted against the t-test p-value ($-\log_{10}$). Significance thresholds are indicated by dashed lines (FDR<0.01). Cancer testis antigens including CT45 are highlighted. C, HLA-I peptide intensity ratio from immunopeptidomics of DAC treated versus control SKO2iP1 ovarian cancer cells, plotted against the ranked peptide ratio. CT45 peptides are shown. The sequences in the graph corresponds to SEQ ID NOS: 32, 2, and 33, top to bottom, respectively. D, Staining for Ki-67 and IFN-γ of CD8+ T cells (A-11:01) after stimulation with two CT45 peptides (AVDPETVFK (SEQ ID NO: 1) and GVQGPTAVRK (SEQ ID NO:3)) or one HIV negative control peptide analyzed with flow cytometry. E, Tetramer staining of A-11:01 or A-03:01 CD8+ T cells with two CT45 tetramers (AVDPETVFK (SEQ ID NO:1) and GVQGPTAVRK (SEQ ID NO:3)) and one HIV negative control tetramer analyzed with flow cytometry. F, Lysis of HLA-A11:01 positive 59M cell line by CD8+ effector T cells (A-11:01) at indicated effector:target ratios using a chromium release assay. Data are means+/−s.d. from two independent experiments. The sequences in the figure legend correspond to SEQ ID NOS: 1 and 3, top to bottom, respectively.

FIG. 12A-F. CT45 mediates chemotherapy sensitivity. A, Clonogenic survival assay of the ovarian cancer cell line OVCAR5 stably overexpressing CT45 or control vector after carboplatin (5 μM) treatment. Dots represent mean values from three independent experiments. Error bars show s.e.m. for each group. Representative images are shown above bars. B, Growth of OVCAR5-V5 (control plasmid) and OVCAR5-V5-CT45 tumors (N=5-8) over time during treatment with carboplatin (20 mg/kg). Data are means+/−s.e.m. for each group. C, Interaction proteomics screen in OVCAR5 cells stably overexpressing FLAG-tagged CT45. Protein enrichment (t-test difference) was calculated over the corresponding control cell line (FLAG tag alone) and plotted against the t-test p-value ($-\log_{10}$). Dashed lines indicate significance thresholds. The bait protein CT45 and members of the PP4 complex are highlighted. Results represent 3 replicates per experiment group P<0.01. D, Western blot of immunoprecipitated V5-tagged CT45 protein. The co-enriched members of the protein phosphatase 4 complex, PP4R3α, PP4R3β, and PP4C, are shown. E, Western blot of cleaved caspase-3, γH2AX, and CT45 following treatment of carboplatin (5 μM) and paclitaxel (1.5 nM). Day 5. F, Tail moment following carboplatin treatment at day 5 using a comet assay. Data are means+s.e.m. of 4 independent replicates (right panel). Representative images of comet assays are shown. OVCAR5 cells were treated with 5 μM carboplatin and COV318 were treated with 2 μM carboplatin.

FIG. 13A-I. CT45 interferes with chromatin dynamics after DNA damage. A, Western blot analysis of OVCAR5 and OVKATE cell line pairs treated with carboplatin (5 μM). Day 3. B, Immunofluorescence staining of KAP1-S824 γH2AX and DAPI in OVCAR5-V5 and OVCAR5-V5-CT45 cell line pair with or without carboplatin treatment (5 μM) at day 3, 5, and 7. Data are means+/−s.e.m. of 5 independent replicates (right panel). Representative cells are shown left. C, CT45 positive 59M cells were collected and processed for a chromatin segregation assay as detailed in the Methods. PP4 complex members, KAP1, and HDAC2 were detected by western blot. D, Volcano plot of chromatin-immunoprecipitation mass spectrometry (ChIP-MS) results for the V5-tag in OVCAR5-V5-CT45 vs. OVCAR5-V5 cell line.

Fold enrichment of V5-tagged CT45 over control cell line (V5 tag alone) is plotted against the t-test p-value ($-\log_{10}$). Dashed lines indicate significance thresholds (FDR<0.01, $s_0$=2). E, Pathway enrichment analysis of proteins significantly co-enriched with CT45 (right side of volcano plot in panel d). Most significant pathways are ranked by enrichment false-discovery rate. F, Fold change in nuclear sizes of OVCAR5-V5-CT45 and OVCAR5-V5 cells at day 5 with carboplatin (5 μM) treatment normalized to untreated cells. Representative DAPI images are shown in upper panel. Bar plots represent nuclear sizes from 5 independent experiments. Scale ar=10 μM. Data are means+/-s.e.m. G,H, OVCAR5-V5-CT45 and OVCAR5-V5 cells were collected and processed for the micrococcal nuclease (Mnase) assay as described in the Methods. Results are shown for untreated control samples at day 3 and day 3, 5, and 7 with carboplatin (5 μM) treatment. DNA size profiles are illustrated in H. I, Proposed model of CT45 mediating chemosensitivity and long-term survival in metastatic HGSOC.

FIG. 14A-D Patient characteristics of proteomic cohort and proteomic depth per specimen. a, Clinico-pathologic parameters for the resistant and sensitive patients analyzed by proteomics. b, Proteomic depth per patient. Samples were measured as technical duplicate. c, Dynamic range of protein abundance of all quantified proteins. d, Correlation matrix of all measured samples based on Pearson correlation values. The proteomic comparison of independently prepared tissue of the same tumor is highlighted.

Figure 15:
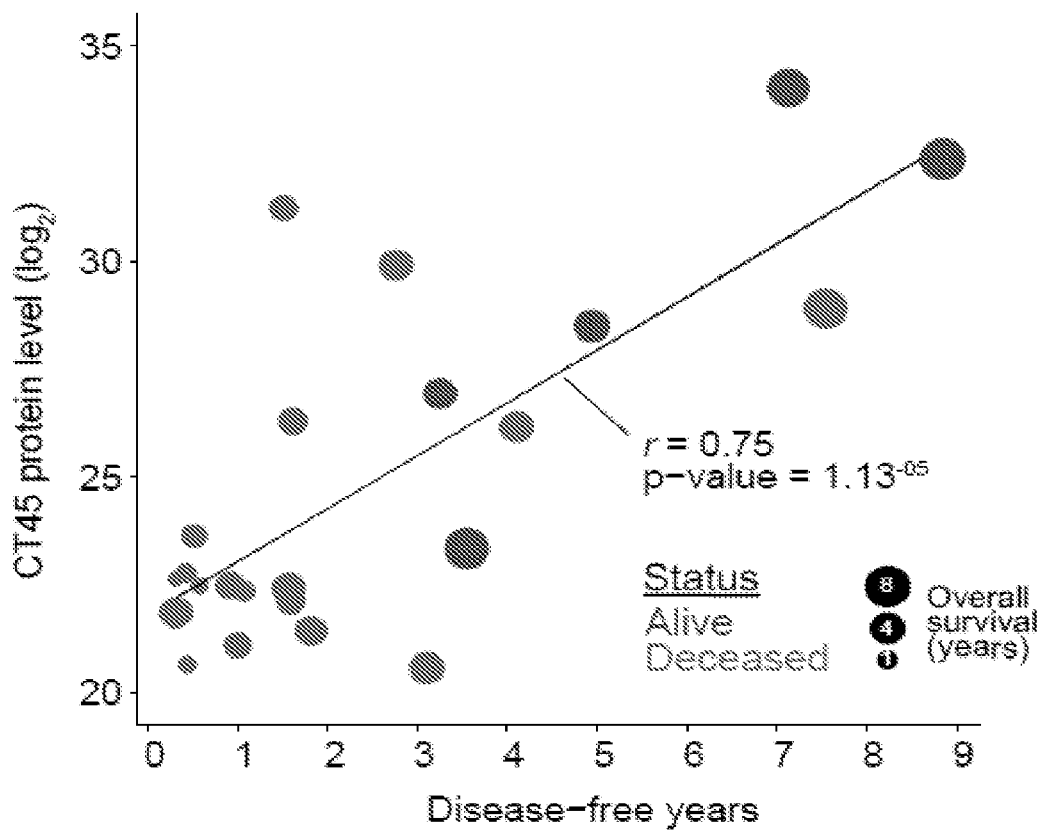

FIG. 15. CT45 gene homology and staining validation. a, Correlation analysis of disease-free survival time versus CT45 protein expression (log 2) for 25 HGSOC patients. Patients highlighted in dark grey were alive at the time of analysis.

Figure 16B:
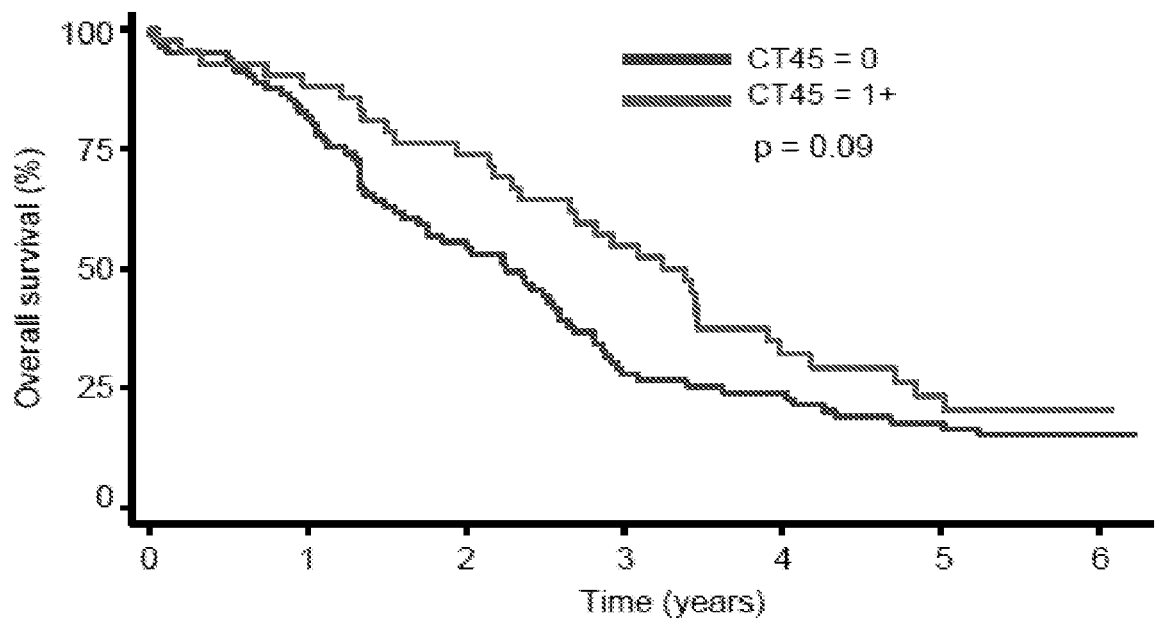

FIG. 16A-B. Patient characteristics of tissue microarray validation cohort. a, Clinico-pathologic parameters for patients with advanced stage serous papillary ovarian cancer included in the TMA validation cohort. Tumors were stained for CT45 and the staining was scored 0-3. b, Kaplan-Meier survival analysis for overall survival based on CT45 staining scores from ovarian cancer TMAs. Advanced stage HGSOC patients comparing a staining score of 0 (N=82) versus 1+ (N=42) are compared.

FIG. 17A-H. HLA-I peptidomics reveals presentation of CT45-derived peptides. a, Western blot of CT45 protein expression in 8 ovarian cancer cell lines. b, Schematic of immuno-peptidomics strategy to identify HLA-I binding peptides. HLA-I receptors with peptide complexes are pulled down with an antibody specific for HLA-I. Peptides are eluted from the HLA complex and identified by mass spectrometry. c, Histogram of the identified peptide lengths from the 59M cell line (length 8-11 amino acids) consistent with peptides that bind to HLA-I receptors. d, CT45A1 protein sequence (SEQ ID NO:11) and CT45 peptides of SEQ ID NOS: 29, 30, 3, and 31, top to bottom, respectively. Identified HLA-I peptides are underlined. e, Identified consensus clusters based on the GibbsCluster-1.0 tool for all identified 9-mer peptides (4,017) f, Binding motifs. HLA-I consensus binding motifs for the two largest clusters in e (SEQ ID NO:36-37). The A11:01 motif is similar to A3:01. g-h, Comparison of MS/MS scans from experimentally identified HLA-I peptides (upper panel) and synthetic versions of the same peptides (lower panel). SEQ ID NOS: 1 and 3 are shown in G top to bottom, respectively. SEQ ID NO: 4 is shown in H.

FIG. 18A-E. CT45-derived peptides are presented after DAC treatment. a, Western blot of CT45 protein expression in SKOV3ip1 (HLA-A*03:01, 68:01) following DAC treatment. 59M serves as positive control. b, Histogram of the identified peptide lengths from the DAC treated SKOV3ip1 cell line. c, Identified consensus clusters based on the GibbsCluster tool for all identified 9-mer peptides (5,146). d, HLA-I consensus binding motifs for the two largest clusters identified in c (SEQ ID NO:38-39). The A68:01 motif is similar to A3:01. e, Stimulation of CD8+ tumor infiltrating HLA-A*03:01+ T cells isolated from ascites with CT45-derived peptides. Staining for Ki-67 and IFN-γ of CD8+ T cells (A-03:01) after stimulation with 3 CT45 peptides (EGVQGPTAVR (SEQ ID NO:32), GVQGPTAVR (SEQ ID NO:2), and VAVDPETVFKR (SEQ ID NO:33)) or an EBV positive control or HIV negative control peptide analyzed with flow cytometry.

FIG. 19A-F. CT45 sensitizes cancer cells to carboplatin. a, MTT of SKOV3ip1 cells with or without 500 nM DAC treated with increasing doses of carboplatin. Cells were pretreated with 500 nM DAC for 72 hr then cultured for 4 days and treated with carboplatin on day 7. The MTT was performed after 72 hr with carboplatin treatment. b, Western blot of CT45 expression in ovarian cancer cell lines transduced with a CT45A5 lentivirus. c, Proliferation of OVCAR5 control (V5) or CT45 expressing cells with increasing concentrations of carboplatin. d, Cell cycle analysis of OVCAR5 control (V5) or CT45 expressing cells stained with propidium iodide. e, Clonogenic survival assay of the ovarian cancer cell line OVKATE stably overexpressing CT45 or control. Dots represent mean values from three independent experiments. Error bars show s.e.m. for each group. f, Interaction proteomics screen in the ovarian cancer cell line COV318 stably over-expressing V5-tagged CT45. Protein enrichment (t-test difference) is calculated over the corresponding control cell line (V5 tag alone) and plotted against the t-test p-value ($-\log_{10}$). Dashed lines indicate significance thresholds (p<0.005, s0=3). The bait protein CT45 and members of the protein phosphatase 4 complex are highlighted. Results represent 3 replicates per experiment group.

FIG. 20A-E CT45 is chromatin-bound independent of DNA damage. a, Chromatin fractionation of the OVCAR5-V5-CT45 cell line. b, Chromatin fractionation of the OVCAR5-V5-CT45 cell line carboplatin c, ChIP-MS results targeting V5-tagged CT45 in the OVCAR5-V5-CT45 cell line±carboplatin. Fold enrichment is calculated over an IgG control antibody. The bait protein CT45 and members of the protein phosphatase 4 complex are highlighted. Results represent 3 replicates per experiment group. d, e, ChIP-MS results targeting KAP1 in the OVCAR5 cell line pair (d), and the 59M cell line (e). Protein enrichment (t-test difference) is calculated over the corresponding control (V5 control cell line for d or an IgG control antibody for e, and plotted against the t-test p-value ($-\log_{10}$).

Figure 21:
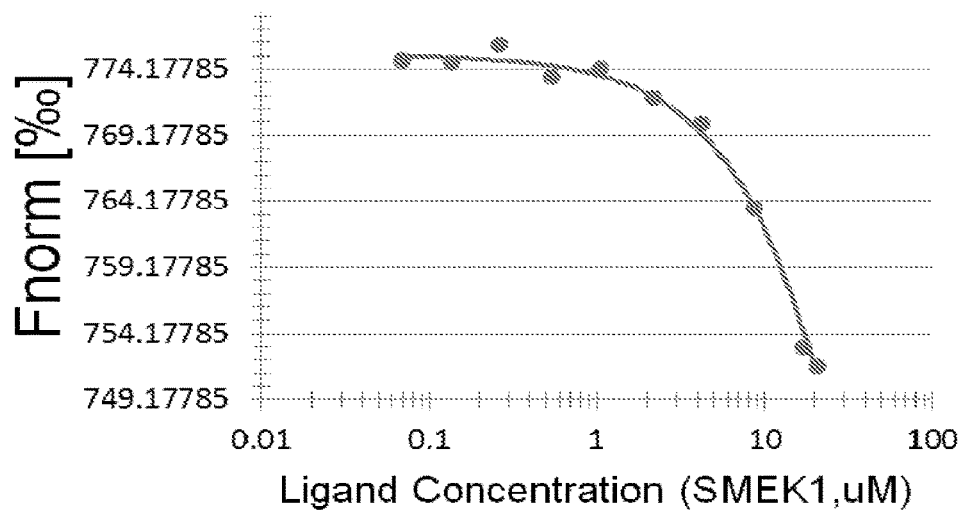

FIG. 21. CT45 is a direct interactor of the PP4 complex. Shown is a dose response chart of the concentration dependent binding of recombinant PP43Ra to recombinant CT45 as measured by microscale thermophoresis.

Figure 22A:
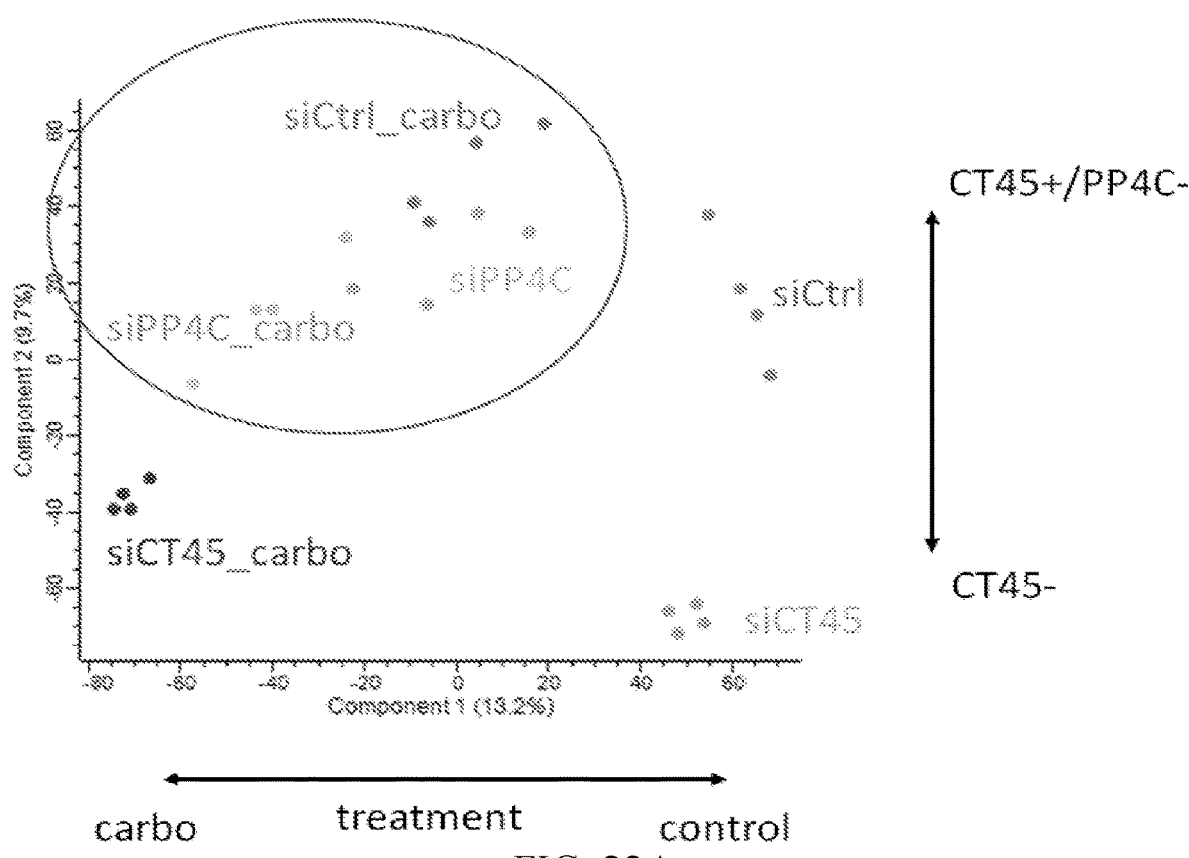
Figure 22B:
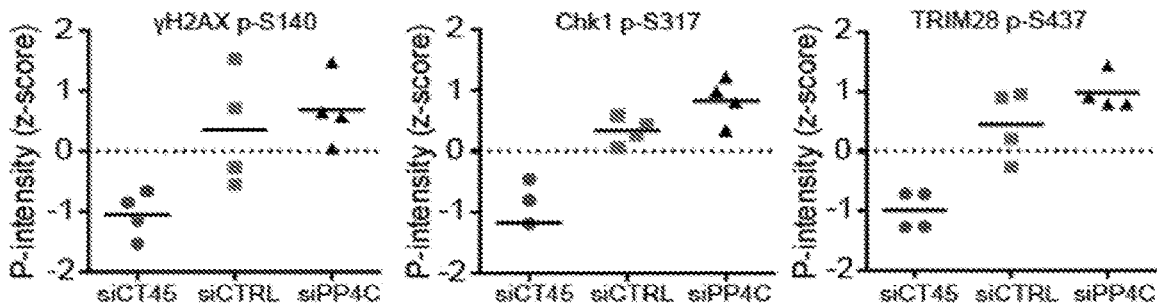

FIG. 22A-B. CT45 is a direct interactor of the PP4 complex. a. Principal Principal component analysis of a global phosphoproteome analysis (>9.000 phosphorylation sites) in Ctrl siRNA, PP4C siRNA or CT45 siRNA treated cells+/-carboplatin. CT45 expressing cells (siCtrl) cluster closer to PP4C deficient cells (siPP4C) in component 2 indicating more similar phosphosignaling in comparison to siCT45 cells. b. Example of known PP4 regulated phosphor sites-known PP4 target sites such as TRIM28-S473 and γH2AX-S139 are higher in PP4 knockdown or CT45 expressing cells indicating an inhibitory function of CT45 on PP4.

Figure 23:
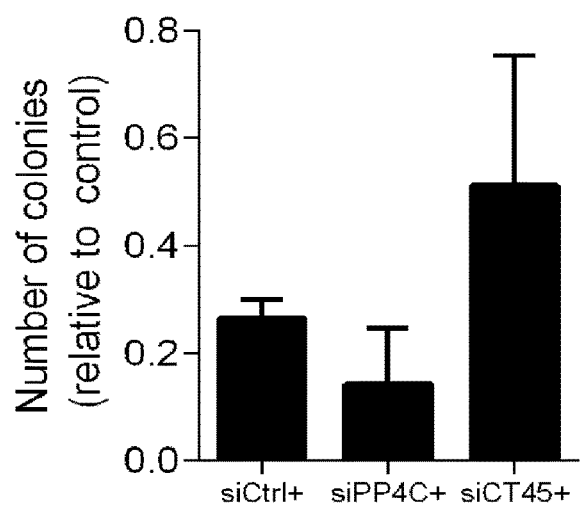

FIG. 23. Cell deficient in PP4 or expressing the endogenous PP4 inhibitor CT45 are hypersensitive to carboplatin treatment. Shown are colony assay results of carboplatin treated 59M cells transfected with a control siRNA, PP4C siRNA or CT45 siRNA. Colony numbers are normalized to untreated cells of each siRNA.

Figure 24A:
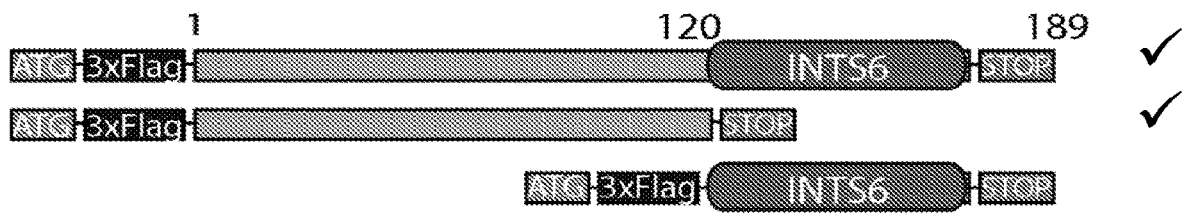

FIG. 24A-C. CT45 interaction with PP4 complex. a. Deletion mutants of CT45 identified the N-terminal part of CT45 as the interacting domain. b. Interaction proteomics screen in OVCAR5 cells overexpressing full-length CT45, N-terminal CT45, C-terminal CT45 or GFP tag alone. Plotted are protein intensities of the co-purified PP4 complex members. c. Western blot analysis of the immunoprecipitates from OVCAR5 cells overexpressing full-length CT45, N-terminal CT45, C-terminal CT45 or tag alone. The PP4 complex is co-purified with full-length or Nterm CT45.

DETAILED DESCRIPTION OF THE INVENTION

Using state of the art proteomics, the inventors identified CT45 as an independent prognostic indicator associated with chemosensitivity and long term survival for patients with an advanced stage epithelial ovarian cancer such as HGSOC. Ovarian cancer has been extensively studied at the genomic level and is characterized by widespread copy number variations with infrequent recurrent mutations beyond TP53, BRCA1 and BRCA26. Roughly half of HGSOCs also harbor deficiencies in homologous recombination DNA repair, which contributes to platinum sensitivity. The identification of CT45 as another driver of chemosensitivity fits well with the inherent nature of the disease. Analysis of CT45 expression using tissue microarrays (TMAs) showed no difference in CT45 expression between the ovarian tumour and the omental metastasis which would suggest that methylation changes occur early on in disease progression. Furthermore, it was found that some patients with high CT45 expression still had chemosensitive disease upon recurrence that was successfully retreated with platinum therapy suggesting that CT45 persists in recurrent disease.

I. Immunotherapies

Immunotherapy is the treatment of disease by inducing, enhancing, or suppressing an immune response. Immunotherapies designed to elicit or amplify an immune response are classified as activation immunotherapies, while immunotherapies that reduce or suppress are classified as suppression immunotherapies.

In cell-based immunotherapies, immune effector cells such as lymphocytes, macrophages, dendritic cells, natural killer cells (NK Cell), cytotoxic T lymphocytes (CTL), etc., work together to defend the body against cancer by targeting abnormal antigens expressed on the surface of tumor cells. Therapies such as granulocyte colony-stimulating factor (G-CSF), interferons, imiquimod, cellular membrane fractions from bacteria, IL-2, IL-7, IL-12, various chemokines, synthetic cytosine phosphate-guanosine (CpG) oligodeoxynucleotides, and glucans may also be used in the methods described herein.

Cancer immunotherapy attempts to stimulate the immune system to destroy tumors. A variety of strategies are in use or are undergoing research and testing. In some embodiments, the methods comprise or further comprise the extraction of immune cells (e.g. G-CSF lymphocytes) from the blood and expansion of said immune cells in vitro against a tumour antigen before reinjecting the cells with appropriate stimulatory cytokines. The cells then destroy the tumor cells that express the antigen. In some embodiments, an immune enhancement cream (imiquimod) which produces interferon, may be used.

Methods of the disclosure include immunotherapeutic compositions targeting CT45 antigens. The compositions may be used for in vivo, in vitro, or ex vivo administration. For example, the composition may be useful as cancer vaccines.

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject, including administrations.

In certain aspects of the present disclosure, the compositions may be administered either in vitro, ex vivo, or in vivo. In certain in vitro embodiments, autologous T cells are incubated and used in the methods described herein. The cells can be used for in vitro analysis, and/or for ex vivo administration.

The route of administration of the immune cell may be, for example, intratumoral, intracutaneous, subcutaneous, intravenous, intralymphatic, and intraperitoneal administrations. In some embodiments, the administration is intratumoral or intrapymphatic. In some embodiments, the immune cells are administered directly into a cancer tissue or a lymph node.

The origin of the naive T cells is not specifically limited and it may be derived from, for example, peripheral blood of a vertebrate animal. The naive T cell used may be CD8-positive cells or CD4-positive cells isolated from a PBMC fraction. In some embodiments, the naive T cells are CD8-positive cells or CD4-positive cells mixed with other cells and components without being isolated from the PBMC fraction in terms of the efficiency of inducing CTLs. For example, when cells of a PBMC fraction are cultured in a medium supplemented with serum and tumor antigen, the PBMCs differentiate into dendritic cell precursors. The dendritic cell precursors then bind to the peptide and differentiate into dendritic cells as the antigen-presenting cells presenting this peptide/tumor antigen. The antigen-presenting cells stimulate the CD8-positive T cells in the PBMCs to differentiate them into CTLs. Thus, the CTLs capable of recognizing the added peptide can be obtained. The CTLs thus obtained may be isolated and used as the cancer vaccine as they are. Alternatively, they may be cultured further in the presence of interleukin such as IL-2, the antigen-presenting cell, and tumor antigen before used as the cancer vaccine. The route of their administration is not specifically limited and examples include intracutaneous, subcutaneous, intravenous, and intratumoral administrations.

A. Dendritic Cell-Based Pump-Priming

Dendritic cells (DC) can be stimulated to activate a cytotoxic response towards an antigen. Dendritic cells, a type of antigen presenting cell, are harvested from a patient. These cells are then either pulsed with an antigen or transfected with a viral vector comprising nucleic acids encoding for the antigen, causing them to express and display the antigen. In some embodiments, the antigen is a peptide comprising or consisting of, or having sequence identity to a sequence of one or more of SEQ ID NO:1-6 or 29-33. Upon transfusion into the patient these activated cells present the antigen to the effector lymphocytes (CD4+ helper T cells, cytotoxic CD8+ T cells and B cells). This initiates a cytotoxic response against tumor cells expressing the antigen (against which the adaptive response has now been primed).

Physiologically, human DC are mainly localised in tissue and represent only a small portion of less than 0.5% of peripheral blood leukocytes. DC can either be generated from proliferating CD34+ bone marrow precursor cells-which differentiate under a variety of different cytokines including SCF, Flt3, GM-CSF, TGF-β and TNF-α—or from non-proliferating peripheral CD14+ cells (monocytes). Usually, CD34+ precursors mobilised by G-CSF are isolated by leukapheresis to obtain high numbers of peripheral cells for therapeutical purposes. These cells seem to be more efficient in the activation of tumour-specific CTLs than CD14+ derived DC. CD34+ cells expand 10-30-fold. Yields of 5×106 cells per leukapheresis are typically obtained. In contrast, monocytes are abundantly present in peripheral blood and can be easily obtained by peripheral blood drawings or leukapheresis. Protocols for the generation of large amounts of monocyte-derived DC are known since 1994 (see, for example, Romani N, et al., J Exp Med. 1994; 180:83-93, which is herein incorporated by reference) and have been used for both experimental and therapeutical purposes. In some embodiments, leukocytes may be prepared from peripheral blood using density centrifugation techniques. Monocytes can be isolated by an adherence step and subsequently cultured in the presence of one or more factors described herein such as GM-CSF, IL-4 and FCS (fetal calf serum) or alternatively-under serum free conditions. Adherent cells typically show cytoplasmic processes typical for DC. After co-culturing with immunologic effector cells DC form typical cluster.

DC display several antigens on their cell surface, all of which are characteristic, but not specific. The most typical markers at present are HLA-class-I-, -class-II-molecules and co-stimulatory markers (CD80, CD86). Immature DC-obtained after culture with molecules such as GM-CSF and IL-4, can be grown to mature DC by co-culturing with TNF-α, IL-6, IL-1β, and PGE2 or, alternatively, with a so-called monocyte conditioned medium (MCM) for another period of time (maturation phase). In contrast to immature DC, mature DC are much more potent in inducing TH1 and CTL responses in vitro and are resistant to immunosuppressive effects of tumour-derived IL-10. In some embodiments, the DC is a mature or an immature DC.

Vaccination of tumour-patients with a single peptide can result in peptide-specific cytotoxicity. In these cases tumour escape mechanisms may be a problem, for example by the loss of tumour-associated epitopes or of essential antigen presenting molecules. This problem can be circumvented by the usage of polyvalent vaccines in a single patient, i.e. the application of tumour lysates or the application of several peptides.

Tumour-associated peptides do bind with a defined affinity both to the HLA molecules (i.e. HLA class-I and HLA class-II) and the TCR. Whether this peptide is useful for therapeutical purposes or not mainly depends on the degree of its affinity. Low affinity to the HLA molecules is synonymous with low potency in CTL induction, whereas high affinity means high potency in CTL induction. Heteroclitic peptides, that are changed at the HLA-binding motif to achieve a higher affinity between the HLA and the peptide, are potent immunogens. They are able to elicit cross-reactivity with the original peptide, because the TCR-binding motif remains unchanged. As a consequence a tumour-protective immune response against the original peptide can occur after vaccination with the heteroclitic peptide.

Enhancing the immunogenicity of tumour cells may be used as an approach to cancer gene therapy. Cytokine genes have been used in most instances to enhance tumour immunogenicity. DC are attractive targets of gene transfer since DC are easily accessable and since these cells seem to be sensitive to immunologic strategies. For further enhancement of the antigeneic presentation by DC various genes like the genes for interleukin-7, GM-CSF, interleukin-12, interferon-gamma and interferon-alpha have been transfected into DC. Up to 10% transfection efficiencies using electroporation for gene transfer into CD83+ mononuclear cell derived DC were reported. Other non-viral techniques produce robust DC transfection with 17% of monocyte-derived DC using cationic peptide or report the ability of using lipofection in principle.

Higher efficiencies can be achieved using viral vectors. Adenoviral vectors seem to be the most efficient transfection method. Viral vectors such as adenoviral or retroviral vectors can also be used for transduction of CD34+ cell derived DC. Other useful viral vectors include fowlpox virus, lentivirus, avipoxvirus or vaccinia virus.

Cell-based immunotherapy strategies using peptide- or lysate-pulsed DC require interaction between DC and T cells. Physiologically, bone marrow-derived DC or their progenitors migrate to tissues of inflammation, internalise antigens and subsequently reach the paracortex of the lymph nodes and the periarteriolar lymphoid sheath of the spleen (PALS). Here, DC prime naive T cells. Possible routes of administration are intradermal, subcutaneous, intranodal, intravenous and intraperitoneal injection of DC. In some embodiments, the route of administration is intradermal or directly into the lymph node.

B. T-Cell Adoptive Transfer

Adoptive cell transfer in vitro cultivates autologous, extracted T cells for later transfusion. The T cells may be genetically engineered to target the tumor cells, as described herein (e.g. CAR or TCR with CT45 specificity) or may be tumor infiltrating lymphocytes isolated from the tumor and expanded and/or activated in vitro with a CT45 polypeptide. These T cells may be multiplied using molecules such as Interleukin-2, anti-CD3 and allo-reactive feeder cells. These T cells can then transferred back into the patient along with administration of IL-2 to further boost their anti-cancer activity.

Before reinfusion, lymphodepletion of the recipient can be done to eliminate regulatory T cells as well as unmodified, endogenous lymphocytes that compete with the transferred cells for homeostatic cytokines. Lymphodepletion can be achieved, for example, by total body irradiation.

Tumor-infiltrating lymphocytes are a heterogeneous cell population found within neoplastic lesions and are mainly composed of T cells. A fraction of TILs express TCRs directed against unique or shared tumor-associated antigens and exert cytotoxic effects against malignant cells. These TILs can be isolated from resected tumors, selected and expanded ex vivo.

A further approach is to genetically modify the T cells to provide antigen specificity. There are two approaches for redirecting T-cell specificity: (i) gene modification with TCRs directed against tumor-associated antigens and (ii) introduction of a CAR. Different types of antigens can theoretically be used to redirect autologous T cells against tumor cells: tissue-specific differentiation antigens [e.g. CT45 polypeptides]. The term "chimeric antigen receptor"

or "CAR" refers to engineered receptors, which graft an arbitrary specificity onto an immune effector cell.

Genetically modified T cells (TCRs or CARs) can be transfected using virus vectors (retroviruses or lentiviruses) or a transposon system (Sleeping Beauty). Following transfection, genetically modified T cells can be expanded and transferred into patients treated with preconditioning lymphodepletion similar to that used with TIL protocols.

TCR T cells are T cells cloned with TCRs in which variable α- and β-chains with specificity against a tumor antigen (either from a patient or from humanized mice immunized with tumor antigens). Such T cells recognize processed peptide antigens expressed in the context of MHC.

Some of the advantages of TCR T cells arise from the fact that these cells can be produced from peripheral blood T cells (unlike TILs) and can "see" intracellular antigens (unlike CARs).

CARs are used to graft the specificity of a monoclonal antibody onto a T cell. The receptors are called chimeric because they are composed of parts from different sources. The most common form of these molecules are fusions of single-chain variable fragments (scFv) derived from monoclonal antibodies, fused to CD3-zeta transmembrane and endodomain; CD28 or 41BB intracellular domains, or combinations thereof. Such molecules result in the transmission of a signal in response to recognition by the scFv of its target. The variable portions of an immunoglobulin heavy and light chain with specificity to a CT45 antigen can be fused by a flexible linker to form a scFv. This scFv may be preceded by a signal peptide to direct the nascent protein to the endoplasmic reticulum and subsequent surface expression (this is cleaved). A flexible spacer can allow the scFv to orient in different directions to enable antigen binding. The transmembrane domain is a typical hydrophobic alpha helix usually derived from the original molecule of the signalling endodomain which protrudes into the cell and transmits the desired signal. CARs are proteins that allow the T cells to recognize a specific protein (antigen) on tumor cells. These engineered CAR T cells may be expanded in vitro, and the expanded population of CAR T cells can then infused into the patient. After the infusion, the T cells multiply in the patient's body and, with guidance from their engineered receptor, recognize and kill cancer cells that harbor the antigen on their surfaces.

C. Bi-Specific T-Cell Engager

Embodiments of the disclosure relate to bi-specific T-cell engagers (BiTEs). BiTEs are a class of artificial bispecific monoclonal antibodies that direct a host's immune system, more specifically the T cells' cytotoxic activity, against cancer cells. BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to a tumor cell via a tumor specific molecule, such as a CT45 polypeptide described herein. BiTEs form a link between T cells and tumor cells. This causes T cells to exert cytotoxic activity on tumor cells by producing proteins like perforin and granzymes, independently of the presence of MHC I or co-stimulatory molecules. These proteins enter tumor cells and initiate the cell's apoptosis. This action mimics physiological processes observed during T cell attacks against tumor cells.

D. Antibodies

In some embodiments, the disclosure includes antibodies to CT45 polypeptides described herein, such as antibodies with specificity for a CT45 polypeptide having an amino acid sequence of SEQ ID NOS: 1-6 or 29-33. The antibody can be any of the various antibodies described herein, non-limiting, examples of such include a polyclonal antibody, a monoclonal antibody, a chimeric antibody, a human antibody, a veneered antibody, a diabody, a humanized antibody, an antibody derivative, a recombinant humanized antibody, or a derivative or fragment of each thereof.

Antibodies can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, induces the B-lymphocytes to produce immunoglobulins specific for the antigen. Immunoglobulins may be purified from the animal's serum. Common variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a stow release of antigen into draining lymph nodes. Other adjuvants include surfactants that promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods known in the art some of which are described in U.S. Pat. Nos. 7,279,559; 7,119,179; 7,060,800; 6,709,659; 6,656,746; 6,322,788; 5,686,073; and 5,670,153.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8,653, Sp2 SA3, Sp2 MAI, Sp2 SSI, Sp2 SA5, U397, MIA 144, ACT IV, MOLT4, DA-1, JURKAT, WEHI, K-562, COS, RAJI, NIH 313, HL-60, MLA 144, NAMAIWA, NEURO 2A, CHO, PerC.6, YB2/0) or the like, or heteromyelomas, fusion products thereof, or any cell or fusion cell derived there from, or any other suitable cell line as known in the art, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present disclosure. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, cDNA, or the like, display library; e.g., as available from various commercial vendors such as MorphoSys (Martinsreid/Planegg, Del.), BioInvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit, Rev. Biotechnol. 16:95-118; Eren et al. (1998) Mumma 93:154-161 that are capable of producing a repertoire of human antibodies, as known in the art and/or as described herein. Such techniques, include, but are not limited to, ribosome display Wanes et al. (1997) Proc. Natl. Acad. Sci. USA, 94:4937-4942; Hanes et al, (1998) Proc. Natl. Acad. Sci. USA 95:14130-14135); single cell antibody producing technologies (e,g., selected lymphocyte antibody method ("SLAM") (U.S. Pat. No. 5,627,052, Wen et al, (1987) J. Immunol 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass).; Gray et al. (1995) J. Imm. Meth. 182:155-163; and Kenny et al, (1995) Bio. Technol. 13:787-790); B-cell selection (Steenbakkers et al. (1994) Molec. Biol. Reports 19:125-134).

Antibody derivatives of the present disclosure can also be prepared by delivering a polynucleotide encoding an antibody of this disclosure to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873, 316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

The antibodies of the disclosure also include derivatives that are modified by the covalent attachment of any type of molecule to the antibody such that covalent attachment does not prevent the antibody from generating an anti-idiotypic response. Antibody derivatives include, but are not limited to, antibodies that have been modified by glycosylation, acetylation, pegylation, phosphorylation, amidation, derivatization by known protecting/blocking groups, proteolytic cleavage, linkage to a cellular ligand or other protein, etc. Additionally, the derivatives may contain one or more non-classical amino acids.

Antibody derivatives also can be prepared by delivering a polynucleotide of this disclosure to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and references cited therein. Thus, antibodies can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Chimeric, humanized or primatized antibodies of the present disclosure can be prepared based on the sequence of a reference monoclonal antibody prepared using standard molecular biology techniques. DNA encoding the heavy and light chain immunoglobulins can be obtained from the hybridoma of interest and engineered to contain non-reference (e.g., human) immunoglobulin sequences using standard molecular biology techniques. For example, to create a chimeric antibody, the murine variable regions can be linked to human constant regions using methods known in the art (U.S. Pat. No. 4,816,567). To create a humanized antibody, the murine CDR regions can be inserted into a human framework using methods known in the art (U.S. Pat. Nos. 5,225,539 and 5,530,101; 5,585,089; 5,693,762 and 6,180, 370). Similarly, to create a primatized antibody the murine CDR regions can be inserted into a primate framework using methods known in the art (WO 93/02108 and WO 99/55369).

Techniques for making partially to fully human antibodies are known in the art and any such techniques can be used. According to one embodiment, fully human antibody sequences are made in a transgenic mouse that has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59 (6): 1236-1243; Jakobovits (1998) Advanced Drug Reviews 31:33-42; Green and Jakobovits (1998) J. Exp. Med. 188 (3): 483-495; Jakobovits (1998) Exp. Opin. Invest. Drugs 7 (4): 607-614; Tsuda et al.

(1997) Genomics 42:413-421; Sherman-Gold (1997) Genetic Engineering News 17 (14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al, (1995) Genomics 26:294-307; Jakobovits (1994) Current Biology 4 (8): 761-763; Arbones et al. (1994): Immunity 1 (4): 247-260; Jakobovits (1993) Nature 362 (6417): 255-258; Jakobovits et al. (1993) Proc. Natl. Acad. Sci. USA 90 (6): 2551-2555; and U.S. Pat. No. 6,075,181).

The antibodies of this disclosure also can be modified to create chimeric antibodies. Chimeric antibodies are those in which the various domains of the antibodies' heavy and light chains are coded for by DNA from more than one species. See, e.g., U.S. Pat. No. 4,816,567.

The antibodies of this disclosure can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present disclosure include naturally purified products, products of chemical synthetic procedures, and products produced by recombinant techniques from a eukaryotic host, including, for example, yeast, higher plant, insect and mammalian cells, or alternatively from a prokaryotic host as described above. A number of antibody production systems are described in Birch & Radner (2006) Adv. Drug Delivery Rev. 58:671-685.

II. PP4 Complex Inhibitors

Methods of the disclosure relate to therapies and combination therapies comprising PP4 inhibitors. In some embodiments, the PP4 inhibitor comprises all or part of a CT45 polypeptide. An exemplary CT45 polypeptide includes any of SEQ ID NO:7-:

```
CT45A5:
                                          (SEQ ID NO: 7)
MTDKTEKVAVDPETVFKRPRECDSPSYQKRQRMALLARKQGAGDSLIAGS

AMSKEKKLMTGHAIPPSQLDSQIDDFTGFSKDGMMQKPGSNAPVGGNVTS

SFSGDDLECRETASSPKSQREINADIKRKLVKELRCVGQKYEKIFEMLEG

VQGPTAVRKRFFESIIKEAARCMRRDFVKHLKKKLKRMI.

CT45A7:
                                          (SEQ ID NO: 8)
MTDKTEKVAVDPETVFKRPRECDSPSYQKRQRMALLARKQGAGDSLIAGS

AMSKEKKLMTGHAIPPSQLDSQIDDFTGFSKDGMMQKPGSNAPVGGNVTS

SFSGDDLECRETASSPKSQREINADIKRKLVKELRCVGQKYEKIFEMLEG

VQGPTAVRKRFFESIIKEAARCMRRDFVKHLKKKLKRMI.

CT45A6:
                                          (SEQ ID NO: 9)
MTDKTEKVAVDPETVFKRPRECDSPSYQKRQRMALLARKQGAGDSLIAGS

AMSKEKKLMTGHAIPPSQLDSQIDDFTGFSKDGMMQKPGSNAPVGGNVTS

SFSGDDLECRETASSPKSQREINADIKRKLVKELRCVGQKYEKIFEMLEG

VQGPTAVRKRFFESIIKEAARCMRRDFVKHLKKKLKRMI.

CT45A3:
                                          (SEQ ID NO: 10)
MTDKTEKVAVDPETVFKRPRECDSPSYQKRQRMALLARKQGAGDSLIAGS

AMSKEKKLMTGHAIPPSQLDSQIDDFTGFSKDRMMQKPGSNAPVGGNVTS

SFSGDDLECRETASSPKSQREINADIKRKLVKELRCVGQKYEKIFEMLEG

VQGPTAVRKRFFESIIKEAARCMRRDFVKHLKKKLKRMI.

CT45A1:
                                          (SEQ ID NO: 11)
MTDKTEKVAVDPETVFKRPRECDSPSYQKRQRMALLARKQGAGDSLIAGS

AMSKAKKLMTGHAIPPSQLDSQIDDFTGFSKDRMMQKPGSNAPVGGNVTS

SFSGDDLECRETASSPKSQREINADIKRKLVKELRCVGQKYEKIFEMLEG

VQGPTAVRKRFFESIIKEAARCMRRDFVKHLKKKLKRMI.

CT45A4:
                                          (SEQ ID NO: 12)
MTDKTEKVAVDPETVFKRPRECDSPSYQKRQRMALLARKQGAGDSLIAGS

AMSKAKKLMTGHAIPPSQLDSQIDDFTGFSKDRMMQKPGSNAPVGGNVTS

SFSGDDLECRETASSPKSQQEINADIKRKLVKELRCVGQKYEKIFEMLEG

VQGPTAVRKRFFESIIKEAARCMRRDFVKHLKKKLKRMI.

CT45A9:
                                          (SEQ ID NO: 13)
MTDKTEKVAVDPETVFKRPRECDSPSYQKRQRMALLARKQGAGDSLIAGS

AMSKEKKLMTGHAIPPSQLDSQIDDFTGFSKDRMMQKPGSNAPVGGNVTS

SFSGDDLECRETAFSPKSQQEINADIKRQLVKELRCVGQKYEKIFEMLEG

VQGPTAVRKRFFESIIKEAARCMRRDFVKHLKKKLKRMI.

CT45A8:
                                          (SEQ ID NO: 14)
MTDKTEKVAVDPETVFKRPRECDSPSYQKRQRMALLARKQGAGDSLIAGS

AMSKEKKLMTGHAIPPSQLDSQIDDFTGFSKDRMMQKPGSNAPVGGNVTS

SFSGDDLECRETAFSPKSQQEINADIKRQLVKELRCVGQKYEKIFEMLEG

VQGPTAVRKRFFESIIKEAARCMRRDFVKHLKKKLKRMI.

CT45A2:
                                          (SEQ ID NO: 15)
MTDKTEKVAVDPETVFKRPRECDSPSYQKRQRMALLARKQGAGDSLIAGS

AMSKEKKLMTGHAIPPSQLDSQIDDFTGFSKDRMMQKPGSNAPVGGNVTS

SFSGDDLECRETAFSPKSQQEINADIKRQLVKELRCVGQKYEKIFEMLEG

VQGPTAVRKRFFESIIKEAARCMRRDFVKHLKKKLKRMI.

CT45A10:
                                          (SEQ ID NO: 16)
MTDKTEKVAVDPETVFKRPRECDSPSYQKRQRMALLARKQGAGDSLIAGS

AMSKEKKLMTGHAIPPSQLDSQIDDFTGFSKDGMMQKPGSNAPVGGNVTS

SFSGDDLECRGIASSPKSQQEINADIKCQVVKEIRCLGRKYEKIFEMLEG

VQGPTAVRKRFFESIIKEAARCMRRDFVKHLKKKLKRMI

Consensus:
                                          (SEQ ID NO: 17)
MTDKTEKVAVDPETVFKRPRECDSPSYQKRQRMALLARKQGAGDSLTAGS

AMSK(X55)KKLMTGHAIPPSQLDSQIDDFTGFSKD(X83)MMQKPGSNA

PVGGNVTS(X101)FSGDDLECR(X111)(X112)A(X114)SPKSQ
```

-continued (X₁₂₀)EINADIK(X₁₂₈)(X₁₂₉)(X₁₃₀)VKE(X₁₃₄)RC(X₁₃₇)G (X₁₃₉)KYEKIFEMLEGVQGPTAVRKRFFESIIKEAARCMRRDFVKHLKK

KLKRMI.

In some embodiments, the CT45 polypeptide comprises a portion of SEQ ID NO:7-17. In some embodiments, the CT45 polypeptide comprises amino acids 1-120 of SEQ ID NO:7-17. In some embodiments, the CT45 polypeptide comprises a fragment of a polypeptide having an amino acid sequence of any one of SEQ ID NO:7-17. In some embodiments, the CT45 polypeptide (or peptide) comprises a fragment of SEQ ID NO:7-17, wherein the fragment comprises any polypeptide or peptide fragment having at least, at most, or exactly 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, or 189 (or any derivable range therein) contiguous amino acids from any of SEQ ID NOS: 7-17.

In some embodiments, the CT45 polyepeptide comprises amino acids 1-120, 1-110, 1-105, 1-100, 1-90, 1-80, 1-70, or 1-60 of SEQ ID NOS: 7-17. In some embodiments, the CT45 polypeptide comprises amino acids 5-120, 5-110, 5-105, 5-100, 5-90, 5-80, 5-70, or 5-60 of SEQ ID NOS: 7-17. In some embodiments, the CT45 polyepeptide comprises amino acids 10-120, 15-110, 15-105, 15-100, 15-90, 15-80, 15-70, or 15-60 of SEQ ID NOS: 7-17. In some embodiments, the CT45 polyepeptide comprises amino acids 20-120, 25-110, 30-105, 35-100, 40-90, 45-80, 50-70, or 55-60 of SEQ ID NOS: 7-17.

Further exemplary CT45 polypeptides include the following N-terminal fragments:

CT45A5:
(SEQ ID NO: 18)
TDKTEKVAVDPETVFKRPRECDSPSYQKRQRMALLARKQGAGDSLIAGSA

MSKEKKLMTGHAIPPSQLDSQIDDFTGFSKDGMMQKPGSNAPVGGNVTSS

FSGDDLECRETASSPKSQR.

CT45A7:
(SEQ ID NO: 19)
MTDKTEKVAVDPETVFKRPRECDSPSYQKRQRMALLARKQGAGDSLIAGS

AMSKEKKLMTGHAIPPSQLDSQIDDFTGFSKDGMMQKPGSNAPVGGNVTS

SFSGDDLECRETASSPKSQR.

CT45A6:
(SEQ ID NO: 20)
MTDKTEKVAVDPETVFKRPRECDSPSYQKRQRMALLARKQGAGDSLIAGS

AMSKEKKLMTGHAIPPSQLDSQIDDFTGFSKDGMMQKPGSNAPVGGNVTS

SFSGDDLECRETASSPKSQR.

CT45A3:
(SEQ ID NO: 21)
MTDKTEKVAVDPETVFKRPRECDSPSYQKRQRMALLARKQGAGDSLIAGS

AMSKEKKLMTGHAIPPSQLDSQIDDFTGFSKDRMMQKPGSNAPVGGNVTS

SFSGDDLECRETASSPKSQR.

CT45A1:
(SEQ ID NO: 22)
MTDKTEKVAVDPETVFKRPRECDSPSYQKRQRMALLARKQGAGDSLIAGS

AMSKAKKLMTGHAIPPSQLDSQIDDFTGFSKDRMMQKPGSNAPVGGNVTS

SFSGDDLECRETASSPKSQR.

CT45A4:
(SEQ ID NO: 23)
MTDKTEKVAVDPETVFKRPRECDSPSYQKRQRMALLARKQGAGDSLIAGS

AMSKAKKLMTGHAIPPSQLDSQIDDFTGFSKDRMMQKPGSNAPVGGNVTS

SFSGDDLECRETASSPKSQQ.

CT45A9:
(SEQ ID NO: 24)
MTDKTEKVAVDPETVFKRPRECDSPSYQKRQRMALLARKQGAGDSLIAGS

AMSKEKKLMTGHAIPPSQLDSQIDDFTGFSKDRMMQKPGSNAPVGGNVTS

SFSGDDLECRETAFSPKSQQ.

CT45A8:
(SEQ ID NO: 25)
MTDKTEKVAVDPETVFKRPRECDSPSYQKRQRMALLARKQGAGDSLIAGS

AMSKEKKLMTGHAIPPSQLDSQIDDFTGFSKDRMMQKPGSNAPVGGNVTS

SFSGDDLECRETAFSPKSQQ.

CT45A2:
(SEQ ID NO: 26)
MTDKTEKVAVDPETVFKRPRECDSPSYQKRQRMALLARKQGAGDSLIAGS

AMSKEKKLMTGHAIPPSQLDSQIDDFTGFSKDRMMQKPGSNAPVGGNVTS

SFSGDDLECRETAFSPKSQQ.

CT45A10:
(SEQ ID NO: 27)
MTDKTEKVAVDPETVFKRPRECDSPSYQKRQRMALLARKQGAGDSLIAGS

AMSKEKKLMTGHAIPPSQLDSQIDDFTGFSKDGMMQKPGSNAPVGGNVTS

SFSGDDLECRGIASSPKSQQ

Consensus:
(SEQ ID NO: 28)
MTDKTEKVAVDPETVFKRPRECDSPSYQKRQRMALLARKQGAGDSLIAGS

AMSK(X₅₅)KKLMTGHAIPPSQLDSQIDDFTGFSKD(X₈₃)MMQKPGSNAP

VGGNVTS(X₁₀₁)FSGDDLECR(X₁₁₁)(X₁₁₂)A(X₁₁₄)SPKSQ (X₁₂₀).

In some embodiments, the CT45 peptide or polypeptide comprises a peptide or polypeptide having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to any one of SEQ ID NOS: 7-28.

$X_{55}$, $X_{83}$, $X_{101}$, $X_{111}$, $X_{112}$, $X_{114}$, $X_{120}$, $X_{128}$, $X_{129}$, $X_{130}$, $X_{134}$, $X_{137}$, or $X_{139}$ may be any amino acid. In some embodiments, $X_{55}$, $X_{83}$, $X_{101}$, $X_{111}$, $X_{112}$, $X_{114}$, $X_{120}$, $X_{128}$, $X_{129}$, $X_{130}$, $X_{134}$, $X_{137}$, or $X_{139}$ are each independently selected from R, H, K, D, E, S, T, N, Q, C, U, G, P, A, V, I, L, M, F, Y, and W. In some embodiments, $X_{55}$ is selected from E and A. In some embodiments, $X_{83}$ is selected from G and R. In some embodiments, $X_{101}$ is selected from S and N. In some embodiments, Xin is selected from E and G. In some embodiments, $X_{112}$ is selected from T and I. In some embodiments, $X_{114}$ is selected from S and F. In some embodiments, $X_{120}$ is selected from R and Q. In some embodiments, $X_{128}$ is selected from R and C. In some embodiments, $X_{129}$ is selected from K and Q. In some embodiments, $X_{130}$ is selected from L and V. In some embodiments, $X_{134}$ is selected from L and I. In some embodiments, $X_{137}$ is selected from V and L. In some embodiments, $X_{139}$ is selected from Q and R. In some embodiments, the CT45 polypeptide comprises a polypeptide variant of SEQ ID NOS: 7-28, wherein the variant comprises amino acid substitutions at one or more of amino acids 55, 83, 101, 111, 112, 114, 120, 128, 129, 130, 134, 137, and/or 139. In some embodiments, the CT45 polypeptide comprises a polypeptide variant of SEQ ID NOS: 7-28, wherein the variant comprises amino acid substitutions at one or more amino acids at positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and/or 120 of SEQ ID NOS: 7-28. In some embodiments, the CT45 polypeptide comprises a polypeptide variant of SEQ ID NOS: 7-17, wherein the variant comprises amino acid substitutions at one or more amino acid positions 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, or 189 of SEQ ID NOS: 7-17.

In certain aspects the amino acid substitution can be any of the other 20 amino acids. In some embodiments, conservative amino acid substitutions can be specifically excluded from possible amino acid substitutions. In some embodiments, only non-conservative substitutions are included. In some embodiments, non-conservative amino acid substitutions can be specifically excluded from possible amino acid substitutions. In some embodiments, only conservative substitutions are included.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

In some embodiments, the CT45 polypeptide comprises a polypeptide variant of SEQ ID NOS: 7-28, wherein the variant comprises one or more amino acid substitutions of a R, H, K, D, E, S, T, N, Q, C, U, G, P, A, V, I, L, M, F, Y, or W for the amino acid at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and/or 120 of SEQ ID NOS: 7-28. In some embodiments, the CT45 polypeptide comprises a polypeptide variant of SEQ ID NOS: 7-17, wherein the variant comprises one or more amino acid substitutions of a R, H, K, D, E, S, T, N, Q, C, U, G, P, A, V, I, L, M, F, Y, or W for the amino acid at position 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, or 189 of SEQ ID NOS: 7-17.

III. Pharmaceutical Compositions

Embodiments include methods for treating cancer with compositions comprising CT45-targeting agents and additional therapeutic agents. Administration of the compositions will typically be via any common route. This includes, but is not limited to oral, parenteral, orthotopic, intradermal, subcutaneous, intramuscular, intraperitoneal, intranasal, intratumoral, or intravenous injection. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, or about 25% to about 70%. In some embodiments, the compositions are administered orally.

Typically, compositions are administered in a manner compatible with the dosage formulation, and in such amount as will be therapeutically effective and immune modifying. The quantity to be administered depends on the subject to be treated. Precise amounts of active ingredient required to be administered depend on the judgment of the practitioner.

The manner of application may be varied widely. Any of the conventional methods for administration of a pharmaceutical composition are applicable. These are believed to include oral application on a solid physiologically acceptable base or in a physiologically acceptable dispersion, parenterally, by injection and the like. The dosage of the pharmaceutical composition will depend on the route of administration and will vary according to the size and health of the subject.

In many instances, it will be desirable to have multiple administrations of at most about or at least about 3, 4, 5, 6, 7, 8, 9, 10 or more. The administrations may range from 2 day to twelve week intervals, more usually from one to two week intervals. The course of the administrations may be followed by assays for CT45 activity.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The compositions can be formulated for parenteral administration, e.g., formulated for injection via the intravenous, intradermal, intramuscular, sub-cutaneous, or even intraperitoneal routes. In some embodiments, the composition is administered by intravenous injection. The preparation of an aqueous composition that contains an active ingredient will be known to those of skill in the art in light of the current disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredients in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

Upon formulation, solutions will be administered in a manner compatible with the dosage formulation and in such amount as is therapeutically or prophylactically effective. The formulations are easily administered in a variety of dosage forms, such as the type of injectable solutions described above.

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of a condition. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of the condition (or any range derivable therein). The patient may be treated for 1, 2, 3, 4, 5, 6, 7, 8, 9, 10 or more days (or any range derivable therein) or until symptoms of an the condition have disappeared or been reduced or after 6, 12, 18, or 24 hours or 1, 2, 3, 4, or 5 days after symptoms of an infection have disappeared or been reduced.

IV. Combination Therapy

The compositions and related methods, particularly administration of one or more CT45-targeted immunotherapies may also be used in combination with the administration of conventional cancer therapies, such as those known in the art and/or described below.

Conventional cancer therapies include one or more selected from the group of chemotherapies, checkpoint inhibitor, a MUC-1 inhibitor, a CD40 activator, an IDO inhibitor, and an OX86 agonists, chemical or radiation based treatments, and surgery. Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, or any analog or derivative variant of the foregoing.

Suitable therapeutic agents include, for example, vinca alkaloids, agents that disrupt microtubule formation (such as colchicines and its derivatives), anti-angiogenic agents, therapeutic antibodies, tyrosine kinase targeting agent (such as tyrosine kinase inhibitors), serine kinase targeting agents, transitional metal complexes, proteasome inhibitors, anti-metabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

In some embodiments, the chemotherapeutic is capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, and/or vinorelbine.

In some embodiments, the chemotherapeutic agent is any of (and in some embodiments selected from the group consisting of adriamycin, colchicine, cyclophosphamide, actinomycin, bleomycin, daunorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof, and the like), topetecan, vinblastine, vincristine, tamoxifen, piposulfan, nab-5404, nab-5800, nab-5801, Irinotecan, HKP, Ortataxel, gemcitabine, Herceptin®, vinorelbine, Doxil®, capecitabine, Gleevec®, Alimta®, Avastin®, Velcade®, Tarceva®, Neulasta®, Lapatinib, STI-571, ZD1839, Iressa® (gefitinib), SH268, genistein, CEP2563, SU6668, SU11248, EMD121974, and Sorafenib.

Non-limiting examples of immune checkpoint inhibitors include fully human monoclonal antibodies, such as RG7446, BMS-936558/MDX-1106, BMS-936559 (anti-PDL1 antibody), Yervoy/ipilimumab (anti-CTLA-4 checkpoint inhibitor), and Tremelimumab (CTLA-4 blocking antibody); humanized antibodies, such as pidilizumab (CT-011, CureTech Ltd.) and lambrolizumab (MK-3475, Merck, PD-1 blocker); and fusion proteins, such as AMP-224 (Merck). Other examples of checkpoint inhibitors include anti-OX40, PD-L1 monoclonal Antibody (Anti-B7-H1; MEDI4736), Nivolumab (BMS-936558, Bristol-Myers Squibb, anti-PD1 antibody), CT-011 (anti-PD1 antibody), BY55 monoclonal antibody, MPLDL3280A (anti-PDL1 antibody), and MSB0010718C (anti-PDL1 antibody), MDX-1105 (Medarex), MPDL3280A (Genentech), Anti-KIR antibodies such as lirlumab (Innate Pharma) and IPH2101 (Innate Pharma) may perform similar functions in NK cells. Further examples of checkpoint inhibitors include agonistic anti-4-1bb antibody; agonistic anti-CD27 antibody; agonistic anti-GTIR antibody; agonistic anti-OX40 antibody; and antagonistic anti-TIM3 antibody.

In some embodiments, the additional agent is an immunostimulator. The term "immunostimulator" as used herein refers to a compound that can stimulate an immune response in a subject, and may include an adjuvant. In some embodiments, an immunostimulator is an agent that does not constitute a specific antigen, but can boost the strength and longevity of an immune response to an antigen. Such immunostimulators may include, but are not limited to stimulators of pattern recognition receptors, such as Toll-like receptors, RIG-1 and NOD-like receptors (NLR), mineral salts, such as alum, alum combined with monphosphoryl lipid (MPL) A of Enterobacteria, such as Escherihia coli, Salmonella minnesota, Salmonella typhimurium, or Shigella flexneri or specifically with MPL® (ASO4), MPL A of above-mentioned bacteria separately, saponins, such as QS-21, Quil-A, ISCOMs, ISCOMATRIX, emulsions such as MF59, Montanide, ISA 51 and ISA 720, AS02 (QS21+ squalene+MPL.), liposomes and liposomal formulations such as AS01, synthesized or specifically prepared microparticles and microcarriers such as bacteria-derived outer membrane vesicles (OMV) of N. gonorrheae, *Chlamydia trachomatis* and others, or chitosan particles, depot-forming agents, such as Pluronic block co-polymers, specifically modified or prepared peptides, such as muramyl dipeptide, aminoalkyl glucosaminide 4-phosphates, such as RC529, or proteins, such as bacterial toxoids or toxin fragments.

In some embodiments, the additional agent comprises an agonist for pattern recognition receptors (PRR), including, but not limited to Toll-Like Receptors (TLRs), specifically TLRs 2, 3, 4, 5, 7, 8, 9 and/or combinations thereof. In some embodiments, additional agents comprise agonists for Toll-Like Receptors 3, agonists for Toll-Like Receptors 7 and 8, or agonists for Toll-Like Receptor 9; preferably the recited immunostimulators comprise imidazoquinolines; such as R848; adenine derivatives, such as those disclosed in U.S. Pat. No. 6,329,381, U.S. Published Patent Application 2010/0075995, or WO 2010/018132; immunostimulatory DNA; or immunostimulatory RNA. In some embodiments, the additional agents also may comprise immunostimulatory RNA molecules, such as but not limited to dsRNA, poly I:C or poly I:poly C12U (available as Ampligen®, both poly I:C and poly I:polyC12U being known as TLR3 stimulants), and/or those disclosed in F. Heil et al., "Species-Specific Recognition of Single-Stranded RNA via Toll-like Receptor 7 and 8" Science 303 (5663), 1526-1529 (2004); J. Vollmer et al., "Immune modulation by chemically modified ribonucleosides and oligoribonucleotides" WO 2008033432 A2; A. Forsbach et al., "Immunostimulatory oligoribonucleotides containing specific sequence motif(s) and targeting the Toll-like receptor 8 pathway" WO 2007062107 A2; E. Uhlmann et al., "Modified oligoribonucleotide analogs with enhanced immunostimulatory activity" U.S. Pat. Appl. Publ. US 2006241076; G. Lipford et al., "Immunostimulatory viral RNA oligonucleotides and use for treating cancer and infections" WO 2005097993 A2; G. Lipford et al., "Immunostimulatory G,U-containing oligoribonucleotides, compositions, and screening methods" WO 2003086280 A2. In some embodiments, an additional agent may be a TLR-4 agonist, such as bacterial lipopolysaccharide (LPS), VSV-G, and/or HMGB-1. In some embodiments, additional agents may comprise TLR-5 agonists, such as flagellin, or portions or derivatives thereof, including but not limited to those disclosed in U.S. Pat. Nos. 6,130,082, 6,585,980, and 7,192,725.

In some embodiments, additional agents may be proinflammatory stimuli released from necrotic cells (e.g., urate crystals). In some embodiments, additional agents may be activated components of the complement cascade (e.g., CD21, CD35, etc.). In some embodiments, additional agents may be activated components of immune complexes. Additional agents also include complement receptor agonists, such as a molecule that binds to CD21 or CD35. In some embodiments, the complement receptor agonist induces endogenous complement opsonization of the synthetic nanocarrier. In some embodiments, immunostimulators are cytokines, which are small proteins or biological factors (in the range of 5 kD-20 kD) that are released by cells and have specific effects on cell-cell interaction, communication and behavior of other cells. In some embodiments, the cytokine receptor agonist is a small molecule, antibody, fusion protein, or aptamer.

In some embodiments, the additional agent is an antibody-drug conjugate. In some embodiments, the antibody-drug conjugate is selected from gemtuzumab ozogamicin, brentuximab vedotin, and trastuzumab emtansine.

In some embodiments, the additional agent is a chimeric antigen receptor (CAR). CARs are artificial T cell receptors which graft a specificity onto an immune effector cell. The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g. neuroblastoma cells). The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows the scFv to orient in different directions to enable antigen binding. The transmembrane domain is a typical hydrophobic alpha helix usually derived from the original molecule of the signalling endodomain which protrudes into the cell and transmits the desired signal.

Suitable doses for cancer therapeutics in patients include, for example, about 1 mg/kg/day to about 5 mg/kg/day, intravenous doses include, for example, initially about 40 mg/kg to about 50 mg/kg in divided doses over a period of about 2 days to about 5 days or about 10 mg/kg to about 15 mg/kg about every 7 days to about 10 days or about 3 mg/kg to about 5 mg/kg twice a week or about 1.5 mg/kg/day to about 3 mg/kg/day. Because of adverse gastrointestinal effects, the intravenous route is used in some embodiments. The drug also sometimes is administered intramuscularly, by infiltration or into body cavities.

Typically, for a human adult (weighing approximately 70 kilograms), from about 0.1 mg to about 3000 mg (including all values and ranges there between), or from about 5 mg to about 1000 mg (including all values and ranges there between), or from about 10 mg to about 100 mg (including all values and ranges there between), of a compound are administered. It is understood that these dosage ranges are by way of example only, and that administration can be adjusted depending on the factors known to the skilled artisan.

In certain embodiments, a subject is administered about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or µg/kg or micrograms/kg/minute or mg/kg/min or micrograms/kg/hour or mg/kg/hour, or any range derivable therein.

The amount of the chemotherapeutic agent delivered to the patient may be variable. In one suitable embodiment, the chemotherapeutic agent may be administered in an amount effective to cause arrest or regression of the cancer in a host, when the chemotherapy is administered with the construct. In other embodiments, the chemotherapeutic agent may be administered in an amount that is anywhere between 2 to 10,000 fold less than the chemotherapeutic effective dose of the chemotherapeutic agent. For example, the chemotherapeutic agent may be administered in an amount that is about 20 fold less, about 500 fold less or even about 5000 fold less than the chemotherapeutic effective dose of the chemotherapeutic agent. The chemotherapeutics of the disclosure can be tested in vivo for the desired therapeutic activity in combination with the construct, as well as for determination of effective dosages. For example, such compounds can be tested in suitable animal model systems prior to testing in humans, including, but not limited to, rats, mice, chicken, cows, monkeys, rabbits, etc. In vitro testing may also be used to determine suitable combinations and dosages, as described in the examples.

Actual dosage levels of the active ingredients in the methods of this disclosure may be varied so as to obtain an amount of the active ingredient which is effective to achieve the desired therapeutic response for a particular patient, composition and mode of administration, without being toxic to the patient. The selected dosage level will depend upon a variety of factors, including the activity of the chemotherapeutic agent selected, the route of administration, the time of administration, the rate of excretion of the chemotherapeutic agent, the duration of the treatment, other drugs, compounds and/or materials used in combination with the particular chemotherapeutic agent, the age, sex, weight, condition, general health and prior medical history of the patient being treated, and like factors well known in the medical arts.

Administration of pharmaceutical compositions to a patient/subject will follow general protocols for the administration of such compounds, taking into account the toxicity, if any. It is expected that the treatment cycles would be repeated as necessary.

Various combinations with the CT45-targeted immunotherapy and a traditional therapy may be employed, for example, a CT45-targeted immunotherapy is "A" and the traditional therapy (or a combination of such therapies) given as part of a treatment for pancreatitis, is "B":

```
A/B/A  B/A/B  B/B/A  A/A/B  A/B/B  B/A/A  A/B/B/B  B/A/B/B
B/B/B/A  B/B/A/B  A/A/B/B  A/B/A/B  A/B/B/A  B/B/A/A
B/A/B/A  B/A/A/B  A/A/A/B  B/A/A/A  A/B/A/A  A/A/B/A
```

Administration of pharmaceutical compositions to a patient/subject will follow general protocols for the administration of such compounds, taking into account the toxicity, if any. It is expected that the treatment cycles would be repeated as necessary.

V. Samples

In certain aspects, methods involve obtaining a sample from a subject. The methods of obtaining provided herein may include methods of biopsy such as fine needle aspiration, core needle biopsy, vacuum assisted biopsy, incisional biopsy, excisional biopsy, punch biopsy, shave biopsy or skin biopsy. In certain embodiments the sample is obtained from a biopsy from cancer tissue by any of the biopsy methods previously mentioned. In other embodiments the sample may be obtained from any of the tissues provided herein that include but are not limited to cells of the ovaries, abdominal fluid, abnormal tissue inside the ovaries and/or reproductive system, follicular cells, epithelial cells, granulosa cells, and gametes. Alternatively, the sample may be obtained from any other source including but not limited to blood, sweat, hair follicle, buccal tissue, tears, menses, feces, or saliva. In certain aspects the sample is obtained from cystic fluid or fluid derived from a tumor or neoplasm. In yet other embodiments the cyst, tumor or neoplasm is breast cells. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, scraping, phlebotomy, or any other methods known in the art. In some cases, the sample may be obtained, stored, or transported using components of a kit of the present methods. In some cases, multiple samples, such as multiple cancer samples may be obtained for diagnosis by the methods described herein. In other cases, multiple samples, such as one or more samples from one tissue type and one or more samples from another tissue (for example buccal) may be obtained for diagnosis by the methods. In some cases, multiple samples such as one or more samples from one tissue type (e.g., breast) and one or more samples from another tissue (e.g., blood) may be obtained at the same or different times. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods. In one embodiment, the sample is a fine needle aspirate of a tumor or a suspected tumor or neoplasm. In some cases, the fine needle aspirate sampling procedure may be guided by the use of an ultrasound, X-ray, or other imaging device.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, genes, gene fragments, expression products, gene expression products, or gene expression product fragments of an individual to be tested. Methods for determining sample suitability and/or adequacy are provided.

In some embodiments, the subject may be referred to a specialist such as an oncologist, surgeon, or endocrinologist. The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

VI. Nucleic Acid Assays

Aspects of the methods include assaying nucleic acids to determine expression levels. Arrays can be used to detect differences between two samples. Specifically contemplated applications include identifying and/or quantifying differences between CT45 from a sample that is normal and from a sample that is not normal, between a cancerous condition and a non-cancerous condition, or between two differently treated samples. Also, CT45 expression levels may be compared between the expression level of the test sample and a reference level indicating favorable prognosis or poor prognosis.

A sample that is not normal is one exhibiting phenotypic trait(s) of a disease or condition or one believed to be not normal with respect to that disease or condition. It may be compared to a cell that is normal with respect to that disease or condition. Phenotypic traits include symptoms of, or susceptibility to, a disease or condition of which a component is or may or may not be genetic or caused by a hyperproliferative or neoplastic cell or cells or include traits of poor prognosis after certain treatment.

An array comprises a solid support with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424, 186 and Fodor et al., 1991), each of which is incorporated by reference in its entirety for all purposes. Techniques for the synthesis of these arrays using mechanical synthesis methods are described in, e.g., U.S. Pat. No. 5,384,261, incorporated herein by reference in its entirety for all purposes. Although a planar array surface is used in certain aspects, the array may be fabricated on a surface of virtually any shape or even a multiplicity of surfaces. Arrays may be nucleic acids on beads, gels, polymeric surfaces, fibers such as fiber optics, glass or any other appropriate substrate, see U.S. Pat. Nos. 5,770,358, 5,789, 162, 5,708,153, 6,040,193 and 5,800,992, which are hereby incorporated in their entirety for all purposes.

In addition to the use of arrays and microarrays, it is contemplated that a number of difference assays could be employed to analyze CT45, their activities, and their effects. Such assays include, but are not limited to, nucleic amplification, polymerase chain reaction, quantitative PCR, RT-PCR, in situ hybridization, digital PCR, dd PCR (digital droplet PCR), nCounter (nanoString), BEAMing (Beads, Emulsions, Amplifications, and Magnetics) (Inostics), ARMS (Amplification Refractory Mutation Systems), RNA-Seq, TAm-Seq (Tagged-Amplicon deep sequencing), PAP (Pyrophosphorolysis-activation polymerization), next generation RNA sequencing, northern hybridization, hybridization protection assay (HPA) (GenProbe), branched DNA (bDNA) assay (Chiron), rolling circle amplification (RCA), single molecule hybridization detection (US Genomics), Invader assay (ThirdWave Technologies), and/or Bridge Litigation Assay (Genaco).

VII. Protein Expression Assays

In some embodiments, the gene or protein expression of CT45 or specific antigens is compared to a control or a reference level. Such methods, like the methods of detecting expression described herein, are useful in providing risk prediction, diagnosis, prognosis, etc., of a disease or cancer.

Methods for measuring transcription and/or translation of a particular gene sequence or biomarker are well known in the art. See, for example, Ausubel, Current Protocols in Molecular Biology, 1987-2006, John Wiley & Sons; and Sambrook and Russell, Molecular Cloning: A Laboratory Manual, 3rd Edition, 2000.

Polypeptides encoded by the CT45 gene described herein can be detected and/or quantified by any methods known to those of skill in the art from samples as described herein. In some embodiments, antibodies can also be used to detect polypeptides encoded by the genes described herein. Antibodies to these polypeptides can be produced using well known techniques (see, e.g., Harlow & Lane, 1988 and Harlow & Lane, 1999; Coligan, 1991; Goding, 1986; and Kohler & Milstein, 1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., 1989; Ward et al., 1989).

Once specific antibodies are available, CT45 expression can be detected by a variety of immunoassay methods. For a review of immunological and immunoassay procedures, see Basic and Clinical Immunology (1991). Moreover, the immunoassays of certain aspects can be performed in any of several configurations, which are reviewed extensively in Enzyme Immunoassay (1980); and Harlow & Lane, supra). In some embodiments, the methods, kits, or compositions comprise an antibody that specifically recognizes a CT45 antigen corresponding to one or more of SEQ ID NOS: 1-6 or 29-33.

Immunoassays also often use a labeling agent to specifically bind to and label the complex formed by the antibody and antigen. The labeling agent may itself be one of the moieties comprising the antibody/antigen complex. Thus, the labeling agent may be a labeled polypeptide or a labeled antibody that binds the protein of interest. Alternatively, the labeling agent may be a third moiety, such as a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the labeling agent. These proteins exhibit a strong non-immunogenic reactivity with immunoglobulin constant regions from a variety of species (see, e.g., Kronval et al., 1973; Akerstrom et al., 1985). The labeling agent can be modified with a detectable moiety, such as biotin, to which another molecule can specifically bind, such as streptavidin. A variety of detectable moieties are well known to those skilled in the art.

Commonly used assays include noncompetitive assays, e.g., sandwich assays, and competitive assays. In competitive assays, the amount of polypeptide present in the sample is measured indirectly by measuring the amount of a known, added (exogenous) polypeptide of interest displaced (competed away) from an antibody that binds by the unknown polypeptide present in a sample. Commonly used assay formats include immunoblots, which are used to detect and quantify the presence of protein in a sample. Other assay formats include liposome immunoassays (LIA), which use liposomes designed to bind specific molecules (e.g., antibodies) and release encapsulated reagents or markers. The released chemicals are then detected according to standard techniques (see Monroe et al., 1986).

Any suitable method can be used to detect one or more of the markers described herein. Successful practice can be achieved with one or a combination of methods that can detect and, preferably, quantify the markers. These methods include, without limitation, hybridization-based methods, including those employed in biochip arrays, mass spectrometry (e.g., laser desorption/ionization mass spectrometry), fluorescence (e.g., sandwich immunoassay), surface plasmon resonance, ellipsometry and atomic force microscopy. Expression levels of markers (e.g., polynucleotides or polypeptides) are compared by procedures well known in the art, such as RT-PCR, Northern blotting, Western blotting, flow cytometry, immunocytochemistry, binding to magnetic and/or antibody-coated beads, in situ hybridization, fluorescence in situ hybridization (FISH), flow chamber adhesion assay, ELISA, microarray analysis, or colorimetric assays. Methods may further include, one or more of electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)11, atmospheric pressure photoionization mass spectrometry (APPI-MS), APPI-MS/MS, and APPI-(MS)n, quadrupole mass spectrometry, fourier transform mass spectrometry (FTMS), and ion trap mass spectrometry, where n is an integer greater than zero.

Detection methods may include the use of a biochip array. Biochip arrays include protein and polynucleotide arrays. The protein of interest may be captured on the biochip array and subjected to analysis to detect the level of the protein in a sample.

VIII. ROC Analysis

In statistics, a receiver operating characteristic (ROC), or ROC curve, is a graphical plot that illustrates the performance of a binary classifier system as its discrimination threshold is varied. The curve is created by plotting the true positive rate against the false positive rate at various threshold settings. (The true-positive rate is also known as sensitivity in biomedical informatics, or recall in machine learning. The false-positive rate is also known as the fall-out and can be calculated as 1-specificity). The ROC curve is thus the sensitivity as a function of fall-out. In general, if the probability distributions for both detection and false alarm are known, the ROC curve can be generated by plotting the cumulative distribution function (area under the probability distribution from −infinity to +infinity) of the detection probability in the y-axis versus the cumulative distribution function of the false-alarm probability in x-axis.

ROC analysis provides tools to select possibly optimal models and to discard suboptimal ones independently from (and prior to specifying) the cost context or the class distribution. ROC analysis is related in a direct and natural way to cost/benefit analysis of diagnostic decision making.

The ROC curve was first developed by electrical engineers and radar engineers during World War II for detecting enemy objects in battlefields and was soon introduced to psychology to account for perceptual detection of stimuli. ROC analysis since then has been used in medicine, radiology, biometrics, and other areas for many decades and is increasingly used in machine learning and data mining research.

The ROC is also known as a relative operating characteristic curve, because it is a comparison of two operating characteristics (TPR and FPR) as the criterion changes. ROC analysis curves are known in the art and described in Metz C E (1978) Basic principles of ROC analysis. Seminars in Nuclear Medicine 8:283-298; Youden W J (1950) An index for rating diagnostic tests. Cancer 3:32-35; Zweig M H, Campbell G (1993) Receiver-operating characteristic (ROC) plots: a fundamental evaluation tool in clinical medicine. Clinical Chemistry 39:561-577; and Greiner M, Pfeiffer D, Smith R D (2000) Principles and practical application of the receiver-operating characteristic analysis for diagnostic tests. Preventive Veterinary Medicine 45:23-41, which are herein incorporated by reference in their entirety.

IX. Kits

Certain aspects concern kits containing compositions described herein or compositions to implement methods described herein.

In various aspects, a kit is envisioned containing therapeutic agents and/or other therapeutic and delivery agents. In some embodiments, a kit for preparing and/or administering a therapy described herein may be provided. The kit may comprise one or more sealed vials containing any of the pharmaceutical compositions, therapeutic agents and/or other therapeutic and delivery agents. In some embodiments, the lipid is in one vial, and the therapeutic agent is in a separate vial. The kit may include, for example, at least one agent for the detection of CT45 expression, one or more lipid component, as well as reagents to prepare, formulate, and/or administer the components described herein or perform one or more steps of the methods. In some embodiments, the kit may also comprise a suitable container means, which is a container that will not react with components of the kit, such as an eppendorf tube, an assay plate, a syringe, a bottle, or a tube. The container may be made from sterilizable materials such as plastic or glass. The kits may also comprise reagents to isolate, purify, and/or fractionate biological samples from a patient. The kit may also comprise growth stimulating or immune stimulating factors described herein, reagents for culturing cells in vitro, and reagents for freezing, splitting, and/or propagating cells in vitro. The kit may also comprise vectors expressing nucleic acid constructs such as CT45-specific TCR genes and/or CT45-specific chimeric antigen receptors as well as reagents for transferring such nucleic acids into cells.

The kit may further include an instruction sheet that outlines the procedural steps of the methods set forth herein, and will follow substantially the same procedures as described herein or are known to those of ordinary skill. The instruction information may be in a computer readable media containing machine-readable instructions that, when executed using a computer, cause the display of a real or virtual procedure of delivering a pharmaceutically effective amount of a therapeutic agent.

In some embodiments, kits may be provided to evaluate the expression of CT45 or related molecules. Such kits can be prepared from readily available materials and reagents. For example, such kits can comprise any one or more of the following materials: enzymes, reaction tubes, buffers, detergent, primers and probes, nucleic acid amplification, and/or hybridization agents. In a particular embodiment, these kits allow a practitioner to obtain samples in blood, tears, semen, saliva, urine, tissue, serum, stool, colon, rectum, sputum, cerebrospinal fluid and supernatant from cell lysate. In another embodiment, these kits include the needed apparatus for performing RNA extraction, RT-PCR, and gel electrophoresis. Instructions for performing the assays can also be included in the kits.

Kits may comprise components, which may be individually packaged or placed in a container, such as a tube, bottle, vial, syringe, or other suitable container means. The components may include probes, primers, antibodies, arrays, negative and/or positive controls. Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

The kit can further comprise reagents for labeling CT45 in the sample. The kit may also include labeling reagents, including at least one of amine-modified nucleotide, poly(A) polymerase, and poly(A) polymerase buffer. Labeling reagents can include an amine-reactive dye or any dye known in the art.

The components of the kits may be packaged either in aqueous media or in lyophilized form. The container means of the kits will generally include at least one vial, test tube, flask, bottle, syringe or other container means, into which a component may be placed, and preferably, suitably aliquotted. Where there is more than one component in the kit (labeling reagent and label may be packaged together), the kit also will generally contain a second, third or other additional container into which the additional components may be separately placed. However, various combinations of components may be comprised in a vial. The kits may also include a means for containing the nucleic acids, antibodies or any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred.

Alternatively, the components of the kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried power. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 µg or at least or at most those amounts of dried dye are provided in kits in certain aspects. The dye may then be resuspended in any suitable solvent, such as DMSO.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits may include a means for containing the vials in close confinement for commercial sale, such as, e.g., injection and/or blow-molded plastic containers into which the desired vials are retained.

A kit may also include instructions for employing the kit components as well the use of any other reagent not included in the kit. Instructions may include variations that can be implemented.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of particular embodiments, are exemplary, and are not intended as limitations on the scope of the invention. Changes therein and other uses which are encompassed within the spirit of the invention as defined by the scope of the claims will occur to those skilled in the art.

The following examples further describe embodiments of the disclosure and may contain duplicative data and information that is not necessarily an indication of experiments that have been repeated.

Example 1: Proteomics Identifies CT45 as a Mediator of Chemosensitivity and Immunotherapy Target in Ovarian Cancer A. Proteomics Identifies CT45

In this study, the inventors performed quantitative proteomics on chemosensitive and chemoresistant formalin-fixed and paraffin-embedded (FFPE) tumour samples isolated from 25 chemotherapy-naïve patients with advanced stage HGSOC (FIG. 1a, Table 1). Since patients with advanced stage, metastatic disease often have the worst prognosis, metastatic tumour from the omentum was used for this analysis. Global proteomic differences between chemoresistant (N=11, median DFS=190 days) and chemosensitive (N=14, median DFS=1160 days) patients were first assessed in the cohort by using a recently developed label-free proteome quantification approach (4) capable of quantifying large portions of the cellular proteome in a reasonably short time of 4 hours. Out of the 8,190 quantitatively compared proteins (FIG. 1b), the cancer/testis antigen, CT45, was identified as significantly higher expressed in chemosensitive patients in comparison to the resistant group (FDR<5%, FIG. 1c). The CT45 gene family is comprised of 10 separate but highly similar genes with >98% conservation at the protein level (FIG. 4). Due to the high similarity between proteins, the inventors were unable to distinguish which unique paralog was expressed despite achieving >66% protein sequence coverage in the proteomics data. It was further found that protein expression of CT45 highly correlated with disease-free survival (FIG. 1d). Immunohistochemical analysis using an experimentally validated antibody confirmed the relative expression of CT45 in serial sections of the tumours used in the proteomic cohort. Expression was localized to the nucleus and in some cases could be seen in the nucleolus. With few exceptions, expression was largely homogenous across the tumour sections with only slight variations in staining intensity.

TABLE 1

Patient characteristics of proteomic cohort

| | Chemotherapy Status | | | | | |
|---|---|---|---|---|---|---|
| | Resistant | | Sensitive | | | All |
| | No. | % | No. | % | P value | cases |
| Stage | | | | | 1.00 | |
| 3 | 8 | 72.7 | 10 | 71.4 | | 18 |
| 4 | 3 | 27.3 | 4 | 28.6 | | 7 |
| Primary Site | | | | | 0.0850 | |
| Fallopian Tube | 4 | 36.4 | 6 | 42.8 | | 10 |
| Ovary | 7 | 63.6 | 4 | 28.6 | | 11 |
| Peritoneum | 0 | 0 | 4 | 28.6 | | 4 |

TABLE 1-continued

Patient characteristics of proteomic cohort

|  | Chemotherapy Status | | | | | |
| --- | --- | --- | --- | --- | --- | --- |
|  | Resistant | | Sensitive | | | All |
|  | No. | % | No. | % | P value | cases |
| Residual Disease |  |  |  |  | 0.0531 |  |
| Larger than 1 cm | 8 | 72.7 | 5 | 35.7 |  | 13 |
| Smaller than 1 cm | 2 | 18.2 | 9 | 64.3 |  | 11 |
| Unknown | 1 | 9.1 | 0 | 0 |  | 1 |
| Grade |  |  |  |  | 0.4867 |  |
| 2 | 0 | 0 | 2 | 14.3 |  | 2 |
| 3 | 11 | 100 | 12 | 85.7 |  | 23 |
| Chemo Type |  |  |  |  |  |  |
| Adjuvant/1st line | 11 | 100 | 14 | 100 |  |  |
| Chemo Class |  |  |  |  | 1.00 |  |
| Platinum only | 0 | 0 | 1 | 7.1 |  | 1 |
| Taxane/Platinum | 11 | 100 | 13 | 92.9 |  | 24 |
| Progression free survival |  |  |  |  |  |  |
| Median days (range) | 190 (113-391) | | 1160.5 (552-3229) | | <0.0001 |  |
| Overall survival |  |  |  |  |  |  |
| Median days (range) | 448 (228-1489) | | 1550.5 (967-3229) | | <0.0001 |  |
| Age |  |  |  |  |  |  |
| Mean age (range) | 60.0 (47-78) | | 67.1 (51-86) | | 0.0908 |  |

B. Independent Prognostic Indicator

To validate the proteomic findings in a larger patient cohort tissue microarrays (TMA) were stained to analyze CT45 expression in over 200 cases of primary and metastatic ovarian cancer (Table 2). CT45 protein expression was quantified by a Gynecologic Pathologist who was blinded to the patient's outcomes. Of note, CT45 expression was not as common in other ovarian cancer subtypes compared to serous papillary. Furthermore, there was no significant difference in expression between primary and metastatic tumours from the same HGSOC patients (P=0.61). However, consistent with the discovery cohort of 25 patients, CT45 expression highly correlated with chemosensitivity in 124 patients with advanced stage disease (FIGO IIIb or higher) (Table 2). Kaplan-Meier survival analysis revealed that advanced stage (FIGO IIIb or higher) HGSOC patients with high CT45 expression and had a lower risk of recurrence with median days to platinum resistance of 363 days (staining 1+) versus 153.5 days for patients with no expression of CT45 (FIG. 1e). A trend towards longer overall survival was evident although this did not reach significance (FIG. 1f). Additionally, the inventors further validated the proteomic findings using a much larger and independent public dataset generated by The Cancer Genome Atlas (TCGA) consortium (6). Using RNA-Seq data of 305 HGSOC cases, CT45 expression was calculated by the accumulated expression of the detected 6 gene family members (CT45A1-A6). Grouping patients into a CT45 high group (top 25%, N=76) and CT45 low group (lower 75%, N=229) resulted in a significantly longer overall survival for the CT45 high group (FIG. 1g). These results demonstrate that CT45 expression is an independent prognostic indicator in advanced stage HGSOC.

TABLE 2

Patient characteristics of tissue microarray validation cohort. Clinical parameters for patients with advanced stage serous papillary ovarian cancer included in the TMA. validation cohort. Tumors were stained for CT45 and the staining was scored 0-3.

|  | CT45 Status | | | | |
| --- | --- | --- | --- | --- | --- |
|  | 0 (N = 82) | | 1+ (N = 42) | | |
|  | No. | % | No. | % | P value |
| Stage |  |  |  |  | 0.72 |
| 3 | 56 | 68.29 | 30 | 71.43 |  |
| 4 | 26 | 31.71 | 12 | 28.57 |  |
| Primary Site |  |  |  |  | 0.41 |
| Fallopian Tube | 10 | 12.2 | 9 | 21.43 |  |
| Ovary | 62 | 75.61 | 29 | 69.05 |  |
| Peritoneum | 10 | 12.2 | 4 | 9.52 |  |
| Residual Disease |  |  |  |  | 0.10 |
| Larger than 1 cm | 47 | 57.32 | 17 | 40.48 |  |
| Smaller than 1 cm | 34 | 41.46 | 25 | 59.52 |  |
| Unknown | 1 | 1.22 | 0 | 0 |  |
| Grade |  |  |  |  | 0.59 |
| 1 | 1 | 1.22 | 0 | 0 |  |
| 2 | 22 | 26.83 | 8 | 19.05 |  |
| 3 | 59 | 71.95 | 34 | 80.95 |  |
| Chemo Type |  |  |  |  | 0.67 |
| Adjuvant/1st line | 64 | 78.05 | 35 | 83.33 |  |
| Neoadjuvant | 13 | 15.85 | 4 | 9.52 |  |
| None | 5 | 6.1 | 3 | 7.14 |  |
| Chemo Class |  |  |  |  | 0.19 |
| Other | 4 | 4.88 | 6 | 14.29 |  |
| Taxane/Platinunn | 73 | 89.02 | 33 | 78.57 |  |
| None | 5 | 6.1 | 3 | 7.14 |  |
| Chemoresistance |  |  |  |  | 0.005 |
| resistant | 46 | 56.1 | 10 | 23.81 |  |
| intermediate | 11 | 13.41 | 9 | 21.43 |  |
| sensitive | 19 | 23.17 | 18 | 42.86 |  |
| N/A | 6 | 7.32 | 5 | 11.9 |  |
| Mean age (range) | 62 | (33-94) | 58 | (33-82) | 0.13 |

C. CT45 is a Native Tumour Antigen

Cancer-testis antigens are aberrantly expressed in a wide range of cancers while their physiological expression is typically limited to immunocompromised tissues such as the testis and placenta thus making them ideal candidates for cancer immunotherapy (7, 8). CT45 has yet to have been shown to be antigenic. Endogenous CT45 protein expression was detected in only two out of eight epithelial ovarian cancer cell lines (FIG. 5a) and the same pattern was evident at the mRNA level (FIG. 5b). In order to ascertain whether CT45-derived peptides could be bound and presented in human leukocyte antigen (HLA) class I complexes on the surface of CT45+ ovarian cancer cells, the inventors used a previously established immuno-peptidomics strategy (16) (FIG. 5c). The inventors identified five HLA-I A*03:01 and A*11:01 specific peptides (AVDPETVFK (SEQ ID NO: 1), GVQGPTAVR (SEQ ID NO:2), GVQGPTAVRK (SEQ ID NO:3), VQGPTAVRK (SEQ ID NO: 4), QGPTAVRK (SEQ ID NO:5)) presented in the 59M cell line which fit the typical length of HLA-I peptides of 8 to 11 amino acids. To determine which of these peptides could serve as targets for CD8+ T cells, A*03:01 CD8+ T cells collected from the ascites of a patient with a CT45+ tumor were cultured with each peptide. All five peptides were able to induce proliferation of the CD8+ T cell population as shown by increased Ki67 staining and induced CT45 specific T cell responses as assessed by intracellular IFN-γ staining (FIG. 2a). Similar results were also obtained using A*11:01 CD8+ tumor infiltrating lymphocytes (TILs) isolated from the omental tumor of a separate patient with a CT45+ tumor (FIG. 5D). These results demonstrate that CT45 is an antigenic target in ovarian cancer patients.

Recently it's been demonstrated that CT45 expression is regulated by methylation (5) and patients treated with demethylating agents showed an altered immune response that correlated with upregulation of CT antigens as well as genes involved in immunomodulatory pathways (17,18). Therefore, the inventors tested whether treatment with 5-aza-2'-deoxycytidine (DAC) would activate CT45 expression and peptide presentation in ovarian cancer cells. Treatment with DAC activated CT45 expression in SKOV3ip1 cells (FIG. 6a) and using the same immune-peptidomics strategy as previously described, the inventors identified three peptides derived from CT45 capable of binding A*3:01 and A*68:01 (FIG. 2b, FIG. 6b). Culture with all three peptides resulted in increased Ki67 staining of A*03:01 CD8+ T-cells collected from the ascites of a patient with a CT45+ tumor and increased the percentage of IFN-γ and IL-2 double positive T cells. The majority of the CT45-derived peptides identified were predicted by two different algorithms to have low and intermediate affinity for the three HLA-I types. Only one peptide was predicted to have high affinity (AVDPETVFK—SEQ ID NO:1). All peptides ranked in the top 50% for predicted immunogenicity although the peptide with highest ranking, AVDPETVFK (SEQ ID NO: 1), did not consistently stimulate the most robust T cell response underscoring the limits of relying solely on the predictive algorithms.

D. Functional Mediator of Chemosensitivity

Figure 3A:
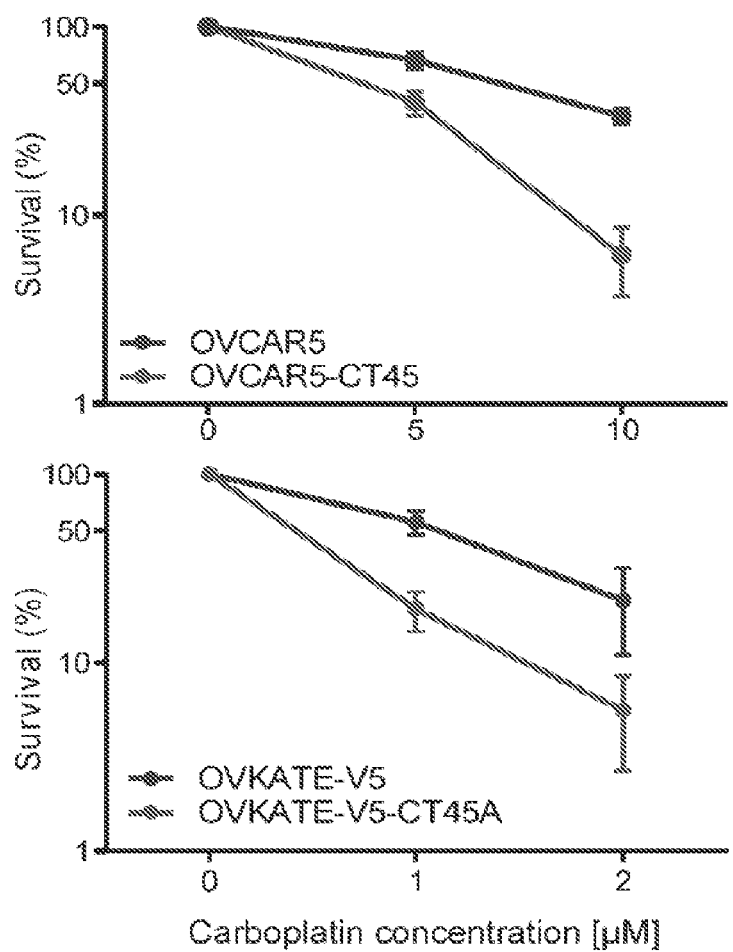
FIG. 3A-F. CT45 mediates chemotherapy sensitivity. a, Clonogenic survival of the ovarian cancer cell lines OVCAR5 (upper) and OVKATE (lower) stably overexpressing CT45 or controls. Dots represent mean values from three independent experiments. Error bars show standard deviations. b, c, Interaction proteomics screen in two ovarian cancer cell lines OVCAR-5 (c) and COV318 (d) stably over-expressing CT45 tagged with 3×-FLAG (OVCAR5) or V5 (COV318), respectively. Protein enrichment (t-test difference) was calculated over the corresponding control cell line (FLAG or V5 alone) and plotted against the t-test p-value (−log 10). Dashed lines indicate significance thresholds. The bait protein CT45 and members of the protein phosphatase 4 complex are highlighted. Results represent 3-4 replicates per experiment group. d, Western blot of cleaved caspase-3, γH2AX, and CT45 following treatment with carboplatin and paclitaxel. Day 5. e, Comet assay following carboplatin treatment at Day 5. Data are means±s.e.m. of 4 independent replicates (left). Representative images of comets are shown (right) f, Growth of OVCAR5-V5 (control plasmid) and OVCAR5-V5-CT45 tumors (N=5-8) over time during treatment with carboplatin. Data are means±s.e.m. for each group.

The inventors found that pretreatment of ovarian cancer cells with DAC sensitized the cells to carboplatin (FIG. 7a). Proteomic analysis on DAC treated ovarian cancer cells revealed upregulation of many CT antigens in addition to CT45 (FIG. 7b). While CT antigens are commonly expressed in many different cancers, very few have been linked to specific biological functions (7). CT45 has been previously described to have tumor promoting effects in cancer cell lines (22, 23) and to correlate with poor prognosis in several cancer types (5, 10, 11). To investigate if CT45 plays a direct role in mediating chemosensitivity, the inventors next tested the functional consequences of CT45 over-expression in human ovarian cancer cell lines (FIG. 8a). Overexpression of CT45 using a lentiviral construct in the ovarian cancer cell line OVCAR-5 showed no effect on proliferation (FIG. 8b). However, when cells were treated with carboplatin, CT45 expression significantly reduced proliferation and colony formation in a dose-dependent manner (FIG. 3a and FIG. 8b).

Figures 3B, 3C:
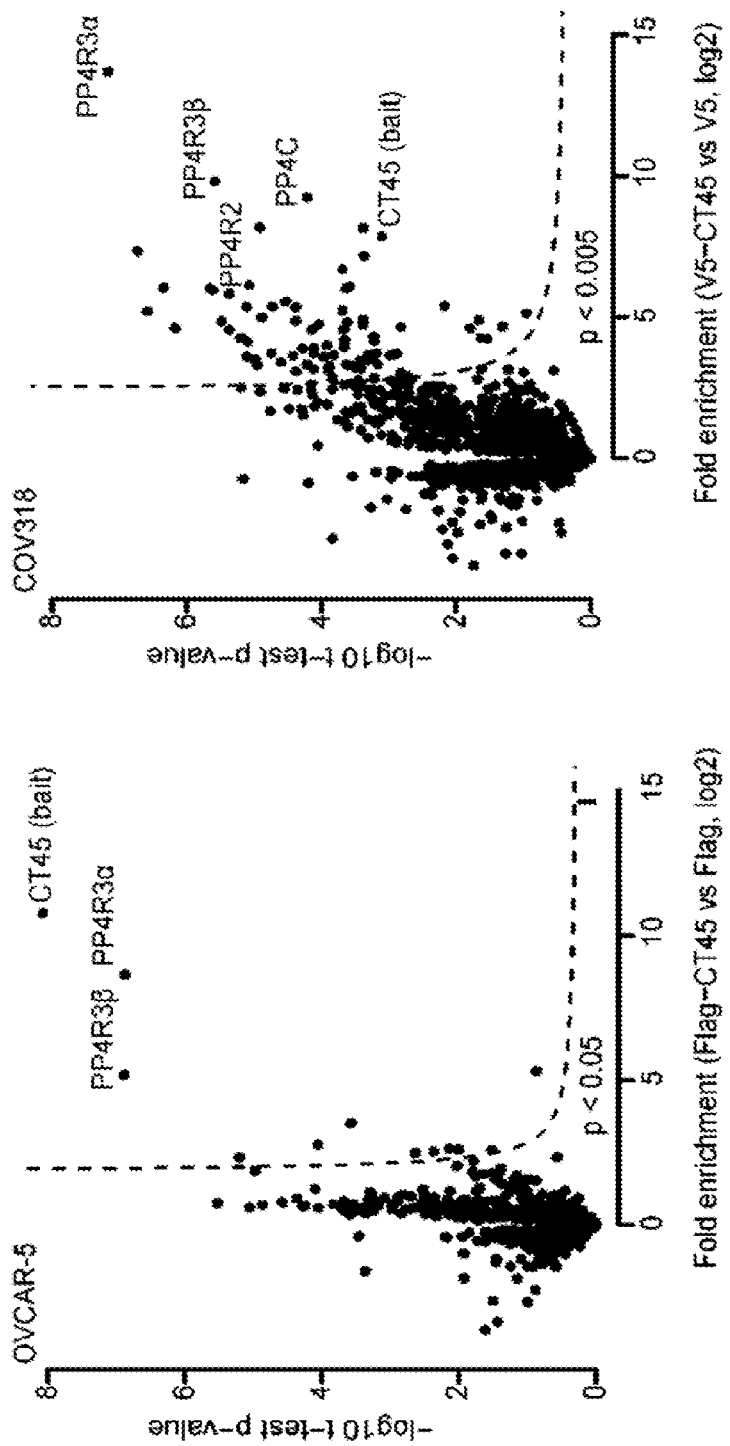
Figure 3D:
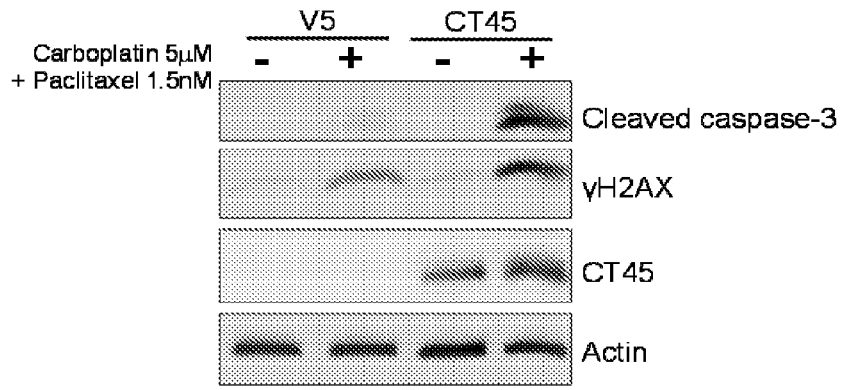
Figure 3E:
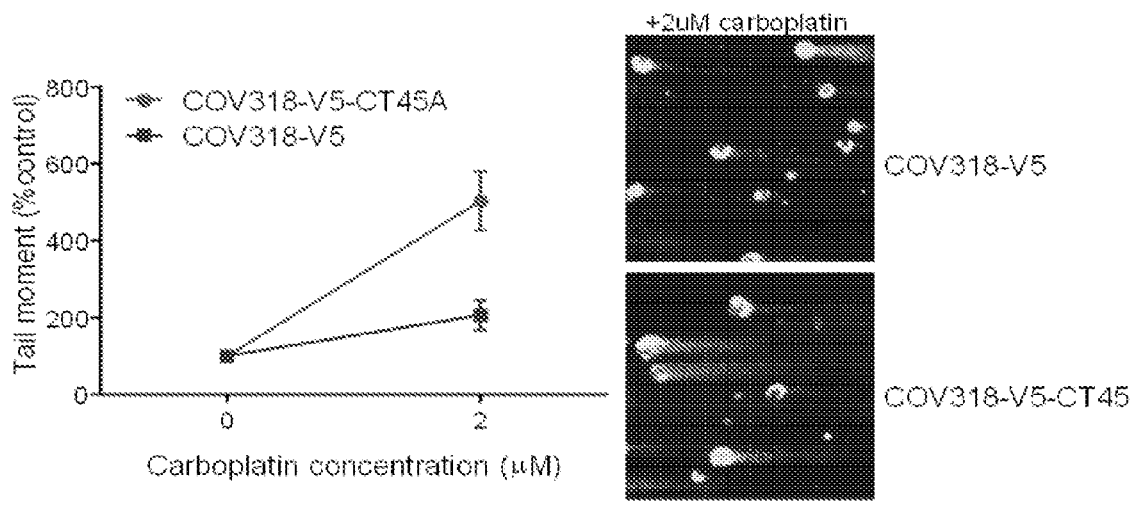

In order to understand the mechanism of CT45-mediated chemosensitivity, the inventors used an interaction proteomics approach (24) to identify CT45 interaction partners. The inventors screened two ovarian cancer cell lines (OVCAR-5 and COV318) both expressing V5-tagged CT45A5 and compared the enriched immuno-precipitates to the corresponding control cell lines (V5 tag alone). The strongest co-enriched proteins were PP4R3α and PP4R3β (FIG. 3b, 3c), two highly conserved regulatory subunits of the protein phosphatase 4 (PP4) complex pointing to their specific and direct interaction with CT45. Furthermore, the catalytic subunit of the PP4, PP4C, as well as PP4R2 were also enriched in CT45 immuno-precipitates. The PP4 complex is known to dephosphorylate critical members of the DNA damage response (DDR) including 53BP1 (25), γH2AX (26), RPA2 (27), and TRIM28/Kap-1 (28, 29). Therefore, it was next asked if CT45 expression affected the DDR following carboplatin treatment. CT45-expressing cancer cells had increased levels of γH2AX and cleaved caspase-3 following treatment with carboplatin (FIG. 3d). Consistent with this, higher levels of DNA damage was also present in CT45-expressing cells as assessed by the comet assay with longer tail moments being observed (FIG. 3e).

Figure 3F:
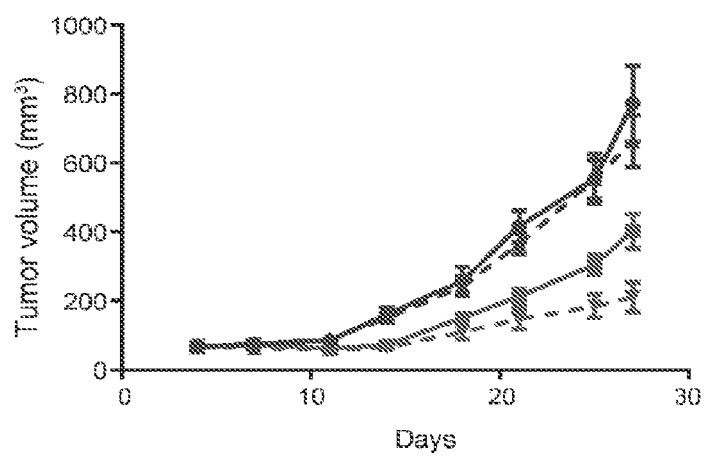

To investigate the effect of CT45 expression on tumor growth in an immunodeficient background, OVCAR-5 control vector or CT45 expressing cells were injected subcutaneously in nude mice. Treatment with carboplatin significantly reduced growth of CT45 expressing tumors as compared to the untreated CT45 tumors while having no effect on the control cell line (FIG. 3f). Interestingly, CT45 expression also significantly reduced overall tumor growth as compared to the control vector (FIG. 3f) which was not observed in vitro (FIG. 8b). This data clearly reveals a functional link between CT45 expression and carboplatin chemosensitivity as well as highlights the potential tumor-suppressive capacities of CT45.

E. Methods

1. Cell Lines and Reagents

SKOV3ip1, OVCAR5 (UCSF) and COV318 (from Dr. Gottfried Konecny, UCLA) were cultured in DMEM, 10% FBS. 59M (ECACC) was cultured in DMEM, 10% FBS supplemented with 10 µg/ml bovine isulin (Sigma, MO). OVKATE were cultured in RPMI-1640, 10% FBS. All cell lines have been tested for mycoplasma and authenticated using the commercial service, CellCheck (IDEXX Bioresearch). Growth factor reduced Matrigel was from BD Biosciences (Rockville, MD). pLX30434 corresponds to Addgene plasmid #25890. pLX304-CT45A5 was acquired from DNASU Plasmid Repository 35-37 (clone HsCD00446210). The Ki-CT45-2 antibody (used for WB and IMF) was a kind gift from a colleague. W6/32 monoclonal antibodies were purified from the growth medium of HB95 cells that were grown in CELLine CL-350 flask (Wilson Wolf Manufacturing Corporation, Minnesota) using Protein-A Sepharose (Invitrogen, CA). Antibodies acquired from Cell Signaling Technology were: γH2AX (9718, rabbit), Cleaved Caspase-3 (9661), anti-rabbit IgG-HRP (#7074), and anti-mouse IgG-HRP (#7076). Other antibodies used were: actin (Sigma, #A5441), anti-CT45A antibody (Sigma, SAB1301842), γH2AX (mouse, Thermo Scientific, #MA1-2022), and V5 (Life Technologies, #MA5-15253).

2. FFPE Tissue Preparation for MS Analysis

FFPE biobank specimens (5 serial sections, 10 µM thick) were first deparaffinized as previously described38. Areas containing 70% or more tumor were macrodissected from the slide using a scalpel blade. Lysis was then carried out in 4% SDS, 10 mM Hepes pH 8.0 at 99° C. for 60 min and by 15 min sonication (level 5, Bioruptor, Diagenode). Proteins in the cleared lysate (16,000 g, 10 min) were reduced with 10 mM DTT for 30 min and alkylated with 55 mM iodoacetamide for an additional 30 min. SDS detergent was removed by acetone precipitation. Briefly, acetone (−20° C.) was added to 100 µg of proteins to a final concentration of 80% v/v and proteins were precipitated overnight at −20° C. After centrifugation (15 min, 4° C., 16,000 g), the detergent-containing supernatant was removed and the protein pellet washed with 80% acetone (−20° C.). Protein pellets were then resolved in 100 µl 6 M urea/2 M thiourea (in 10 mM Hepes pH 8.0) and digested with 1 µg of LysC for 3 h at room temperature. After adding 4 volumes of 50 mM ammonium bicarbonate, 1 µg trypsin was added and tryptic digestion carried out overnight. The next day, digestion was stopped by adding 1% TFA. Peptides were finally desalted on C18 StageTips and kept at −20° C. until MS analysis.

3. Liquid Chromatography (LC)-MS Analysis of FFPE Samples

Desalted peptides were separated on a Thermo Scientific EASY-nLC 1000 HPLC system (Thermo Fisher Scientific).

Columns (75 µm inner diameter, 50 cm length) were in-house packed with 1.9 µm C18 particles (Dr. Maisch GmbH, Germany). Peptides were loaded in buffer A (0.5% formic acid) and separated with a 250-min gradient from 2% to 60% in buffer B (80% acetonitrile, 0.5% formic acid) at 200 nl/min. An in-house-made column oven was used to set the column temperature to 50° C. Quadrupole Orbitrap mass spectrometer (Q Exactive, Thermo Fisher Scientific) coupled to the LC via a nano electrospray source was operated in data-dependent mode. The survey scan range was set to 300 to 1,650 m/z with a resolution of 70,000 at m/z 200. Up to the 5 most abundant isotope patterns with a charge ≥2 were subjected to high-energy collisional dissociation fragmentation71 at a normalized collision energy of 25, an isolation window of 2.2 Th, and a resolution of 17,500 at m/z. To limit repeated sequencing, dynamic exclusion of sequenced peptides was set to 45 s. Thresholds for ion injection time and ion target values were set to 20 ms and 3E6 for the survey scans and 120 ms and 1E5 for the MS/MS scans, respectively. Data was acquired using Xcalibur software (Thermo Scientific).

4. Data Analysis of FFPE Samples

MS raw files were analyzed with MaxQuant software20 (version 1.5.0.38). MS/MS based peptide identification was carried out with the *Andromeda* search engine in Max-Quant19. Briefly, *Andromeda* uses a target-decoy approach to identify peptides and proteins at an FDR of less than 1%. As a forward database, the human UniProtKB database (October 2014) was used. A reverse database for the decoy search was generated automatically in MaxQuant. Enzyme specificity was set to "Trypsin", and a minimum number of 7 amino acids were required for peptide identification. Default settings were used for variable and fixed modifications (variable modification, acetylation [N-terminus] and methionine oxidation; fixed modification, carbamidomethylation). Proteins and protein isoforms that could not be discriminated by unique peptides were grouped into protein groups. For label-free protein quantification, the MaxLFQ algorithm was used as part of the MaxQuant environment. Briefly, quantitative information was retrieved based on high-resolution 3D peptide profiles in mass-to-charge, retention time and intensity space. The algorithm first calculated pairwise protein ratios by taking the median of all pairwise peptide ratios per protein. Only shared identical peptides were considered for each pairwise comparison. A minimum number of 1 ratio count was required for each pairwise comparison. To retrieve quantitative information for all possible sample comparisons, a least-squares analysis was used to reconstruct the relative abundance profile for each protein. This step preserved the total summed intensity for a protein over all samples. To maximize the number of quantification events across samples, the inventors enabled the "Match Between Runs" option in MaxQuant, which allowed the quantification of high-resolution MSI features that were not identified in each single measurement.

5. Tissue Microarray

Tissue microarrays (TMAs) were deparaffinized and rehydrated through xylenes and serial dilutions of EtOH to deionized water. They were incubated in antigen retrieval buffer (Tris-EDTA, pH 9, S2367, DAKO) and heated in steamer at over 97 degree C. for 20 minutes. Anti-CT45A (1:200) antibody (Sigma, SAB1301842) was applied on tissue sections for one hour incubation at room temperature in a humidity chamber. The antigen-antibody binding was detected by Bond Polymer Refine Detection (DS9800, Leica Microsystems). Tissue sections were briefly immersed in hematoxylin for counterstaining and were covered with cover glasses. The stained TMAs were scored by an expert pathologist on a scale from 0-3. Data acquisition and analysis were blinded.

6. HLA-I Peptide Purification

SKOV3ip1 cells were treated with 500 nM 5-aza-2'-deoxycytidine (DAC, also known as Decitabine) (Sigma, MO) for 3 days with DAC refreshed every 24 hours. After treatment cells were cultured an additional 4 days without DAC and collected for HLA-I purification at day 7. HLA-I peptidomes were obtained from 3 biological replicates for 59M and DAC treated SKOV3ip1 cell lines. HLA-I complexes were purified from about 1×108 cells after lysis with 0.25% sodium deoxycholate, 0.2 mM iodoacetamide, 1 mM EDTA, 1:200 Protease Inhibitors Cocktail (Sigma, MO), 1 mM PMSF, 1% octyl-β-D glucopyranoside (Sigma, MO) in PBS at 4° C. for 1 h. The lysates were then cleared by 30 min centrifugation at 40,000×g. Immunoaffinity purification of HLA-I molecules was carried out by using the W6/32 antibody covalently bound to Protein-A Sepharose beads (Invitrogen, CA). Columns were washed with 10 column volumes of 150 mM NaCl, 20 mM Tris. HCl (buffer A), 10 column volumes of 400 mM NaCl, 20 mM Tris·HCl, 10 volumes of buffer A again and finally with seven column volumes of 20 mM Tris·HCl, pH 8.0. HLA-I molecules were eluted at room temperature by adding 500 ul of 0.1 N acetic acid, in a series of 7 elutions for each sample. Small aliquots of each elution fraction were analyzed by SDS-PAGE to evaluate the yield and purity of the eluted HLA-I. Eluted HLA-I peptides and the subunits of the HLA complex were loaded on Sep-Pak tC18 cartridges (Waters, MA) that were pre-cleaned with 80% acetonitrile (ACN) in 0.1% trifluoroacetic acid (TFA) and with 0.1% TFA only. After loading, the cartridges were washed with 0.1% TFA. HLA-I peptides were separated from HLA-I heavy chains by eluting with 30% ACN in 0.1% TFA. An additional purification was done using Silica C-18 column tips (Harvard Apparatus, MA). Peptides were eluted again with 30% ACN in 0.1% TFA. Finally, HLA-I peptides were concentrated to 15 µl by vacuum centrifugation. For MS analysis, the inventors injected 5 µl for each measurement. HLA-I genotypes were determined using high-resolution genotyping (Center for Human Genetics and Laboratory Medicine, Martinsried).

7. LC-MS/MS Analysis of HLA-I Peptides.

HLA peptides were separated by a nanoflow HPLC (Proxeon Biosystems, Thermo Fisher Scientific, Odense) and coupled on-line to a Q Exactive mass spectrometer (Thermo Fisher Scientific, Bremen) with a nanoelectrospray ion source (Proxeon Biosystems). An in-house packed 20 cm long, 75 µm inner diameter column with ReproSil-Pur C18-AQ 1.9 µm resin was used (Dr. Maisch GmbH, Ammerbuch-Entringen, Germany) in buffer A (0.5% acetic acid). Peptides were eluted with a linear gradient of 2-30% buffer B (80% ACN and 0.5% acetic acid) at a flow rate of 250 nl/min over 120 min. Up to the 10 most abundant isotope patterns with a charge state of 1-3 (unassigned ion charge states, or charge states of four and above were excluded) were subjected to high-energy collisional dissociation fragmentation at a normalized collision energy of 27 an isolation window of 1.4 Th and a resolution of 15,000 at 200 m/z. To limit repeated sequencing, dynamic exclusion of sequenced peptides was set to 20 s. Thresholds for ion injection time and ion target values were set to 20 ms and 3E6 for the survey scans and 120 ms (220 ms for 59M) and 1E5 for the MS/MS scans, respectively. Data was acquired using Xcalibur software (Thermo Scientific).

The inventors acquired full scan MS spectra at a resolution of 70,000 at 200 m/z with a target value of 3e6 ions. The ten most intense ions were sequentially isolated and accumulated to an AGC target value of 1e5 with a maximum injection time of generally 120 ms, except for the 59M cell line we used 220 ms to increase signal of the fragments. In case of unassigned precursor ion charge states, or charge states of four and above, no fragmentation was performed. The peptide match option was disabled. MS/MS resolution was 17,500 at 200 m/z. Fragmented m/z values were dynamically excluded from further selection for 15 or 20 seconds.

8. Data Analysis of HLA Peptidomes

The inventors used the MaxQuant computational proteomics platform version 1.5.0.38. *Andromeda*, a probabilistic search engine incorporated in the MaxQuant framework, was used to search the peak lists against the UniProt database (October 2014). N-terminal acetylation (42.010565 Da) and methionine oxidation (15.994915 Da) were set as variable modifications. The second peptide identification option in *Andromeda* was enabled. The enzyme specificity was set as unspecific. *Andromeda* reports the posterior error probability and false discovery rate, which were used for statistical evaluation. A false discovery rate of 0.01 was required for peptides. As the inventors were interested in HLA-I peptide identification rather than protein identification common in proteomics, no protein false discovery rate was set. Likewise, as no sequence specific proteases were involved and peptides did not terminate in certain amino acids such as Arg or Lys, the special permutation rules in MaxQuant for these amino acids were not used in creating the decoy database. Possible sequence matches were restricted to 8 to 15 a.a., a maximum peptides mass of 1,500 Da and a maximum charge states of three. The initial allowed mass deviation of the precursor ion was set to 6 ppm and the maximum fragment mass deviation was set to 20 ppm. From the 'peptides.txt' output file produced by MaxQuant, hits to the reverse database and contaminants were eliminated.

9. T Cell Peptide Stimulation

Tumors and ascites were collected from patients undergoing primary debulking surgery by a gynecologic oncologist at the University of Chicago Hospital, Department of Obstetrics and Gynecology, Section of Gynecologic Oncology. Informed consent was obtained before surgery and the study was approved by the IRB of the University of Chicago.

10. Colonogenic Survival Assay

Cells were treated with different carboplatin concentrations for 48 hours and 7-9 days after treatment colonies were counted and plotted as a percent of control on a logarithmic scale.

11. Western Blot Analysis

Cells were treated with 5 µM carboplatin plus 1.5 nM paxlitaxel for 3 days and then incubated an additional 2 days without drug prior to collection on day 5. Both adherent and non-adherent cells were collected in RIPA buffer (25 mM Tris-HCl pH 7.6, 150 mM NaCl, 1% NP-40, 0.5% sodium deoxycholate, 0.1% SDS) supplemented with protease inhibitor cocktail (Thermo Scientific) and phosphatase inhibitor cocktail (Sigma). Lysates were incubated for 30 min on ice before centrifugation (15 min, 14 000 rpm, 4° C.). The quantity of protein was determined by BCA reagent (Pierce). The extracts were analyzed by SDS-PAGE on a 4-20% gradient gel (Bio-Rad).

12. Comet Assay

Cells were treated with carboplatin for 3 days and then incubated an additional 2 days without drug. The comet assay was performed on day 5 as previously described39. Briefly, 2.5e4 cells/condition were resuspended in 70 uL 0.5% low melting point agarose (LMPA) at 37 C and plated on a glass slide precoated with 1% agarose in PBS. Samples were allowed to solidify at 4 C for 20 minutes with a square cover glass. The cover class was gently removed and a second 70 uL layer of 0.5% LMPA was applied and again allowed to solidify. The cover glass was removed and the slides immersed in Comet Lysis solution (2.5M NaCl, 100 mM EDTA, 10 mM Tris, 0.015% Triton X-100, pH 10) for one hour at 4 C and from this point forward protected from light. After lysis, the slides were equilibrated for 20 minutes in Comet Electrophoresis Buffer (0.3N NaOH, 1 mM EDTA, pH 10) at 4 C, and then run at 25V for 20 minutes. Then the slides were incubated at room temp in Comet Neutralization Buffer (0.4M Tris, pH 7.5) for five minutes twice, then in ddH2O for three minutes, stained with a 1:10,000 dilution of SYBR Gold in ddH2O, and finally mounted with a glass cover slip for imaging. Images were taken at 10× using a Zeiss AxioObserver A.1. At least 100 cells were quantified/sample using the software OpenComet40. Data shown is the mean+s.e.m. of 4 biological repeats.

13. Mouse Experiments 5 million OVCAR5-V5 or OVCAR5-V5-CT45 cells suspended in a 1:2 solution of serum-free media to growth-factor reduced matrigel were injected subcutaneously into the right and left flanks respectively, of 8 week old female athymic nude mice. After 5 days, treatment was administered through the tail vein 1 time/week at 20 mg/kg. Sterile water served as the control treatment. Tumor growth was measured every 2-3 days using calipers until the tumor neared 1 cm3 and was measured daily. Once the tumor reached 1 cm3 the mouse was sacrificed. 4 mice were removed from the study early due to ulcerations of the skin. All experiments were approved by the Institutional Animal Care and Use Committee of the University of Chicago.

14. Statistical Analysis

For analysis of clinicopathological data, comparisons between groups were performed using chi-squared or Fisher's exact tests for categorical variables and Wilcoxon rank-sum tests for continuous variables. Overall survival and disease-free survival was compared between groups using the log-rank test. Disease-free survival can be the length of time after treatment for a cancer ends that the patient survives without any signs or symptoms of that cancer. In a clinical trial, measuring the disease-free survival is one way to see how well a new treatment works. Also called DFS, relapse-free survival, and RFS. The association between CT45 levels and days of chemoresistance was assessed using a Spearman rank correlation coefficient. Statistical analyses were performed using Stata Version 14 (Stata Corp., College Station, TX).

All other statistical analyses were performed using GraphPad Prism (GraphPad). Sample sizes were determined based on previous experience with the individual experiment except for animal studies where power calculations were used. With the exception of the tissue microarray analysis, no randomization or blinding was done for data acquisition or assessment of outcome. The mean and the standard error of the mean (s.e.m) indicating variance are reported for all graphs. For experiments making one comparison, data was analyzed using a two-tailed Mann Whitney U test to account for non-normal distribution of the data. For experiments with more than one comparison, One-Way ANOVA with Tukey's multiple comparisons post-test was used. Before applying ANOVA, the inventors first tested whether the variation was similar among the groups using the Bartlett's test. Where the standard deviations were significantly different, a log 2 transformation was applied to the data before analysis. Differences were considered significant if p<0.05.

Example 2: Proteomics Identifies CT45 as a Mediator of Chemosensitivity and Immunotherapy Target in Ovarian Cancer Most high-grade serous ovarian cancer (HGSOC) patients will develop resistance to platinum-based chemotherapy but a subset (15%) will remain disease-free for over a decade. To discover drivers of long-term survival following chemotherapy, the inventors analyzed the proteomes of 25 platinum resistant and sensitive HGSOC patients to a depth of over 9,000 proteins. The inventors identified cancer/testis antigen 45 (CT45) as an independent prognostic factor for prolonged disease-free survival. Immunopeptidomics discovered several CT45 derived HLA class I peptides capable of activating patient-derived cytotoxic T cells. Interaction proteomics identified a direct interaction with members of the protein phosphatase 4 (PP4) complex linking CT45 to the DNA damage response. CT45 mediates chemosensitivity by impeding PP4-dependent KAP-1 dephosphorylation following DNA damage leaving the heterochromatin in an open conformation and making it susceptible to carboplatin toxicity. Thus, CT45 is a novel regulator of chemosensitivity and is a potential target for immunotherapy.

A. Identification of CT45 by Shotgun Proteomics

The inventors performed quantitative proteomics on FFPE tumor samples isolated from 25 chemotherapy-naïve patients with advanced stage HGSOC (FIG. 10A, 14A, Table 3). Since patients with advanced stage disease generally have the worst prognosis, metastatic tumors from the omentum were selected for proteomic analysis. The inventors first assessed global proteomic differences between chemoresistant (N=11, median DFS=190 days) and chemosensitive (N=14, median DFS=1160 days) patients in the cohort by adapting a recently described and highly sensitive label-free proteomic workflow capable of accurately quantifying a large portion of the cellular proteome. More than 9,000 proteins from low input archival samples were stringently identified and quantified in single-run measurements in the MaxQuant environment (1% FDR at protein and peptide levels; FIG. 14B). The dynamic range of protein signals spanned more than six orders of magnitude (FIG. 14C). Pearson R values between all specimens were consistently above 0.77 (mean 0.88) and the correlation was 0.95 between independently prepared tissue of the same tumor (FIG. 14D). Based on the quantitative levels of 8,190 proteins after data filtering (Methods, FIG. 14B), the inventors observed few overall proteome changes across patients. However, the comparison of chemosensitive and chemoresistant patients identified cancer/testis antigen 45 (CT45), as significantly higher expressed in chemosensitive patients (FDR<5%, FIG. 10B). Furthermore, CT45 protein levels strongly correlated with disease-free survival time (FIG. 15A). CT45 is comprised of 10 distinct but highly similar genes, which make them nearly identical at the protein level (amino acid identity >98%, FIG. 4). Immunohistochemistry for CT45 confirmed the relative expression of CT45 in serial sections of the tumors used in the proteomic cohort and showed localization to the nucleus and in some cases to the nucleolus (FIG. 10C).

TABLE 3

| Patient | Platinum Value | Days to platinum resistance | Disease free days | Overall survival days | Status | Refractory |
|---|---|---|---|---|---|---|
| 2 | Resistant | −54 | 114 | 241 | deceased | y |
| 24 | Sensitive | 2584 | 2754 | 2903 | deceased | n |
| 8 | Resistant | 31 | 211 | 228 | deceased | n |
| 3 | Resistant | −22 | 114 | 1489 | deceased | y |
| 13 | Sensitive | 382 | 573 | 1479 | deceased | n |
| 18 | Sensitive | 971 | 1133 | 1716 | deceased | n |
| 25 | Sensitive | 3100 | 3229 | 3229 | alive | n |
| 14 | Sensitive | 440 | 580 | 1106 | deceased | n |
| 5 | Resistant | 18 | 161 | 363 | deceased | n |
| 20 | Sensitive | 1111 | 1296 | 3046 | alive | n |
| 21 | Sensitive | 1271 | 1498 | 1573 | deceased | n |
| 11 | Resistant | −37 | 391 | 567 | deceased | n |
| 23 | Sensitive | 2478 | 2603 | 2603 | alive | n |
| 16 | Sensitive | 462 | 663 | 1347 | deceased | n |
| 7 | Resistant | 20 | 210 | 345 | deceased | n |
| 17 | Sensitive | 864 | 1008 | 1528 | deceased | n |
| 4 | Resistant | 29 | 155 | 485 | deceased | n |
| 10 | Resistant | 104 | 366 | 922 | deceased | n |
| 12 | Sensitive | 366 | 552 | 973 | deceased | n |
| 6 | Resistant | 52 | 190 | 790 | deceased | n |
| 9 | Resistant | 134 | 335 | 1118 | deceased | n |
| 15 | Sensitive | 397 | 588 | 1078 | deceased | n |
| 22 | Sensitive | 1665 | 1804 | 1804 | alive | n |
| 19 | Sensitive | 1051 | 1188 | 1467 | alive | n |
| 1 | Resistant | 11 | 113 | 280 | deceased | y |

To validate the proteomic findings in a larger patient cohort, the inventors stained tissue microarrays (TMA) to analyze CT45 expression in over 200 cases of primary and metastatic ovarian cancer (FIG. 16A). CT45 protein levels were assessed by a gynecologic pathologist blinded to patient outcomes. CT45 was only rarely expressed in cases of endometrioid, clear cell, or mucinous ovarian cancer subtypes compared to serous papillary—in line with a previous study of mRNA expression—and the protein was expressed at identical levels between primary and metastatic tumors from the same HGSOC patients. Consistent with the discovery cohort, CT45 expression correlated with chemosensitivity in 124 patients with advanced stage HGSOC (FIGO 2014 stage IIIb or higher) (P=0.005, FIG. 16A). Furthermore, patients with high CT45 expression (staining 1+) had prolonged disease-free survival compared to patients with no expression of CT45 (P=0.02, 363 days versus 153.5 disease free days; FIG. 10D) and there was a trend towards longer overall survival (P=0.09, FIG. 16B). Thus, CT45 expression is an independent prognostic indicator for advanced stage HGSOC.

B. CT45 is a Native Tumor Antigen

Figure 17A:
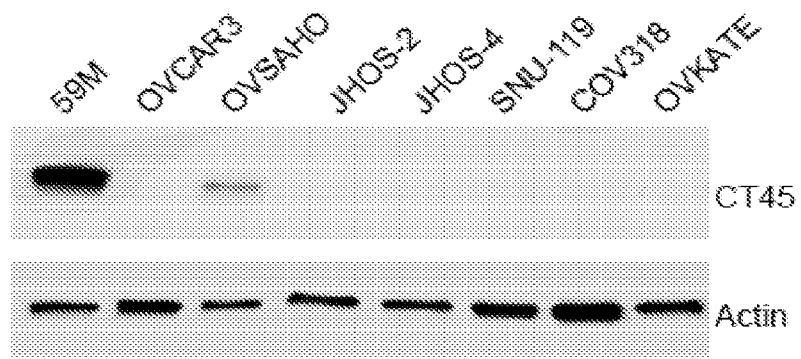
Figure 17B:
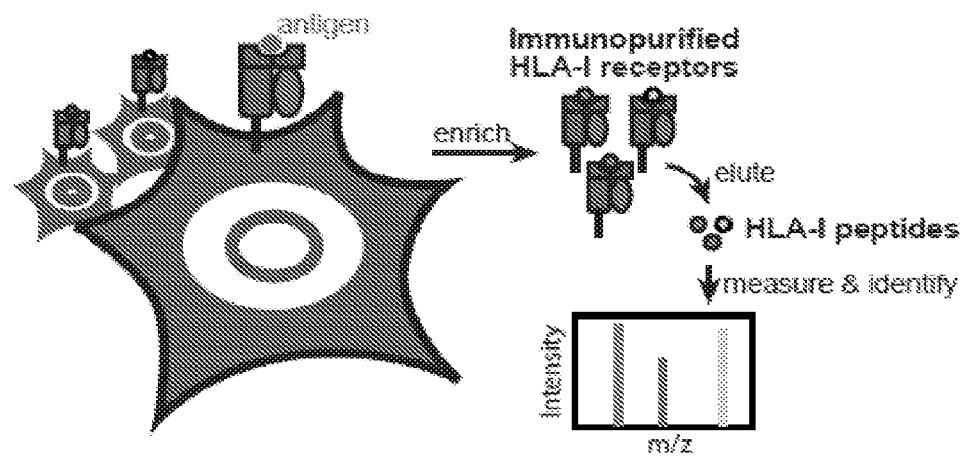
Figure 17F:
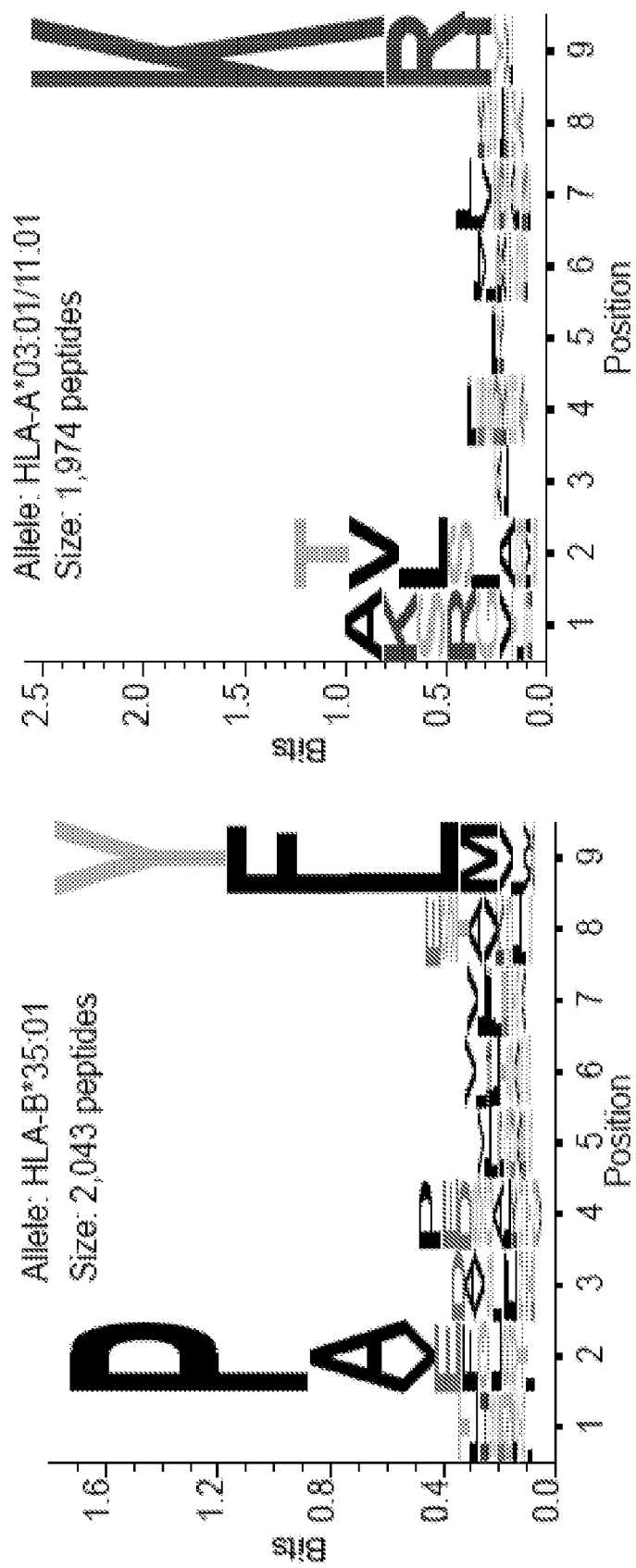
Figure 17G:
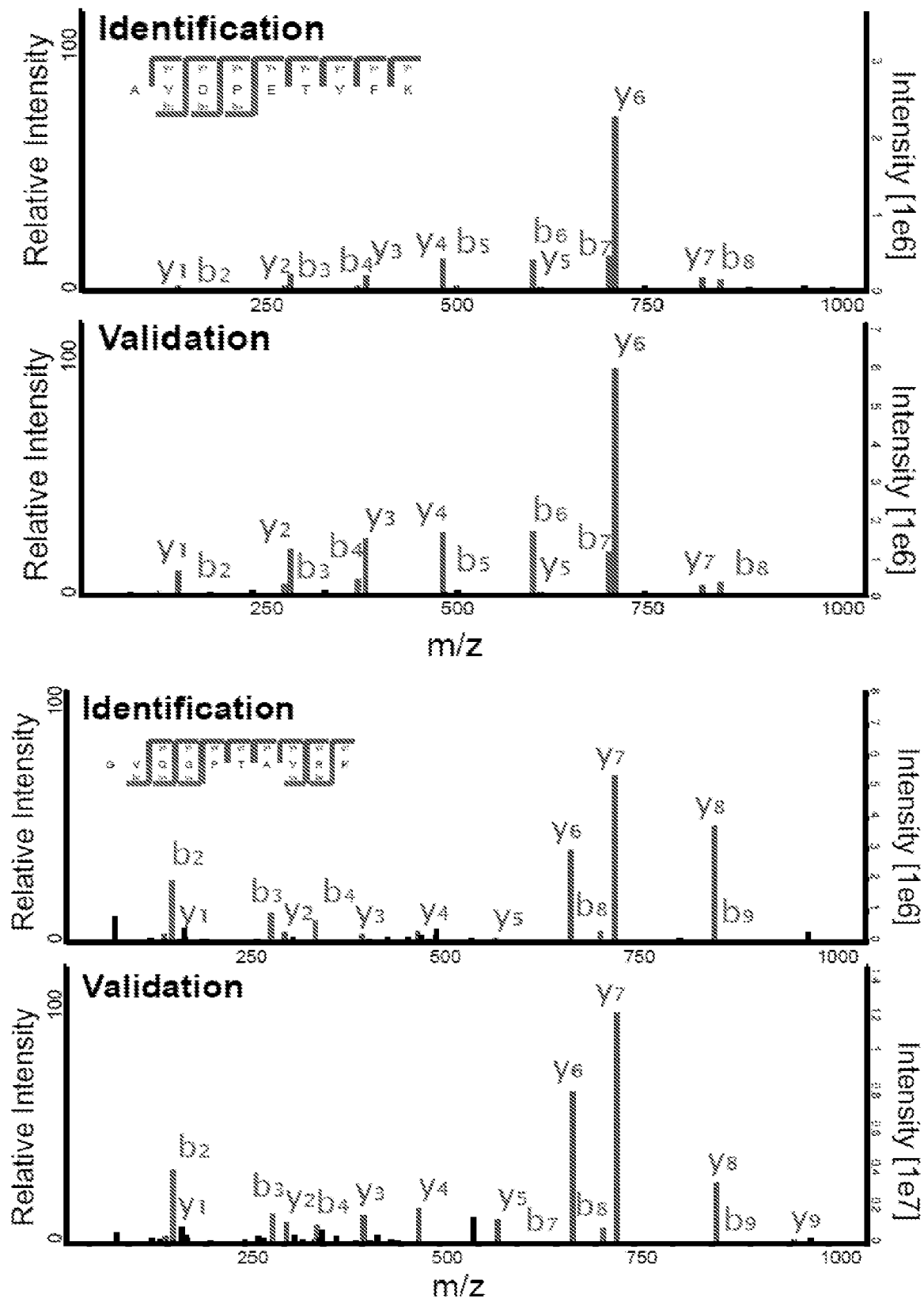

The role of CT45 as a tumor antigen has not been elucidated. To investigate whether CT45-specific peptides are bound and presented on human leukocyte antigen (HLA) class I complexes on cancer cell lines, the inventors used an approach coupling immunopeptidomics to mass spectrometry with a cell line (59M) expressing high endogenous levels of CT45 (FIG. 17A-B). Of 6,413 identified HLA-I peptides (FIG. 17C), five derived from CT45: AVDPETVFK (SEQ ID NO: 1), GVQGPTAVR (SEQ ID NO:2), GVQGPTAVRK (SEQ ID NO:3), VQGPTAVRK (SEQ ID NO:4), QGPTAVRK (SEQ ID NO:5); all of which matched the binding motifs of the A-03:01 and A-11:01 HLA-I receptor (FIG. 17D-F). The identity of these peptides was further confirmed using synthetic versions and tandem mass spectrometry (FIG. 17G). In-silico HLA epitope prediction revealed weak and strong binding affinity of AVDPETVFK (SEQ ID NO:1) to A-03:01 or A-11:01, respectively, and low or no binding affinity for the remaining four peptides (FIG. 11A).

CT45 expression is regulated by DNA methylation and patients treated with demethylating agents show an altered immune response that correlates with upregulation of cancer/testis antigens as well as genes involved in immunomodulatory pathways. Treatment with 5-aza-2'-deoxycytidine (DAC) strongly activated CT45 expression in SKOV3ip1 ovarian cancer cells (FIG. 11B, FIG. 18A) along with the CT antigens NY-ESO-1, MAGEA4 and SSX2, in line with recent publications. Using the same immunopeptidomics strategy, the inventors indentified three additional, but sequence related CT45 peptides matching to the measured peptide motifs (FIG. 12A) of the alleles A-03:01 and/or A-68:01 (FIG. 11C, FIGS. 18B-D).

Figure 18E:
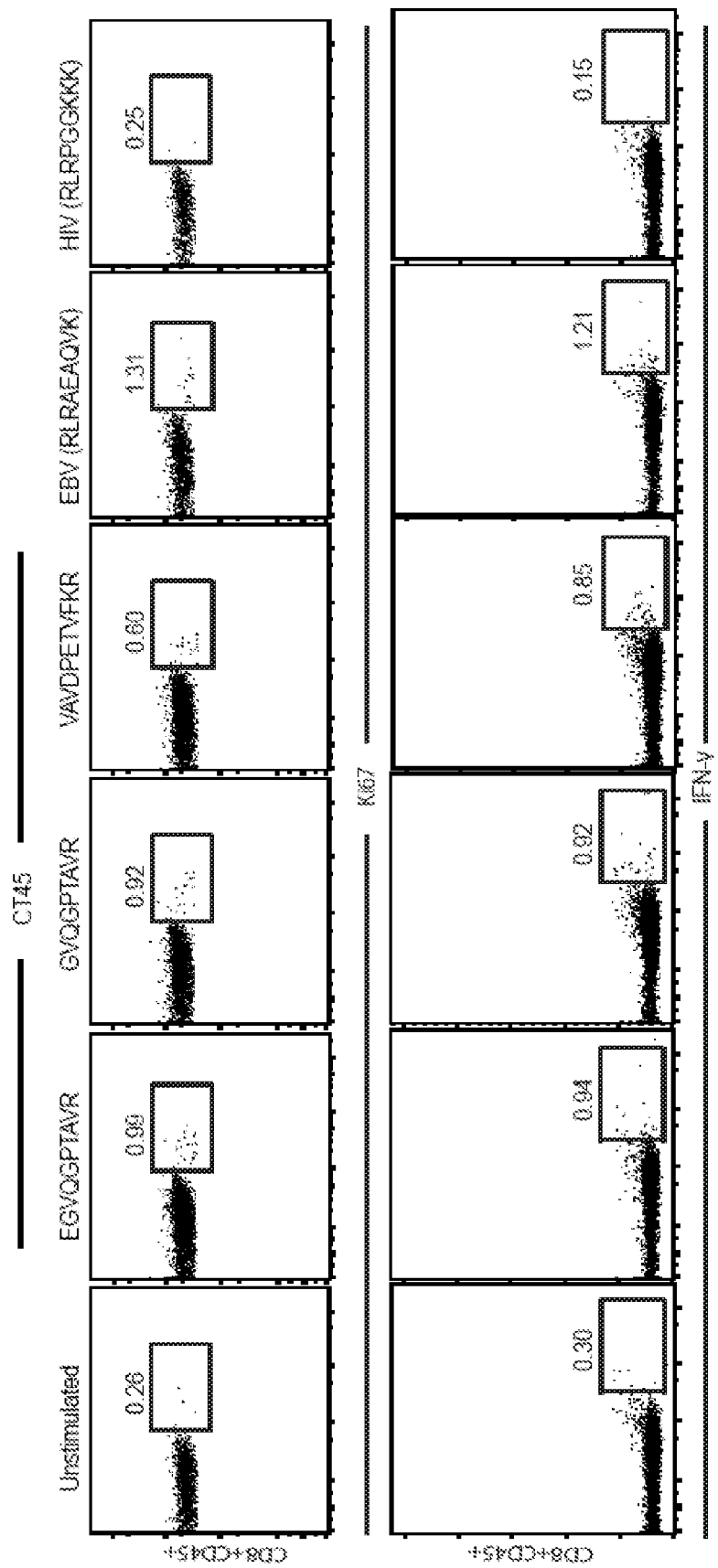

To address if the identified epitopes function as targets for CD8+ T cells, patient derived A-11:01 CD8+ T cells collected from a CT45 positive tumor were stimulated with the two CT45 peptides with the best binding affinity predictions (AVDPETVFK-SEQ ID NO:1 and GVQGPTAVRK-SEQ ID NO:3). Both CT45 peptides, but not a control peptide, induced T cell activation as assessed by Ki67 and intracellular IFNγ staining of CD8+ T cells (FIG. 11D). Similar results were obtained using A-03:01 CD8+ T cells using three peptides identified after DAC treatment (FIG. 18E). The A-11:01 CD8+ T cells reacted with one of two CT45 tetramers (A-11) containing the peptide, AVDPETVFK (SEQ ID NO:1), which had the highest predicted affinity for A-11:01, while A-03:01 CD8+ T cells reacted with the tetramer (A-03) containing the GVQPTAVRK peptide (FIG. 11E). Co-culture of the CT45+59M cell line with peptide stimulated A-11:01 CD8+ tumor-infiltrating lymphocytes (TIL) targeting two different CT45 peptides lysed the cancer cells in a dose-dependent manner (FIG. 11F). These data demonstrate that CT45 is an endogenously processed and presented antigen recognized and targeted by patient-derived CD8+ T cells.

C. CT45 is a Functional Mediator of Chemosensitivity

Figure 12A:
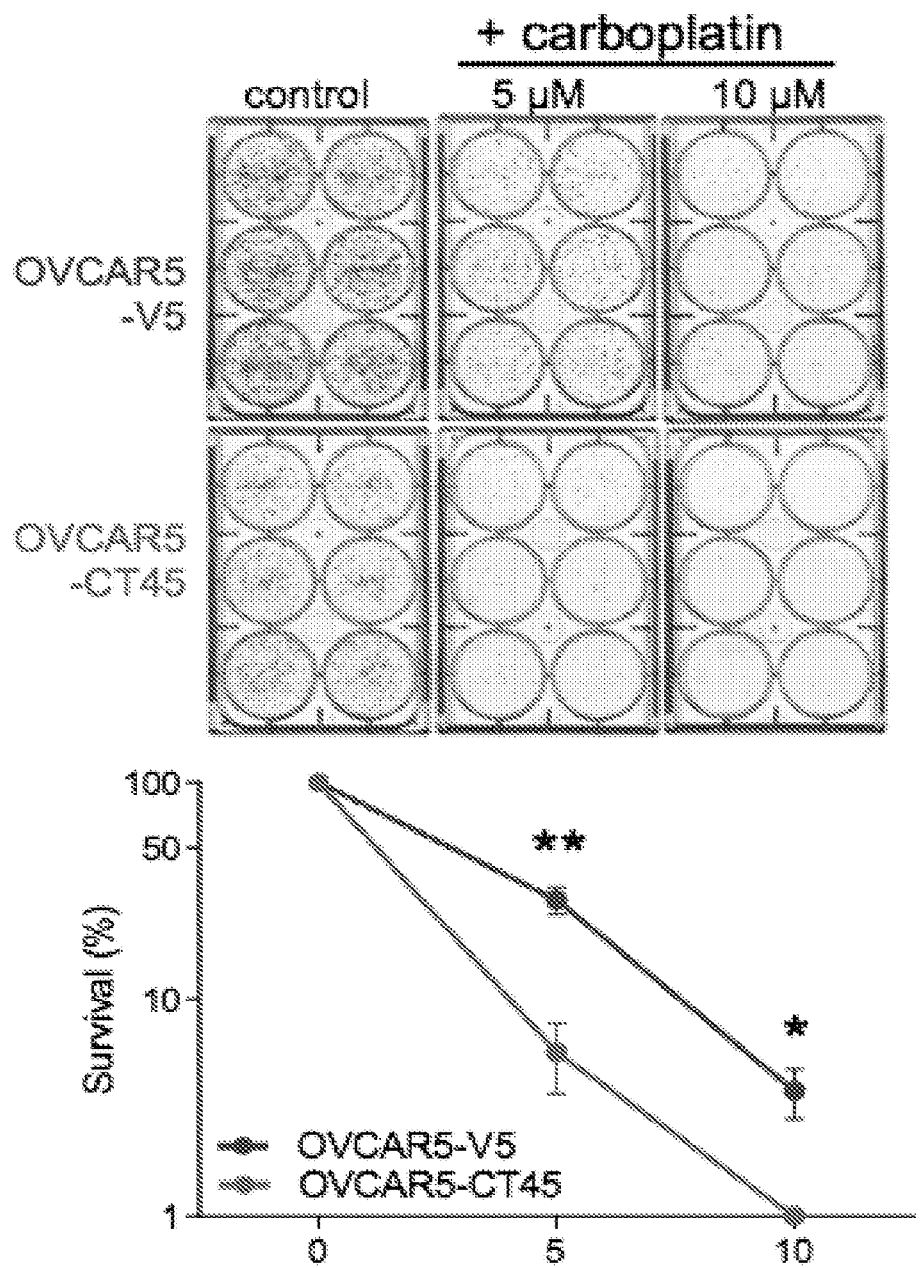

In addition to DAC's ability to modulate the immune response, it also shows synergism with platinum agents in ovarian cancer therapy. DAC sensitized SKOV3ip1 ovarian cancer cells to carboplatin (FIG. 19A) and intriguingly, proteomic analysis on DAC treated cells revealed that CT45 was among the top ten DAC induced proteins (FIG. 11B). Overexpression of CT45 in an ovarian cancer cell line reduced the number of colonies in a colony formation assay (FIG. 12A) but did not affect proliferation or the cell cycle (FIG. 19C-D). Addition of carboplatin reduced proliferation and colony formation in CT45 expressing cells (FIG. 19C and FIG. 12A). Similar effects were observed in a second serous ovarian cancer cell line, OVKATE (FIG. 19B, E). Treatment with carboplatin significantly reduced growth of CT45 expressing subcutaneous tumors in an immunodeficient mouse as compared to the untreated CT45+ tumors while having no effect on the vector control cell line (FIG. 12B). CT45 expression also significantly reduced overall tumor growth as compared to the vector control (FIG. 12B). This data reveals a functional link between CT45 expression and carboplatin chemosensitivity and highlights the potential tumor suppressive capacities of CT45 in ovarian cancer.

Figure 19F:
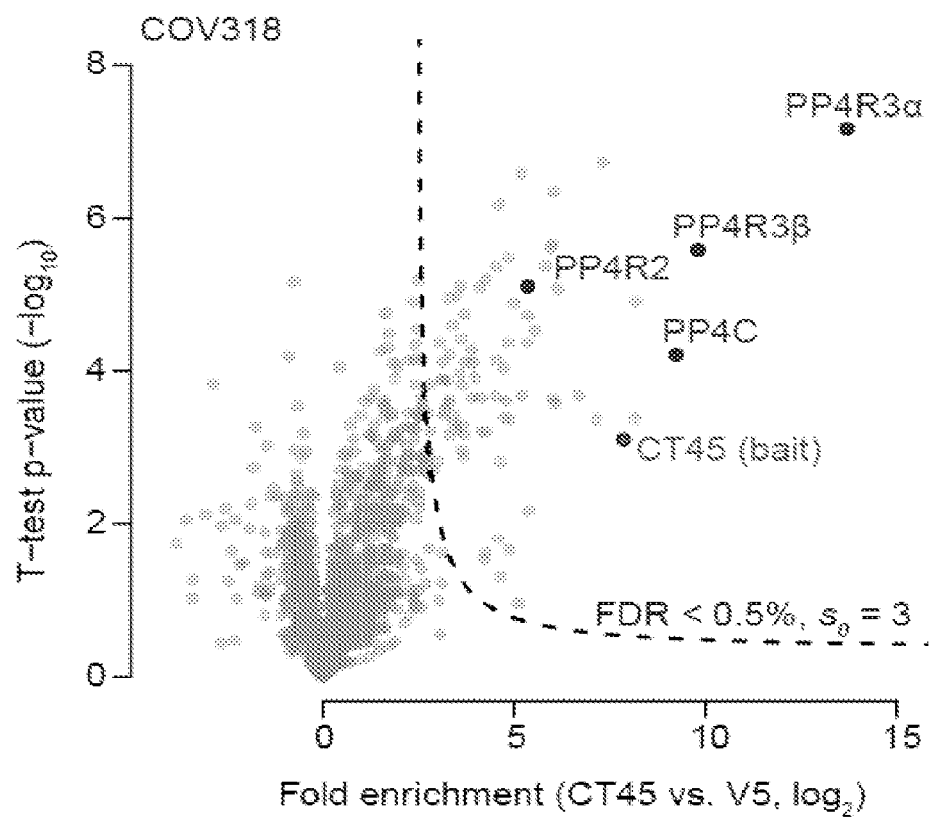

To understand the mechanism of CT45-mediated chemosensitivity, the inventors mined a recent quantitative human interactome study published by the inventors' laboratory. Interestingly, it was found that CT45 interacts with several members of the evolutionarily conserved protein phosphatase 4 (PP4) complex. The PP4 interaction was confirmed in two ovarian cancer cell lines (OVCAR-5 and COV318) expressing Flag or V5-tagged CT45, respectively. The regulatory subunits PP4R3α, PP4R3β, and PP4R2 as well as the catalytic subunit, PP4C, of PP4 were all highly significantly enriched in CT45 immunoprecipitates (p<0.001; FIG. 12C-D, FIG. 19F) pointing to their specific and direct interaction with CT45. Since PP4 deficiency impedes the DNA damage response (DDR) and causes hypersensitivity to platinum compounds, the inventors next investigated if CT45 expression influenced the level of DNA damage in ovarian cancer cells following treatment with carboplatin. Indeed, CT45-expressing cancer cells showed increased levels of the DNA damage marker γH2AX and cleaved caspase-3 after carboplatin exposure (FIG. 12E). In addition, more DNA damage was present in CT45-expressing cells as demonstrated by longer tail moments in a comet assay (FIG. 12F).

D. CT45 Promotes Chromatin Relaxation Mediated by KAP1 Phosphorylation

Figure 20A:
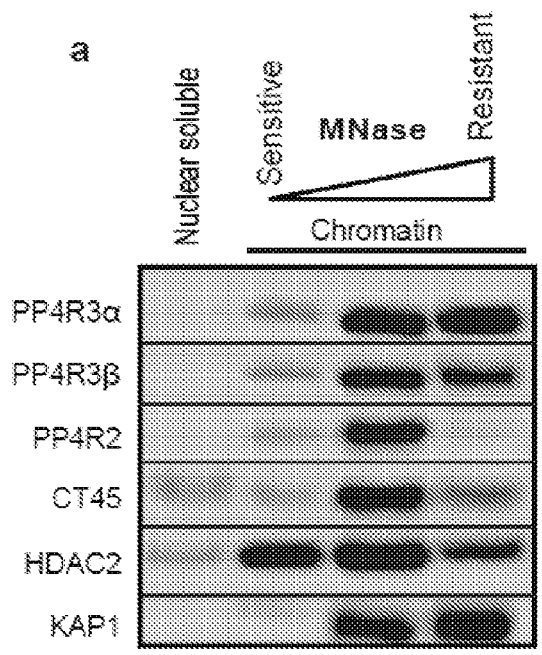

PP4 plays an important role in the DNA damage response by dephosphorylating several critical proteins including 53BP125, γH2AX22,28, RPA223, and KAP-1/TRIM2829, 30. Using a candidate based approach the inventors found that carboplatin treatment induced phosphorylation of KAP-1 at the ATM target site Ser82431. Phosphorylation was increased in CT45-expressing cells as compared to vector control cells following DNA damage (FIG. 13A). Consistent with these results, phosphorylated KAP-1 was pan-nuclear, peaking at day 3 following carboplatin treatment in both cell lines (FIG. 13B). In CT45-expressing cells p-KAP-1 peaked at a higher level and remained elevated on day 5 and day 7, while the p-KAP-1 signal dissipated to baseline levels by day 7 in control cells. The inventors observed similar trends for γH2AX. KAP-1 is a building block of heterochromatin important for chromatin condensation32 exerts it's function on chromatin and to understand whether CT45 is also associated with chromatin, the inventors analyzed both ectopically (OVCAR5-CT45) and endogenously (59M) CT45 expressing cells using a biochemical chromatin segregation assay. CT45 was strongly chromatin-enriched and associated with nuclease resistant heterochromatin, similar to its PP4 interaction partners, as well as the known heterochromatin linked proteins HDAC2 and KAP-1 (FIG. 13C and FIG. 20A). One possibility for how CT45 may inhibit KAP-1 dephosphorylation is by altering KAP-1 retention on the chromatin, but the inventors did not find that either CT45 or carboplatin altered the chromatin enrichment of KAP-1 or PP4 (FIG. 20B).

Furthermore, chromatin-immunoprecipitation coupled to mass spectrometry (ChIP-MS) confirmed an association of CT45 with heterochromatin as indicated by the co-enrichment of KAP1 and HDAC2 in addition to the PP4 complex (FIG. 13D). Pathway analysis of the CT45 interactome revealed a strong enrichment of heterochromatic and DDR linked proteins (FIG. 13E). Reciprocal ChIP-MS using KAP-1 as a bait showed a clear enrichment of CT45, independently confirming its association with chromatin (FIG. 20D-E). The interaction of CT45 with heterochromatin-associated PP4 was not affected by carboplatin (FIG. 20C).

Figure 13I:
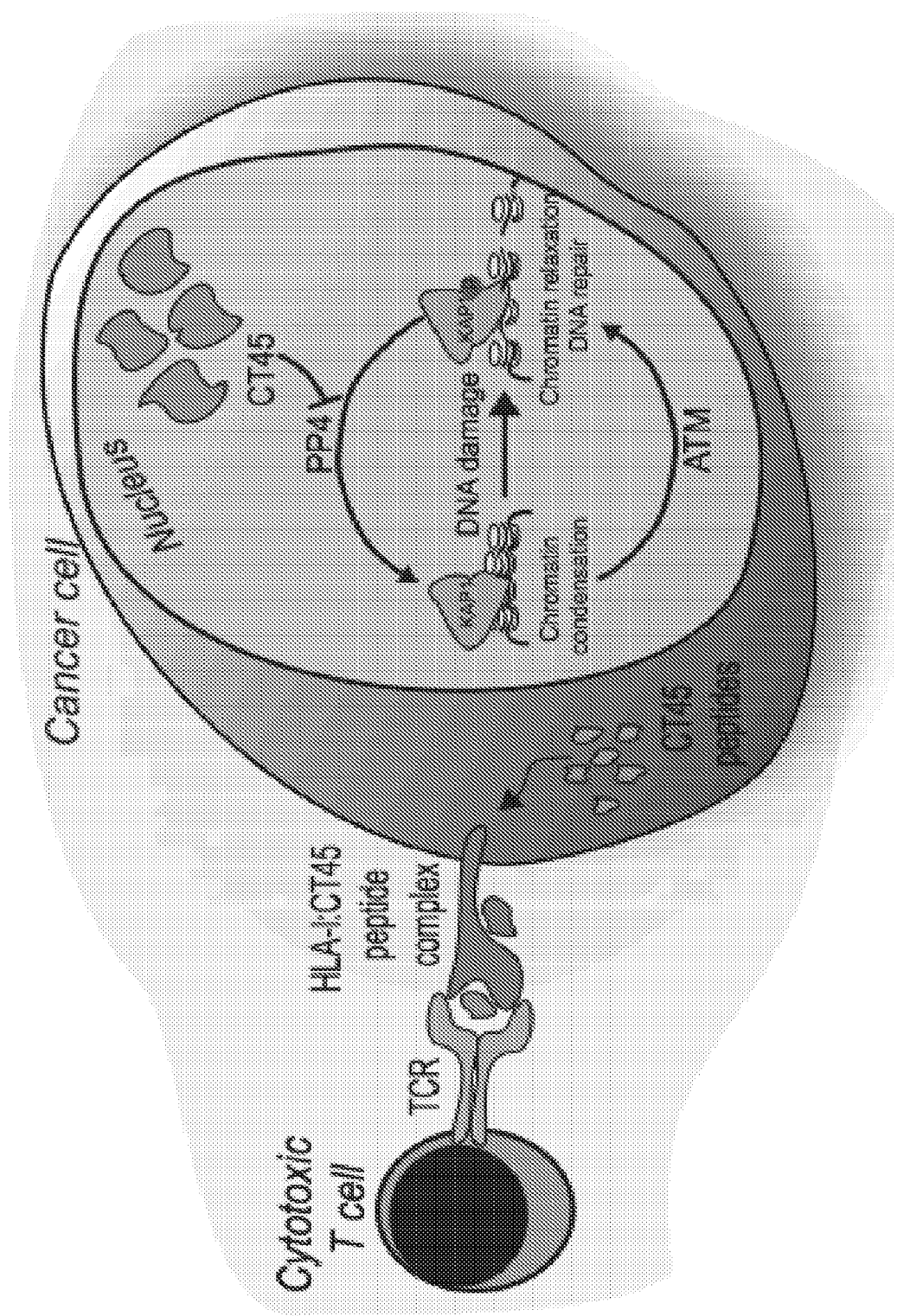

Since KAP-1 phosphorylation at S824 induces global chromatin decondensation following DNA damage, the inventors next asked if the KAP-1 Ser-824 phosphorylation differences caused changes in chromatin structure. Following carboplatin treatment, cells expressing CT45 had larger nuclei on day 5 suggesting an increased level of relaxed chromatin (FIG. 13F). Structural chromatin changes were interrogated using a micrococcal nuclease (MNase) assay at several time points following carboplatin exposure. After five days, carboplatin treatment induced global chromatin relaxation in both vector control and the CT45 overexpressing cell line. Strikingly, CT45 induced a higher proportion of nuclease-accessible chromatin compared to vector control cells (FIG. 13G-H) indicating that the chromatin is more accessible to platinum-induced chromatin damage. Furthermore, whereas the control cells completely restored chromatin compaction at day 7, chromatin in CT45 expressing cells remained in a relaxed conformation suggesting that CT45 impedes the KAP-1 mediated restoration of chromatin compaction through its binding to PP4 during recovery from DNA damage (FIG. 13I).

Mutational load correlates with clinical response to CTLA-4 blockade in melanoma and to PD-1 inhibition in colorectal cancers with mismatch-repair deficiencies. Therefore, most immunotherapy approaches have focused on cancers with a high mutational load and the presence of mutant antigens. Notably, ovarian cancer patients treated with immune checkpoint inhibitors have not experienced the impressive response rates evident in some other cancers. This has been attributed to the low mutational burden present in ovarian tumors which are characterized by copy number alterations. In the discovery cohort several patients showed long term survival following treatment with surgery and chemotherapy. Two of these patients are positive for the HLA class I alleles A-03:01 or A-11:01 which bind the CT45 derived peptides the inventors discovered using immunopeptidomics (FIG. 11). It was hypothesized that CT45 may serve as a non-mutant tumor rejection antigen that provides long-term protection to patients through activation of cytotoxic T cells which inhibit cancer growth. Based on these studies, one could envision a treatment approach where CT45 expression is activated on tumor cells (e.g. by DAC) and targeted by T cells engineered to recognize the CT45 peptide: HLA-I complex.

Using interaction proteomics, it found that CT45 directly interacts with the evolutionarily conserved protein phosphatase 4 complex, mediating sensitivity to the DNA damaging agent carboplatin by impeding dephosphorylation of KAP-1. Phosphorylated KAP-1 provides a global signal to transiently relax chromatin in order for DNA damage repair to occur. The data provided in this application indicates that CT45 prevents chromatin associated PP4 from dephosphorylating KAP-1 and thereby suspends chromatin in a relaxed state (FIG. 13I). Over time this leads to would lead to further accumulation of platinum induced DNA damage as more of the chromatin is exposed and ultimately result in cell death.

Overall, this data suggest a model (FIG. 13I) whereby CT45 functions as both a cell intrinsic mediator of chemosensitivity by impeding KAP-1 mediated chromatin condensation during recovery from DNA damage and as an antigen for CD8+ T cells. Both these findings may be clinically relevant. It is proposed that CT45 expression could be activated in tumors lacking CT45 by treating with demethylating agents to improve efficacy of chemotherapy both during first line therapy and with recurrent disease. Furthermore, immunotherapy targeting CT45 either alone or in combination with platinum-based chemotherapy could be an effective strategy for the treatment of advanced stage ovarian cancer.

E. Methods

1. Cell Lines and Reagents

SKOV3ip1 (from Dr. Gordon Mills, M. D. Anderson Cancer Center, Houston, TX), OVCAR5 (UCSF) and COV318 (from Dr. Gottfried Koneczny, UCLA) were cultured in DMEM, 10% FBS. 59M (ECACC) was cultured in DMEM, 10% FBS supplemented with 10 µg/ml bovine insulin (Sigma, MO). OVKATE (from Dr. Gottfried Koneczny, UCLA) were cultured in RPMI-1640, 10% FBS. All cell lines were tested for *mycoplasma* and authenticated using a commercial service (CellCheck, IDEXX Bioresearch). Growth factor reduced Matrigel was from BD Biosciences (Rockville, MD). pLX304 was a gift from Dr. David Root (Addgene plasmid #25890). pLX304-CT45A5 was acquired from DNASU Plasmid Repository (clone HsCD00446210). 3×FLAG-CT45A1 was synthesized (Eurofins) and cloned into pcDNA3.1 (Invitrogen). The Ki-CT45-2 antibody (used for WB and IMF) was a kind gift of Hans-Jürgen Heidebrecht. W6/32 monoclonal antibodies were purified from the growth medium of HB95 cells that were grown in CELLine CL-350 flask (Wilson Wolf Manufacturing Corporation, Minnesota) using Protein-A Sepharose (Invitrogen, CA). Antibodies acquired from Cell Signaling Technology were: γH2AX (9718, rabbit), Cleaved Caspase-3 (9661), anti-rabbit IgG-HRP (#7074), and anti-mouse IgG-HRP (#7076), normal rabbit IgG (#2729). Antibodies acquired from Bethyl laboratories were: PP4C (A300-835A), PP4R3β (A300-842A), KAP1 (A300-274A), pS824-KAP1 (A300-767A). Other antibodies used were: actin (Sigma, #A5441), anti-CT45A antibody (Sigma, SAB1301842), γH2AX (mouse, Thermo Scientific, #MA1-2022), and V5 (Life Technologies, #MA5-15253), PP4R2 (Atlas antibodies, HPA034695), PP4R3a (Atlas antibodies, HPA002568). HLA-I types of cell lines were determined using high-resolution genotyping (Center for Human Genetics and Laboratory Medicine, Martinsried).

2. FFPE Tissue Preparation for MS Analysis

Tumors were collected from patients undergoing primary debulking surgery by a gynecologic oncologist at the University of Chicago Hospital, Department of Obstetrics and Gynecology, Section of Gynecologic Oncology. Informed consent was obtained before surgery and the study was approved by the IRB of the University of Chicago. FFPE biobank specimens (5 serial sections, 10 µM thick) were first deparaffinized as previously describe. Areas containing 70% or more tumor were macrodissected from the slide using a scalpel blade. Lysis was then carried out in 4% SDS, 10 mM Hepes pH 8.0 at 99° C. for 60 min and by 15 min sonication (level 5, Bioruptor, Diagenode). Proteins in the cleared lysate (16,000 g, 10 min) were reduced with 10 mM DTT for 30 min and alkylated with 55 mM iodoacetamide for an additional 30 min. 100 ug of proteins were purified from SDS by acetone precipitation and the protein pellet resolved in 100 µl 6 M urea/2 M thiourea (in 10 mM Hepes pH 8.0). LysC digestion was carried out with 1 µg of LysC for 3 h at room temperature. After adding 4 volumes of 50 mM ammonium bicarbonate buffer, 1 µg trypsin was added for tryptic digestion overnight. The next day, digestion was stopped by adding 1% TFA. Peptides were finally desalted on C18 StageTips and kept at −20° C. until MS analysis. The majority of samples were injected twice for MS analysis.

3. Liquid Chromatography (LC)-MS Analysis of FFPE Samples

For LC-MS analysis, a Q Exactive (Thermo Fisher Scientific) mass spectrometer was used coupled on-line to an EASY-nLC 1000 HPLC system (Thermo Fisher Scientific). Desalted peptides were separated on in-house packed C18 columns (75 µm inner diameter, 50 cm length, 1.9 µm particles, Dr. Maisch GmbH, Germany) in a 250-min gradient from 2% to 60% in buffer B (80% acetonitrile, 0.5% formic acid) at 200 nl/min. Mass spectra were acquired in data-dependent mode. Briefly, each survey scan (range 300 to 1,650 m/z, resolution of 70,000 at m/z 200, maximum injection time 20 ms, ion target value of 3E6) was followed by high-energy collisional dissociation based fragmentation (HCD) of the 5 most abundant isotope patterns with a charge ≥2 (normalized collision energy of 25, an isolation window of 2.2 m/z, resolution of 17,500, maximum injection time 120 ms, ion target value of 1E5). Dynamic exclusion of sequenced peptides was set to 45 s. All data was acquired using Xcalibur software (Thermo Scientific).

4. Data Analysis of Proteomic Raw Files

MS raw files were processed with the MaxQuant software (version 1.5.3.15). The integrated *Andromeda* search engine was used for peptide and protein identification at an FDR of less than 1%. The human UniProtKB database (August 2015) was used as forward database and the automatically generated reverse database for the decoy search. 'Trypsin' was set as the enzyme specificity. A minimum number of 7 amino acids may be required for the peptide identification process. Proteins that could not be discriminated by unique peptides were assigned to the same protein group. Label-free protein quantification was performed using the MaxLFQ algorithm (MaxQuant environment). Briefly, quantification was based on extracted high-resolution 3D peptide features in mass-to-charge, retention time and intensity space. Only common peptides were used for pair-wise ratio calculations. Protein ratios were then determined based on median peptide ratios. The inventors required a minimum peptide ratio count of 1 to report a quantitative read-out and averaged the results from duplicate measurements of the same sample. The 'Match Between Runs' feature of MaxQuant was enabled to transfer peptide identifications across runs based on high mass accuracy and normalized retention times. Prior to data analysis, proteins, which were found as reverse hits or only identified by site-modification, were filtered out.

5. Tissue Microarray

Tissue microarrays (TMAs) were deparaffinized and rehydrated through xylenes and serial dilutions of EtOH to deionized water. They were incubated in antigen retrieval buffer (Tris-EDTA, pH 9, S2367, DAKO) and heated in steamer at over 97° C. for 20 minutes. Tissue sections were incubated in a humidity chamber with CT45A antibody (1:200, Sigma, SAB1301842) for 1 h at room temperature. The antigen-antibody binding was detected by Bond Polymer Refine Detection (DS9800, Leica Microsystems). Tissue sections were briefly immersed in hematoxylin for counterstaining and were covered with cover glasses. The stained TMAs were scored by an expert pathologist on a scale from 0-3. Data acquisition and analysis were blinded. Tumors were collected from patients undergoing primary debulking surgery by a gynecologic oncologist at the University of Chicago Hospital, Department of Obstetrics and Gynecology, Section of Gynecologic Oncology. Informed consent was obtained before surgery and the study was approved by the IRB of the University of Chicago.

6. HLA-I Peptidomics

SKOV3ip1 cells were treated with 500 nM 5-aza-2'-deoxycytidine (DAC) (Sigma, MO) for 3 days with DAC refreshed every 24 hours. After treatment cells were cultured an additional 4 days without DAC and collected for HLA-I purification at day 7. 59M cells were cultured under normal conditions prior to collection. HLA peptide purification, mass spectrometric analysis and data analysis were performed as previously described. The inventors used the GibbsCluster-1.0 Server tool to perform Gibbs clustering analysis of all identified 9-mer HLA-I peptides as input using the default settings for 1-6 clusters. The inventors compared the resulting motifs to the known and predicted motifs of the HLA-I alleles using the MHC motif viewer. Binding motifs were plotted using the Seq2Logo tool. The NetMHC 4.0 algorithm was used to model binding affinity of the identified peptides using default affinity thresholds for peptide binding (% rank 0.5 for strong binders and 2 for weak binders).

7. T Cell Peptide Stimulation

Tumors and ascites were collected from ovarian cancer patients undergoing primary debulking surgery at the University of Chicago. TILs were thawed and resuspended in RPMI, 10% FCS (or human serum). Cells were adjusted to $2\times10^6$/ml in 24-well plates and cultured for 7-10 days in the presence or absence of 1 μg/ml peptide. After 3 days, 6 IU/ml of rhIL-2 was added to the culture. Flow cytometric analysis of cultured cells was performed.

Intracellular cytokine staining: In vitro expanded TILs were restimulated at the end of culture with the relevant peptide (100 ng/ml) in the presence of Brefeldin A (BD Biosciences) for about 5-6 hours at 37° C. in a 5% $CO_2$ incubator. The cells were washed once with FACS buffer and stained with surface makers (anti-CD3, -CD8, live/dead stain) for 30 min on ice. Then the cells were fixed and permeabilization with the Cytofix/Cytoperm kit (BD Biosciences), and stained for cytokines using either anti-IFN-γ antibody. After washing, the cells were analyzed on a flow cytometer.

Tetramer staining: In vitro expanded TILs were stained with PE-labeled MHC Class I tetramers along with surface staining antibodies (anti-CD3, -CD8, live/dead stain) for 1 hour on ice. MHC class-I tetramers carrying CT45 antigen (GVQGPTAVRK (SEQ ID NO:3) AVDPETVFK (SEQ ID NO:1)) or HIV peptides (RLRPGGKKK (SEQ ID NO:34) or QVPLRPMTYK (SEQ ID NO:35)) were used. After washing, the cells were analyzed on a flow cytometer.

$^{51}$Cr release assays: 59M or SKOV3ip1 tumor cell lines (target cells) were labeled with 100 μCi $^{51}$Cr at 37° C. for 1 hour. Target cells were than washed three times in PBS, resuspended in culture medium at $1\times10^5$ viable cells/ml and 100 μl was added per well of a 96-well U-bottom plate. In vitro expanded TILs (effector cells) were washed twice in culture medium and added to targets at the given ratios. Plates were shortly centrifuged to settle cells, and incubated at 37° C. in a 5% $CO_2$ incubator for 5 hours after which time the supernatants were harvested, transferred to small tubes and counted using a Liquid Scintillation Counter. Spontaneous $^{51}$Cr release was evaluated in target cells incubated with medium alone. Maximal $^{51}$Cr release was measured in target cells incubated with zap solution at a final concentration of 1% (v/v). Percent specific lysis was calculated as (experimental-spontaneous lysis/maximal-spontaneous lysis) times 100.

8. Clonogenic Survival Assay

Cells were treated with different carboplatin concentrations for 48-72 hours. 2000 cells per 6-well were then plated for 7-9 days in drug-free medium. Grown colonies were fixed and stained with 1% formaldehyde, 1% methanol and 0.05% Crystal Violet for 20 min. Colony numbers were then counted with the Colony Area ImageJ plugin and plotted as percent of control on a logarithmic scale.

9. Western Blot Analysis

Cells were treated with indicated drugs for 3 days and then media was changed. On indicated day of collection, both adherent and non-adherent cells were collected in RIPA buffer (25 mM Tris-HCl pH 7.6, 150 mM NaCl, 1% NP-40, 0.5% sodium deoxycholate, 0.1% SDS) supplemented with protease inhibitor cocktail (Thermo Scientific) and phosphatase inhibitor cocktail (Sigma). Lysates were incubated for 30 min on ice, sonicated and cleared by centrifugation (15 min, 14 000 rpm, 4° C.). The quantity of protein was determined by BCA reagent (Pierce). The extracts were analyzed by SDS-PAGE on a 4-20% gradient gel (Bio-Rad).

10. Comet Assay

Cells were treated with carboplatin for 3 days and then incubated an additional 2 days without drug. The comet assay was performed on day 5 as previously described. Briefly, 2.5e4 cells/condition were resuspended in 70 uL 0.5% low melting point agarose (LMPA) at 37 C and plated on a glass slide precoated with 1% agarose in PBS. Samples were allowed to solidify at 4 C for 20 minutes with a square cover glass. The cover class was gently removed and a second 70 uL layer of 0.5% LMPA was applied and again allowed to solidify. The cover glass was removed and the slides immersed in Comet Lysis solution (2.5M NaCl, 100 mM EDTA, 10 mM Tris, 0.015% Triton X-100, pH 10) for one hour at 4 C and from this point forward protected from light. After lysis, the slides were equilibrated for 20 minutes in Comet Electrophoresis Buffer (0.3N NaOH, 1 mM EDTA, pH 10) at 4 C, and then run at 25V for 20 minutes. Then they were incubated at room temp in Comet Neutralization Buffer (0.4M Tris, pH 7.5) for five minutes twice, then in ddH2O for three minutes, stained with a 1:10,000 dilution of SYBR Gold in ddH2O, and finally mounted with a glass cover slip for imaging. Images were taken at 10× using a Zeiss AxioObserver A.1. At least 100 cells were quantified/sample using the software OpenComet. Data shown is the mean±s.e.m. of 4 biological repeats.

11. Mouse Experiments

Five million OVCAR5-V5 or OVCAR5-V5-CT45 cells suspended in a 1:2 solution of serum-free media to growth-factor reduced matrigel were injected subcutaneously into the right and left flanks respectively, of 8 weeks old female athymic nude mice. After 5 days, treatment was administered through the tail vein 1 time/week at 20 mg/kg. Sterile water served as the control treatment. Tumor growth was measured every 2-3 days using calipers until the tumor neared 1 cm$^3$ and was measured daily. Once the tumor reached 1 cm$^3$ the mouse was sacrificed. 4 mice were removed from the study early due to ulcerations of the skin. All experiments were approved by the Institutional Animal Care and Use Committee of the University of Chicago.

12. Affinity Purification and Mass Spectrometry

Affinity purification coupled to mass spectrometry (AP-MS) was performed as previously described. For immunoprecipitation of cell lines ectopically expressing N-terminally tagged CT45A1 (3×FLAG tag) or C-terminally tagged CT45A5 (V5 tag), 30 ul of ANTI-FLAG M2 Affinity Gel (Sigma) or ANTI-V5 Affinity Gel (Sigma, CLONE V5-10), respectively, was used and incubated with 1 mg of total lysate overnight at 4° C. For C-terminally tagged CT45A5 (V5 tag), 30 ul of Anti-V5 Agarose Affinity Gel (Sigma) was used.

Chromatin Experiments

For chromatin immunoprecipitation coupled to mass spectrometry (ChIP-MS), freshly harvested cells were cross-linked with 1% formaldehyde for 10 min in PBS. Cells were lysed in IP Buffer (50 mM Tris-HCl (pH 8), 100 mM NaCl, 5 mM EDTA (pH 8), 0.3% SDS, 1.7% Triton-X-100, supplemented with EDTA-free protease inhibitor cocktail (Roche) and phosphatase inhibitor cocktail (Roche)) and chromatin sonicated to an average size of 200-400 bp. 1 mg of total cell lysate was incubated with 3 µg of respective antibody overnight at 4° C. under constant rotation. The next day, 30 µl of protein G-coupled agarose beads (Cell signaling technology) were added and incubated for 3 h at 4° C. under constant rotation. Antibody-bait complexes were then washed three times with low salt wash buffer (50 mM HEPES pH 7.5, 140 mM NaCl, 1% Triton), once with high salt wash buffer (50 mM HEPES pH 7.5, 500 mM NaCl, 1% Triton) and twice with TBS. Elution was carried out by a partial on-bead digest as recently described. Peptides were finally desalted with C18 StageTips prior to MS analysis.

Chromatin fractionation was performed as described previously. Soluble proteins and proteins bound to open or compacted chromatin were separated by stepwise increasing the salt and nuclease (MNase) treatment. 1E7 cells were washed with PBS and 1 ml low salt buffer (LSB: 10 mM HEPES [pH 7.4], 25 mM KCl, 10 mM NaCl, 1 mM MgCl2, 0.1 mM EDTA). Pelleted cells were then resuspended in six times the packed cell volume (PCV) of LSB supplemented with protease and phosphatase inhibitor cocktail (Roche). After snap freezing in liquid nitrogen, samples were quickly thawed and immediately centrifuged (10 min at 10,000 rpm). The pellet was resuspended in a volume of high-salt buffer (HSB: 50 mM Tris-HCl [pH 8.0], 5% [v/v] glycerol, 1 mM EDTA, 10 mM MgCl2, 400 mM KCl, supplemented with protease and phosphatase inhibitor cocktail), equal to 0.25 V of LSB. After centrifugation at 10,000 rpm (supernatant=nucleoplasmic fraction), the pellet was resuspended in a volume nuclease buffer containing 10 U/ml MNase (NEB) and incubated at 37° C. for 10 min and centrifuged for 5 min at 10,000 rpm (supernatant=chromatin fraction 1). The pellet was then resuspended in the same volume of nuclease buffer containing 100 U/ml MNase and incubated another 45 min at 37° C. before an equal V of solubilization buffer (nuclease buffer+2% [v/v] NP-40, 2% [v/v] Triton X-100, 600 mM NaCl) was added. After brief vortexing, samples were centrifuged (5 min, 10,000 rpm) and the supernatant collected (chromatin fraction 2). Finally, the pellet was resuspended in a volume of solubilization buffer and an equal V of denaturing buffer (50 mM Tris [pH 6.8], 1% [v/v] SDS, 100 mM DTT, 10% glycerol), briefly sonicated, boiled for 5 min, and centrifuged for 5 min at 10,000 rpm (supernatant=chromatin fraction 3).

Chromatin relaxation was assayed using the micrococcal nuclease (MNase) assay as previously described, with a few modifications. Briefly, nuclei from 1E6 cells were extracted with 300 µl ice-cold lysis buffer (10 mM Tris-HCl (pH 7.5), 10 mM NaCl, 3 mM MgCl2 and 0.4% IGPAL-CA-630) on ice for 5 min. After centrifugation (2,000 g for 5 min at 4° C.), nuclei were washed two times in lysis buffer and one time in 500 µl digestion buffer (0.32M sucrose, 50 mM Tris-HCl (pH7.5), 4 mM MgCl2, 1 mM CaCl2). Nuclei were then digested in digestion buffer with 50 gel units MNase (NEB) for 9 min at 27° C. in a final volume of 100 µl. The reaction was stopped by adding a final concentration of 1% SDS and 15 mM EGTA. Genomic DNA was purified and separated by gel electrophoresis (1.2% agarose).

13. Immunofluorescence

Cells were treated with 0 or 5 µM carboplatin on glass chamber slides. After 72 hr, media was changed. At designated timepoints, slides were fixed for 10 min at room temperature with 4% paraformaldehyde, cells were washed and permeabilized with PBS/0.1% Triton-X for 15 min and then blocked for 1 hr in blocking buffer (PBS/0.1% Triton-X/0.05% BSA/0.05% goat serum). Cells were washed three times and then were then incubated with primary antibody overnight diluted in blocking buffer at 4° C. Following three washes, cells were incubated with secondary antibody (diluted in blocking buffer) for 1 hr at room temperature and then with Hoechst 33342 for 2 min. Slides were mounted with ProLong Gold Antifade. Slides were imaged using a Zeiss LSM 510 microscope. Image analysis was performed using CellProfiler. A minimum of 100 cells/sample were analyzed. Data shown is the mean±s.e.m. of 4-5 biological repeats.

14. Statistical Analysis

All statistical and bioinformatics analyses were done using the freely available software Perseus (MaxQuant environment), R framework, Stata Version 14 (Stata Corp., College Station, TX) or GraphPad Prism (GraphPad). For pairwise proteomic comparisons, the inventors used a 2-sided t-test statistic including a permutation-based false discovery rate (FDR) of 1% (5% for FIG. 1b after filtering for at least 10 out of 25 valid values) and an so value of 2. Missing values were imputed based on a normal distribution (width=0.15; downshift=1.8). For analysis of clinicopathological data, comparisons between groups were performed using chi-squared or Fisher's exact tests for categorical variables and Wilcoxon rank-sum tests for continuous variables. Overall survival and disease-free survival was compared between groups using the log-rank test. The association between CT45 levels and disease-free days was assessed using Pearson correlation. Pathway enrichment analysis (FIG. 4e) was performed based on a Fisher exact test with a Benjamini-Hochberg FDR cutoff of 0.02. GOBP, CORUM and Uniprot Keyword annotations were used for the analysis.

Sample sizes were determined based on previous experience with the individual experiment except for animal studies where power calculations were used. With the exception of the tissue microarray analysis, no randomization or blinding was done for data acquisition or assessment of outcome. The mean and the standard error of the mean (s.e.m) indicating variance are reported for all graphs. For experiments making one comparison, data was analyzed using a two-tailed Mann Whitney U test to account for non-normal distribution of the data. For experiments with more than one comparison, One-Way ANOVA with Tukey's multiple comparisons post-test was used. Before applying ANOVA, we first tested whether the variation was similar among the groups using the Bartlett's test. Where the standard deviations were significantly different, a log 2 transformation was applied to the data before analysis. Differences were considered significant if $p<0.05$.

Although certain embodiments have been described above with a certain degree of particularity, or with reference to one or more individual embodiments, those skilled in the art could make numerous alterations to the disclosed embodiments without departing from the scope of this invention. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments. Any reference to a patent publication or other publication is a herein a specific incorporation by reference of the disclosure of that publication. The claims are not to be interpreted as including means-plus- or step-plus-function limitations, unless such a limitation is explicitly recited in a given claim using the phrase(s) "means for" or "step for," respectively.

REFERENCES

The following references, to the extent that they provide exemplary procedural or other details supplementary to those set forth herein, are specifically incorporated herein by reference.

1 Bowtell, D. D. et al. Rethinking ovarian cancer II: reducing mortality from high-grade serous ovarian cancer. Nature reviews. Cancer 15, 668-679, doi: 10.1038/nrc4019 (2015).

2 Cannistra, S. A. Cancer of the Ovary. New England Journal of Medicine 351, 2519-2529, doi: doi: 10.1056/NEJMra041842 (2004).

3 Cress, R. D., Chen, Y. S., Morris, C. R., Petersen, M. & Leiserowitz, G. S. Characteristics of Long-Term Survivors of Epithelial Ovarian Cancer. Obstetrics and gynecology 126, 491-497, doi: 10.1097/aog.0000000000000981 (2015).

4 Cox, J. et al. MaxLFQ allows accurate proteome-wide label-free quantification by delayed normalization and maximal peptide ratio extraction. Molecular & Cellular Proteomics, 1-32 (2014).

5 Zhang, W. et al. DNA hypomethylation-mediated activation of Cancer/Testis Antigen 45 (CT45) genes is associated with disease progression and reduced survival in epithelial ovarian cancer. Epigenetics 10, 736-748, doi: 10.1080/15592294.2015.1062206 (2015).

6 Network, T. C. G. A. R. Integrated genomic analyses of ovarian carcinoma. Nature 474, 609-615, doi: 10.1038/nature10166 (2011).

7 Simpson, A. J., Caballero, O. L., Jungbluth, A., Chen, Y. T. & Old, L. J. Cancer/testis antigens, gametogenesis and cancer. Nature reviews. Cancer 5, 615-625, doi: 10.1038/nrc1669 (2005).

8 Gjerstorff, M. F., Andersen, M. H. & Ditzel, H. J. Oncogenic cancer/testis antigens: prime candidates for immunotherapy. Oncotarget (2015).

9 Chen, Y. T. et al. Expression of cancer testis antigen CT45 in classical Hodgkin lymphoma and other B-cell lymphomas. Proceedings of the National Academy of Sciences of the United States of America 107, 3093-3098, doi: 10.1073/pnas.0915050107 (2010).

10 Andrade, V. C. et al. Frequency and prognostic relevance of cancer testis antigen 45 expression in multiple myeloma. Experimental hematology 37, 446-449, doi: 10.1016/j.exphem.2008.12.003 (2009).

11 Chen, Y. T. et al. Multiple cancer/testis antigens are preferentially expressed in hormone-receptor negative and high-grade breast cancers. PloS one 6, e17876, doi: 10.1371/journal.pone.0017876 (2011).

12 Chen, Y. T. et al. Cancer/testis antigen CT45: analysis of mRNA and protein expression in human cancer. International journal of cancer. Journal international du cancer 124, 2893-2898, doi: 10.1002/ijc.24296 (2009).

13 Heidebrecht, H. J. et al. Characterization and expression of CT45 in Hodgkin's lymphoma. Clinical cancer research: an official journal of the American Association for Cancer Research 12, 4804-4811, doi: 10.1158/1078-0432.CCR-06-0186 (2006).

14 Rudolph, P. et al. Ki-A10, a germ cell nuclear antigen retained in a subset of germ cell-derived tumors. The American journal of pathology 154, 795-803, doi: 10.1016/S0002-9440 (10) 65326-6 (1999).

15 Chen, Y. T. et al. Identification of cancer/testis-antigen genes by massively parallel signature sequencing. Proceedings of the National Academy of Sciences of the United States of America 102, 7940-7945, doi: 10.1073/pnas.0502583102 (2005). 16 Bassani-Sternberg, M., Pletscher-Frankild, S., Jensen, L. J. & Mann, M. Mass spectrometry of human leukocyte antigen class I peptidomes reveals strong effects of protein abundance and turnover on antigen presentation. Molecular & cellular proteomics: MCP 14, 658-673, doi: 10.1074/mcp.M114.042812 (2015).
17 Li, H. et al. Immune regulation by low doses of the DNA methyltransferase inhibitor 5-azacitidine in common human epithelial cancers. Oncotarget 5, 587-598 (2014).
18 Wrangle, J. et al. Alterations of immune response of Non-Small Cell Lung Cancer with Azacytidine. Oncotarget 4, 2067-2079, doi: 10.18632/oncotarget. 1542 (2013).
19 Matei, D. et al. Epigenetic resensitization to platinum in ovarian cancer. Cancer research 72, 2197-2205, doi: 10.1158/0008-5472.can-11-3909 (2012).
20 Plumb, J. A., Strathdee, G., Sludden, J., Kaye, S. B. & Brown, R. Reversal of Drug Resistance in Human Tumor Xenografts by 2'-Deoxy-5-azacytidine-induced Demethylation of the hMLH1 Gene Promoter. Cancer research 60, 6039-6044 (2000).
21 Chiappinelli, K. B. et al. Inhibiting DNA Methylation Causes an Interferon Response in Cancer via dsRNA Including Endogenous Retroviruses. Cell 162, 974-986, doi: 10.1016/j.cell.2015.07.011 (2015).
22 Shang, B. et al. CT45A1 acts as a new proto-oncogene to trigger tumorigenesis and cancer metastasis. Cell death & disease 5, e1285, doi: 10.1038/cddis.2014.244 (2014).
23 Koop, A. et al. Down-regulation of the cancer/testis antigen 45 (CT45) is associated with altered tumor cell morphology, adhesion and migration. Cell communication and signaling: CCS 11, 41, doi: 10.1186/1478-811X-11-41 (2013).
24 Hein, M. Y. et al. A Human Interactome in Three Quantitative Dimensions Organized by Stoichiometries and Abundances. Cell 163, 712-723, doi: 10.1016/j.cell.2015.09.053 (2015).
25 Lee, D. H. et al. Dephosphorylation enables the recruitment of 53BP1 to double-strand DNA breaks. Molecular cell 54, 512-525, doi: 10.1016/j.molcel.2014.03.020 (2014).
26 Chowdhury, D. et al. A PP4-phosphatase complex dephosphorylates gamma-H2AX generated during DNA replication. Molecular cell 31, 33-46, doi: 10.1016/j.molcel.2008.05.016 (2008).
27 Lee, D. H. et al. A PP4 phosphatase complex dephosphorylates RPA2 to facilitate DNA repair via homologous recombination. Nature structural & molecular biology 17, 365-372, doi: 10.1038/nsmb.1769 (2010).
28 Shaltiel, I. A. et al. Distinct phosphatases antagonize the p53 response in different phases of the cell cycle. Proceedings of the National Academy of Sciences 111, 7313-7318, doi: 10.1073/pnas.1322021111 (2014).
29 Lee, D. H. et al. Phosphoproteomic analysis reveals that PP4 dephosphorylates KAP-1 impacting the DNA damage response. Vol. 31 (2012).
30 Wisniewski, J. R. et al. Absolute Proteome Analysis of Colorectal Mucosa, Adenoma, and Cancer Reveals Drastic Changes in Fatty Acid Metabolism and Plasma Membrane Transporters. Journal of proteome research 14, 4005-4018, doi: 10.1021/acs.jproteome.5b00523 (2015).
31 Wisniewski, J. R., Ostasiewicz, P. & Mann, M. High recovery FASP applied to the proteomic analysis of microdissected formalin fixed paraffin embedded cancer tissues retrieves known colon cancer markers. Journal of proteome research 10, 3040-3049, doi: 10.1021/pr200019m (2011).
32 Mukhopadhyay, A. et al. Development of a Functional Assay for Homologous Recombination Status in Primary Cultures of Epithelial Ovarian Tumor and Correlation with Sensitivity to Poly(ADP-Ribose) Polymerase Inhibitors. Clinical Cancer Research 16, 2344-2351, doi: 10.1158/1078-0432.ccr-09-2758 (2010).
33 Mukhopadhyay, A. et al. Clinicopathological Features of Homologous Recombination-Deficient Epithelial Ovarian Cancers: Sensitivity to PARP Inhibitors, Platinum, and Survival. Cancer research 72, 5675-5682, doi: 10.1158/0008-5472.can-12-0324 (2012).

The invention claimed is:

1. An in vitro CT45 targeting agent comprising i) isolated dendritic cells comprising an extra-chromosomal CT45 polypeptide; or ii) an isolated dendritic cell primed with a CT45 polypeptide; wherein the CT45 polypeptide consists of a polypeptide that has the length and amino acid sequence of one of SEQ ID NOS: 1-6 or 29-33.

2. A method for treating ovarian cancer in a patient comprising administering the in vitro CT45 targeting agent of claim 1 to the patient.

3. The in vitro CT45 targeting agent of claim 1, wherein the T cells or dendritic cells are autologous.

4. The in vitro CT45 targeting agent of claim 1, wherein the polypeptide consists of a polypeptide that has the amino acid sequence and length of one of SEQ ID NO:1, 3, or 6.

5. The in vitro CT45 targeting agent of claim 1, wherein the CT45 targeting agent comprises: isolated dendritic cells comprising an extra-chromosomal CT45 polypeptide; wherein the CT45 polypeptide consists of a polypeptide that has the length and amino acid sequence of one of SEQ ID NOS: 1-6 or 29-33.

6. The in vitro CT45 targeting agent of claim 1, wherein the CT45 targeting agent comprises: an isolated dendritic cell primed with a CT45 polypeptide; wherein the CT45 polypeptide consists of a polypeptide that has the length and amino acid sequence of one of SEQ ID NOS: 1-6 or 29-33.

* * * * *